(12) United States Patent
Feng et al.

(10) Patent No.: US 11,857,635 B2
(45) Date of Patent: Jan. 2, 2024

(54) LINKER COMPOUND, POLYETHYLENE GLYCOL-LINKER CONJUGATE AND DERIVATIVE THEREOF AND POLYETHYLENE GLYCOL-LINKER-DRUG CONJUGATE

(71) Applicant: JENKEM TECHNOLOGY CO., LTD. (TIANJIN), Tianjin (CN)

(72) Inventors: Zewang Feng, Tianjin (CN); Qingbin Wang, Tianjin (CN); Jinliang Wang, Tianjin (CN); Yanping Song, Tianjin (CN); Yanli Xiong, Tianjin (CN); Leimin Wang, Tianjin (CN); Jinghui Du, Tianjin (CN); Xuan Zhao, Tianjin (CN)

(73) Assignee: JenKem Technology Co., Ltd. (Tianjin), Tianjin (CN)

( * ) Notice: Subject to any disclaimer, the term of this patent is extended or adjusted under 35 U.S.C. 154(b) by 673 days.

(21) Appl. No.: 16/833,988

(22) Filed: Mar. 30, 2020

(65) Prior Publication Data

US 2020/0289655 A1 Sep. 17, 2020

Related U.S. Application Data

(63) Continuation of application No. PCT/CN2018/106972, filed on Sep. 21, 2018.

(30) Foreign Application Priority Data

Sep. 30, 2017 (CN) .......................... 201710919466.5
Mar. 7, 2018 (CN) .......................... 201810186781.6
Sep. 7, 2018 (CN) .......................... 201811043884.3

(51) Int. Cl.
*A61K 47/60* (2017.01)
*A61K 31/704* (2006.01)
*A61P 35/00* (2006.01)

(52) U.S. Cl.
CPC ............ *A61K 47/60* (2017.08); *A61K 31/704* (2013.01); *A61P 35/00* (2018.01)

(58) Field of Classification Search
CPC .. A61K 47/60; A61K 31/704; A61K 38/2013; A61P 31/04; A61P 31/12; A61P 37/02
See application file for complete search history.

(56) References Cited

U.S. PATENT DOCUMENTS 6,180,095 B1  1/2001 Greenwald et al.
2001/0031873 A1* 10/2001 Greenwald ............. A61P 35/00
                                                568/38

FOREIGN PATENT DOCUMENTS

| CN | 101104077 A | 1/2008 | |
|---|---|---|---|
| CN | 101104078 A | 1/2008 | |
| CN | 101242858 A | 8/2008 | |
| CN | 102448494 A | 5/2012 | |
| CN | 103083680 A | 5/2013 | |
| CN | 103483282 A | 1/2014 | |
| CN | 106310289 A | 1/2017 | |
| DE | 10319611 A1 | 11/2004 | |
| WO | WO-2005016240 A2 * | 2/2005 | .......... C07C 235/48 |
| WO | 2011097600 A1 | 11/2011 | |
| WO | 2013148579 A1 | 10/2013 | |

OTHER PUBLICATIONS

Greenwald, R. B.,"Controlled release of proteins from their poly (ethylene glycol) conjugates: drug delivery systems employing 1, 6-elimination." Bioconjugate chemistry 14.2 (2003): 395-403.*
Mehvar, R., "Modulation of the pharmacokinetics and pharmacodynamics of proteins by polyethylene glycol conjugation." J Pharm Pharm Sci 3.1 (2000): 125-36.*
PCT Written Opinion of the International Searching Authority, International application No. PCT/CN2018/106972, dated Dec. 6, 2018.
PCT International Search Report, International application No. PCT/CN2018/106972, dated Dec. 6, 2018.
The State Intellectual Property Office of People's Republic of China, First Office Action, Application No. or Publication No. 201811043884.3, dated Feb. 23, 2021.
The State Intellectual Property Office of People's Republic of China, Application No. or Publication No. 201810186781.6, dated May 17, 2019.
Yan Liu, Title of the article: Clone of Recombinant Human Interleukin-2 (IL-2) Mutant and Expression and Purification in Pasteur Pichia Pastoris System, Publisher: Chongqing University, Apr. 1, 2002, China.
STN Search Results for searches for Chemical Compositions, searched in the STN Registry, Copyright 2019 ACS on STN.

* cited by examiner

*Primary Examiner* — John M Mauro
(74) *Attorney, Agent, or Firm* — Flener IP & Business Law; Zareefa B. Flener

(57) ABSTRACT

The disclosure discloses a linker compound, a polyethylene glycol-linker conjugate and a derivative thereof, and a polyethylene glycol-linker-drug conjugate. The linker compound as well as the conjugate thereof with the polyethylene glycol and the derivative thereof may be used for modifying a drug, and a modification reaction is simple and easy to carry out. Moreover, a reaction yield is high, and an application range of the modified drug is wide. The modified drugs gradually degrade from a chain of the conjugate in vivo, and may stay in a lesion (such as a cancer site) for a longer period of time, achieving purposes of sustained and controlled release, reducing an administration frequency, and greatly improving a bioavailability of the drug and a patient compliance.

19 Claims, 3 Drawing Sheets

Time after administration (day)

LINKER COMPOUND, POLYETHYLENE GLYCOL-LINKER CONJUGATE AND DERIVATIVE THEREOF AND POLYETHYLENE GLYCOL-LINKER-DRUG CONJUGATE

CROSS-REFERENCE TO RELATED APPLICATIONS

This application is a continuation of International Application No. PCT/CN2018/106972 (filed on Sep. 21, 2018), which claims the benefit and priority of Chinese patent application No. CN201710919466.5 (filed on Sep. 30, 2017), application No. CN201810186781.6 (filed on Mar. 7, 2018) and application No. CN201811043884.3 (filed on Sep. 7, 2018), each of which is incorporated herein by reference in its entirety and for all purposes.

TECHNICAL FIELD

The present disclosure relates to the field of pharmaceutical technologies, and more particularly, to a linker compound, a polyethylene glycol-linker conjugate and a derivative thereof, as well as a polyethylene glycol-linker-drug conjugate and a pharmaceutical composition and an application thereof.

BACKGROUND

At present, many drugs are mainly administrated by means of injection in clinic since the drugs are not suitable for oral administration and due to other reasons (for example, when polypeptide and protein drugs are orally administered, they will be destroyed by hydrolysis environments such as various proteases and peptidases after entering a digestive tract, so that an efficacy will be reduced or even lost, for example, some drugs are irritating to the stomach or cannot resist acids, and are easy to be destroyed by gastric acid). Directly injecting these drugs into human tissues or blood vessels without passing through a digestive system and a liver prevents the drugs from being damaged by a digestive juice and affected by food, so that the drugs are absorbed fast, a blood drug concentration is raised rapidly, and a dosage of administration is accurate. However, in clinical application, the drugs are often distributed rapidly throughout the body after the administration, which result in poor targeting to lesions such as tumor tissues, low bioavailability, relatively low efficacy, rapid adverse reactions, and relatively difficult treatment. Moreover, multiple administrations are often required, and a principle of aseptic operation needs to be strictly observed during administration, requiring professionals such as doctors and nurses to operate, which is not conducive to patient compliance. Therefore, the clinical application of the drugs often encounters bottlenecks.

In the prior art, researchers often use a water soluble polymer such as polyethylene glycol to modify and link the drug to prolong a physiological half-life period of the drug and reduce an immunogenicity and a toxicity of the drug, but release and an efficacy of the drug in vivo are sometimes not ideal. It is found during testing that the water soluble polymer and the drug are linked through a linker to form a polymer-drug conjugate, and degradation of the drug from a chain of the conjugate can achieve the purposes of sustained and controlled release. The longer the drug stays in the lesion (e.g., cancer site), the lower an administration frequency is, which reduces inconvenience for patients to take the drug. For example, patent document CN200680029849.5 discloses a conjugate, which includes aromatic moieties containing ionizable hydrogen atoms such as fluorene, spacer moieties and water soluble polymers.

The inventor of the present disclosure obtains a linker compound and a conjugate of the linker compound and polyethylene glycol and a derivative thereof through a large number of tests and researches. When the linker compound is used for modifying a drug, a modification reaction is simple and easy to carry out, a reaction yield is high, an application range of the modified drug is wide, a release speed and an efficacy of the modified drugs in vivo are ideal, an administration frequency can be reduced, and a bioavailability of the drug and a patient compliance can be greatly improved.

SUMMARY

An object of the disclosure is to provide a linker compound.

Another object of the disclosure is to provide a conjugate of polyethylene glycol and the above linker and a derivative thereof.

Another object of the disclosure is to provide a polyethylene glycol-linker-drug conjugate.

Another object of the disclosure is to provide a pharmaceutical composition containing the above conjugate and a pharmaceutically acceptable carrier or additive.

Another object of the disclosure is to provide an application of the conjugate and the pharmaceutical composition above in preparing a drug for preventing and/or treating a disease.

Specifically, a first aspect of the disclosure provides a compound, which have structures as follows:

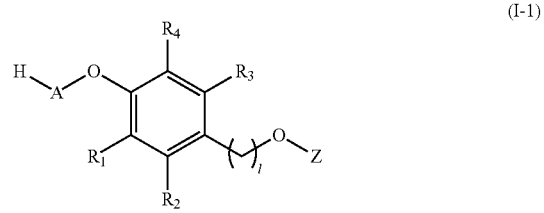

(I-1)

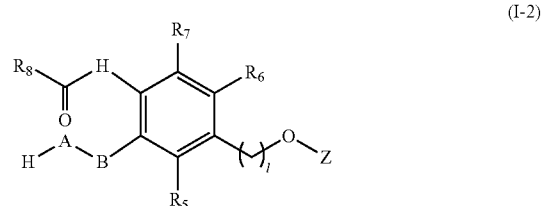

(I-2)

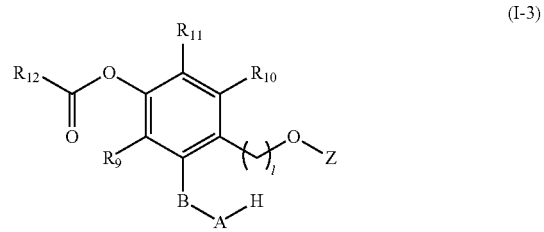

(I-3)

wherein, l is an integer of 1 to 5,

Z is selected from —H and a hydroxy protecting group,

A is selected from one or a combination of several of an amino acid residue, a polypeptide residue,

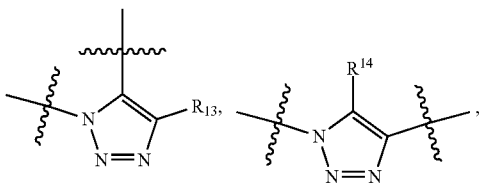

—(CH$_2$)$_i$—, —NHCO(CH$_2$)$_i$—, —CONH(CH$_2$)$_i$—, —(CH$_2$)$_i$NH— and —CO(CR$_{15}$R$_{16}$)$_i$NH—, and i is an integer of 0 to 6, the amino acid is selected from glycine, alanine, valine, leucine, isoleucine, serine, threonine, proline, aspartic acid, asparagine, glutamic acid, glutamine, lysine, arginine, cysteine, methionine, histidine, tryptophan, phenylalanine and tyrosine, R$_{1-7}$ and R$_{9-11}$ are independently selected from —H, —F, —Cl, —Br, —I, C1-6 alkyl, C1-6 alkoxy, C3-6 cycloalkyl, C1-6 alkenyl, C6-12 aryl, C6-12 aralkyl, C3-12 aromatic or non-aromatic heterocyclyl, C3-12 heterocyclic alkyl and —(CH$_2$)$_1$—O—Z, R$_8$ and R$_{12}$ are independently selected from C1-6 alkyl, R$_{13-16}$ are independently selected from —H and C1-6 alkyl, B is a linking group —B$_1$—B$_2$—, wherein, B$_1$ is selected from —(CH$_2$)$_j$—, —NHCO(CH$_2$)$_j$— and —CONH(CH$_2$)$_j$—, and j is an integer of 0 to 6, and B$_2$ is selected from —C═O, —C═S, —O—, —S—, —C(O)O—, —C(O)S—, —C(S)O— and —S—S—.

In the linker compound, l is an integer of 1 to 5, such as 1, 2, 3, 4, 5, and preferably 1, 2 or 3; and more preferably 1.

In the linker compound, those skilled in the art may select a proper hydroxy protecting group such as —CH$_3$, —C(CH$_3$)$_3$, —CH$_2$OCH$_3$, —COCH$_3$, —COC(CH$_3$)$_3$, —CH$_2$CH═CH$_2$, —Si(CH$_3$)$_3$,

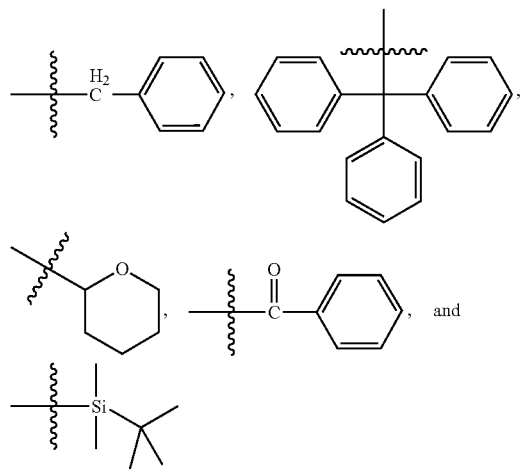

according to the actual requirements.

In one example of the disclosure, the Z is —H.

In one example of the disclosure, in the linker compound, the A is an amino acid residue, and the amino acid is selected from glycine, alanine, valine, leucine, isoleucine, serine, threonine, proline, aspartic acid, asparagine, glutamic acid, glutamine, lysine, arginine, cysteine, methionine, histidine, tryptophan, phenylalanine and tyrosine, preferably from glycine, alanine, valine, leucine, isoleucine, aspartic acid, asparagine, glutamic acid, glutamine and lysine, and more preferably from glycine, alanine and valine.

In another example of the disclosure, in the linker compound, the A is

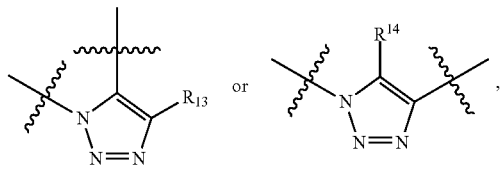

and preferably

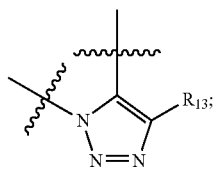

and in a specific example of the disclosure, A is

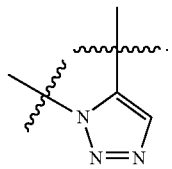 [SMILES: *c1cnnn1*]

In another example of the disclosure, in the linker compound, the A is one or a combination of several of —(CH$_2$)$_i$—, —(CH$_2$)$_i$NH— and —CO(CR$_{15}$R$_{16}$)$_i$NH—.

Preferably, in the linker compound, the R$_{1-7}$ and R$_{9-11}$ are independently selected from —H, —F, —Cl, —Br, —I, C1-6 alkyl, C1-6 alkoxy and —(CH$_2$)$_1$—O—Z; more preferably from —H, —F, —Cl, —CH$_3$, —CH$_2$CH$_3$, —CH$_2$CH$_2$CH$_3$, —CH(CH$_3$)$_2$, —C(CH$_3$)$_3$, —OCH$_3$ and —(CH$_2$)$_1$—O—Z; and further preferably from —H, —F, —Cl, —CH$_3$, —OCH$_3$ and —(CH$_2$)$_1$—O—Z.

In one example of the disclosure, the R$_{1-4}$ are all —H.

In one example of the disclosure, the R$_{5-7}$ are all —H.

In one example of the disclosure, the R$_{9-11}$ are all —H.

Preferably, in the linker compound, the R$_8$ and R$_{12}$ are independently selected from C1-4 alkyl such as methyl, ethyl, n-propyl, isopropyl, n-butyl, sec-butyl, isobutyl or tert-butyl; and more preferably, the R$_8$ and/or R$_{12}$ is methyl.

Preferably, in the linker compound, R$_{13-16}$ are independently selected from —H and C1-3 alkyl (such as methyl, ethyl, n-propyl or isopropyl).

Preferably, in the linker compound, R$_{15}$ is —H, and R$_{16}$ is selected from —H, methyl, ethyl, n-propyl and isopropyl.

In one example of the disclosure, R$_{13}$ and/or R$_{14}$ is —H.

Preferably, in the linker compound, i is an integer of 0 to 3, for example, 0, 1, 2, or 3.

Preferably, in the linker compound, j is an integer of 0 to 3, for example, 0, 1, 2, or 3.

Preferably, in one example of the disclosure, in formula I-1, the A is —COCH$_2$NH—, —COCH(CH$_3$)NH—, and —COCH(CH(CH$_3$)$_2$)NH—.

Preferably, the $B_2$ is selected from —C=O, —O—, —S—, —C(O)O—, —C(O)S— and —S—S—.

In one example of the disclosure, the $B_2$ is —C(O)O— or —O—.

In another example of the disclosure, the B is —(CH$_2$)$_j$O—, and j is an integer of 0 to 3, for example, 0, 1, 2 or 3.

In one example of the disclosure, in formulae I-2 and 1-3, the —B-A- is —OCH$_2$CH$_2$NH—.

In one example of the disclosure, the linker compound is selected from following structures:

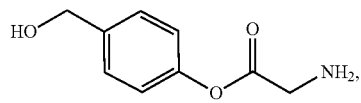
(L1)

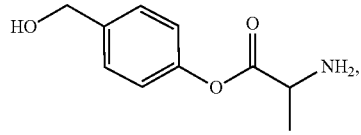
(L2)

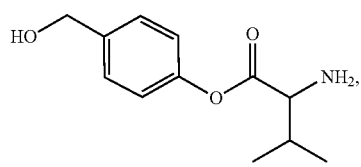
(L3)

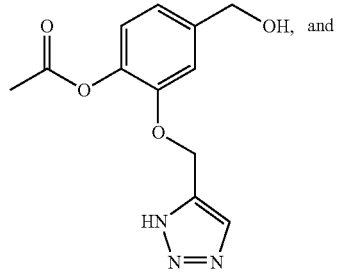
(L4)

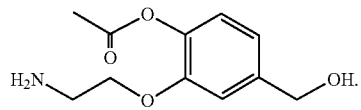
(L5)

Another aspect of the disclosure also provides a polyethylene glycol-linker conjugate, which has a structure as follows:

PEG-X-L   (II)

wherein, L is the above linker of the disclosure,

PEG is a polyethylene glycol residue, and

X is a linking group, which is selected from one or a combination of several of —(CH$_2$)$_a$—, —(CH$_2$)$_a$CO—, —(CH$_2$)$_a$OCO—, —(CH$_2$)$_a$NHCO—, —NH(CH$_2$)$_a$CO—, —(CH$_2$)$_a$SO$_2$—, —O(CH$_2$)$_a$—, —O(CH$_2$)$_a$CO—, —O(CH$_2$)$_a$OCO—, —O(CH$_2$)$_a$NHCO— and —O(CH$_2$)$_a$SO$_2$—, and a is an integer of 0 to 10.

In one example of the disclosure, the polyethylene glycol-linker conjugate have structures as follows:

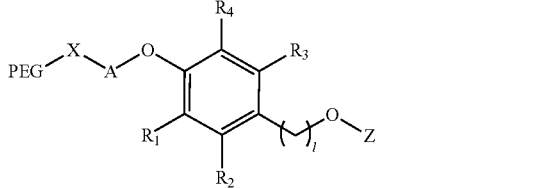
(II-1)

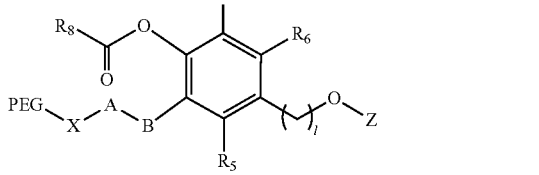
(II-2)

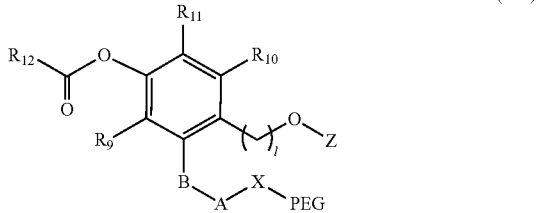
(II-3)

in the above formulae II-1 to II-3, the $R_{1-12}$, l, A, B, Z and the like have the above definitions of the disclosure.

In one example of the disclosure, in the polyethylene glycol-linker conjugate, the X is selected from one or a combination of several of —(CH$_2$)$_a$—, —(CH$_2$)$_a$CO—, —(CH$_2$)$_a$NHCO—, —NH(CH$_2$)$_a$CO—, —O(CH$_2$)$_a$—, —O(CH$_2$)$_a$CO— and —O(CH$_2$)$_a$NHCO—, and preferably —(CH$_2$)$_a$—, —(CH$_2$)$_a$CO— or —(CH$_2$)$_a$NHCO—.

Preferably, in the polyethylene glycol-linker conjugate, a is an integer of 0 to 5, for example, 0, 1, 2, 3, 4 or 5.

In one example of the disclosure, in the polyethylene glycol-linker conjugate, the X is a single bond, —CH$_2$—, —CH$_2$CH$_2$—, —CO—, —CH$_2$CO— or —NHCO—.

Preferably, in the polyethylene glycol-linker conjugate, the PEG is a linear-chain, Y-type, multi-branched polyethylene glycol residue, for example, including monomethoxy polyethylene glycol (mPEG), linear-chain double-ended PEG, Y-type PEG, 4-arm branched PEG, 6-arm branched PEG or 8-arm branched PEG, etc.

In one specific example of the disclosure, in the polyethylene glycol-linker conjugate, the PEG is a linear-chain polyethylene glycol residue having a structure of general formula III or IV:

(III)

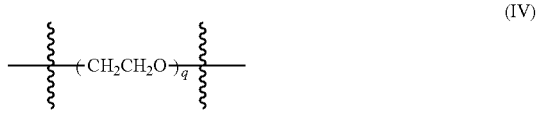
(IV)

wherein, p and q are independently selected from an integer of 1 to 960, and preferably an integer of 1 to 480.

In one specific example of the disclosure, in the polyethylene glycol-linker conjugate, the PEG is a Y-type polyethylene glycol residue having a structure of general formula V or VI:

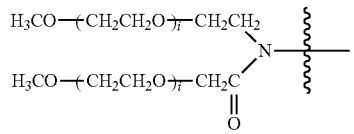
(V)

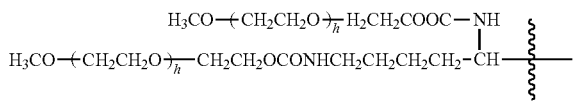
(VI)

wherein, i and h are independently selected from an integer of 1 to 480, and preferably an integer of 1 to 240.

In one specific example of the disclosure, in the polyethylene glycol-linker conjugate, the PEG is a multi-branched polyethylene glycol residue having a structure of general formula VII:

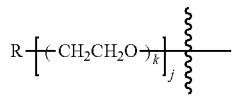
(VII)

wherein, k is an integer of 1 to 320, and preferably an integer of 1 to 240, j is an integer of 3 to 8, and R is a core molecule of multi-branched polyethylene glycol, and R is selected from residues of pentaerythritol, oligomerized pentaerythritol, methyl glucoside, sucrose, diglycol, propylene glycol, glycerol and polyglycerol; and preferably, R is selected from residues of glycerine, hexaglycerol, pentaerythritol, dimeric pentaerythritol and trimeric pentaerythritol.

Preferably, the multi-branched polyethylene glycol residue contains only one linkable site having a structure as follows:

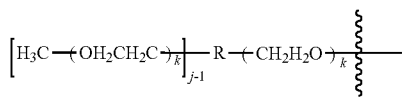
(VII-1)

In one example of the disclosure, the multi-branched polyethylene glycol residue has a structure as follows:

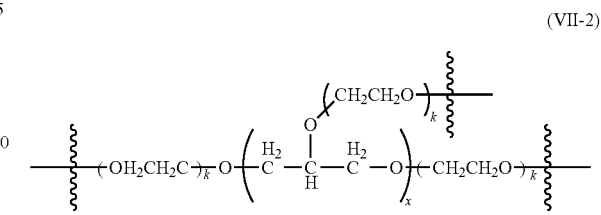
(VII-2)

wherein, k is an integer of 1 to 320, and preferably an integer of 1 to 240, and x is an integer of 1 to 10 (specifically for example, 1, 2, 3, 4, 5, 6, 7, 8, 9 or 10), and preferably an integer of 1 to 6.

In another example of the disclosure, the multi-branched polyethylene glycol residue has a structure as follows:

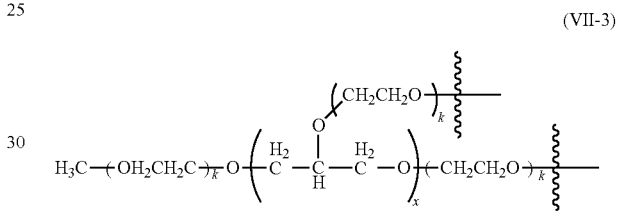
(VII-3)

wherein, k is an integer of 1 to 320, and preferably an integer of 1 to 240, and x is an integer of 1 to 10 (specifically for example, 1, 2, 3, 4, 5, 6, 7, 8, 9 or 10), and preferably an integer of 1 to 6.

In another example of the disclosure, the multi-branched polyethylene glycol residue has a structure as follows:

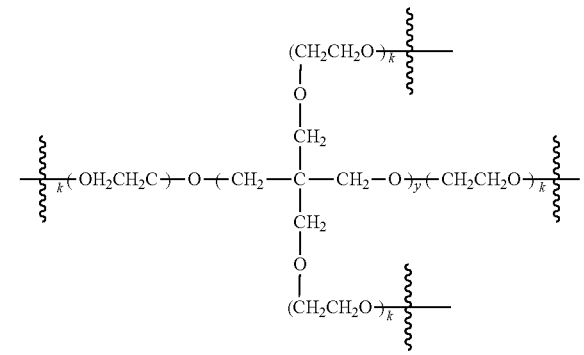
(VII-4)

wherein, k is an integer of 1 to 320, preferably an integer of 1 to 240, and more preferably an integer of 1 to 120, and y is an integer of 1 to 10 (specifically for example, 1, 2, 3, 4, 5, 6, 7, 8, 9 or 10), preferably an integer of 1 to 5, and more preferably an integer of 1 to 3.

In another example of the disclosure, the multi-branched polyethylene glycol residue has a structure as follows:

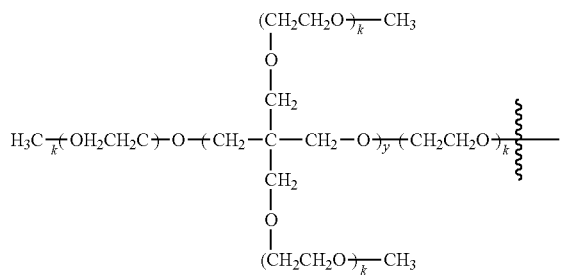

(VII-5)

wherein, k is an integer of 1 to 320, preferably an integer of 1 to 240, and more preferably an integer of 1 to 120, and y is an integer of 1 to 10 (specifically for example, 1, 2, 3, 4, 5, 6, 7, 8, 9 or 10), preferably an integer of 1 to 5, and more preferably an integer of 1 to 3.

In the disclosure, a molecular weight of the PEG may be 1 to 100 KDa, for example, 1 to 10 KDa (specifically 1, 2, 3, 4, 5, 6, 7, 8, 9 and 10 KDa), 10 to 50 KDa (specifically 10, 15, 20, 25, 30, 35, 40, 45 and 50 KDa), and 50 to 100 KDa (specifically 50, 55, 60, 65, 70, 75, 80, 85, 90, 95, and 100 KDa) etc.; and further preferably 10 to 50 KDa.

In one example of the disclosure, the polyethylene glycol-linker conjugate is selected from a structure as follows:

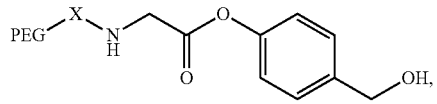

(II-a)

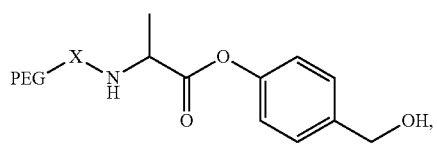

(II-b)

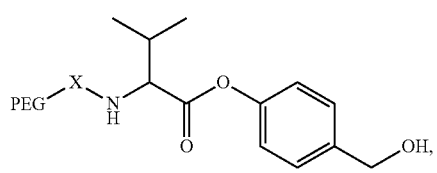

(II-c)

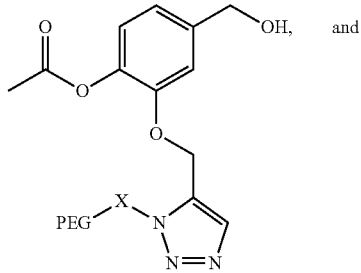

(II-d)

and

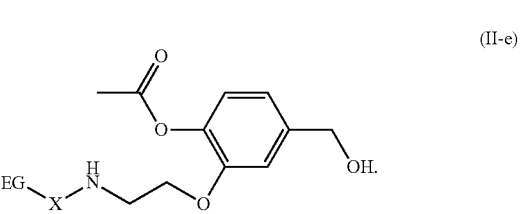

(II-e)

In the above formulae II-a to II-e, the PEG and X have the above definitions of the disclosure.

In one example of the disclosure, in the above formulae II-a to II-e, the PEG has a structure of the above general formula III, V, VI, VII-3 or VII-5 of the disclosure; and in one example of the disclosure, in the above formulae II-a to II-e, a molecular weight of the PEG is 10 to 50 KDa (specifically 10, 15, 20, 25, 30, 35, 40, 45 or 50 KDa).

In one example of the disclosure, in the above formulae II-a to II-e, the X is —CH$_2$CO—, —CO—, —CH$_2$— or —CH$_2$CH$_2$—.

The PEG described herein may be a PEG structure with a linkable site shown in the general formula III, V or VI, which is linked with a linker. For example, the PEG has a structure shown in the general formula III, and when X is —CO—, the structure of II-d is

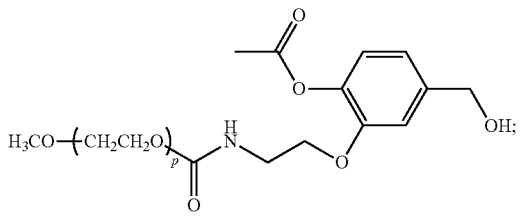

the PEG may also be a PEG with more than two linkable sites shown in the general formula IV or VII, which can be linked with the linker through one or more linking sites. In one example of the disclosure, when the PEG is a PEG with more than two linkable sites as shown in the general formula IV or VII, which can be connected with a linker through one linkable site, and other linkable sites can be linked with an end capping group (e.g., methoxy), or can be linked with the linker through multiple linkable sites, such as the structure shown in the general formula VII-1; specifically, when the PEG is 8-arm polyethylene glycol, and X is —CH$_2$CO—, the structure of II-d may be:

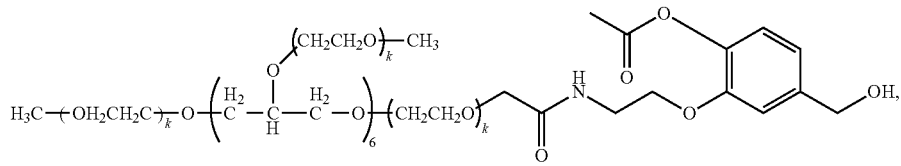

and may also be

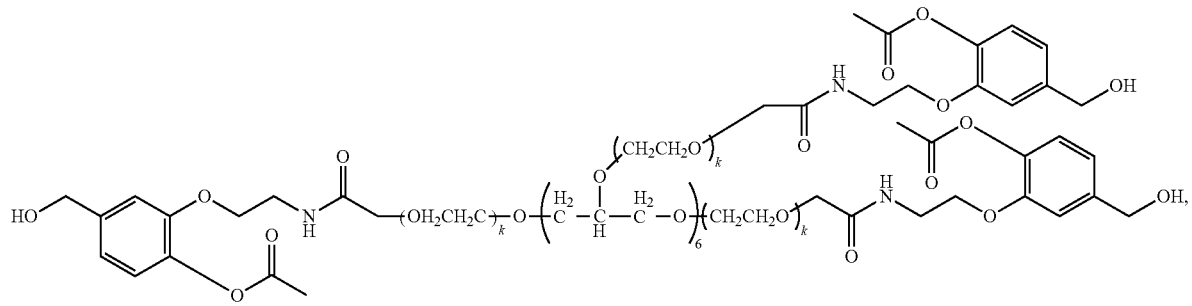

etc.

Preferably, in the above formulae II-a to II-e, the PEG has the structure of the above III, IV, V, VI, VII-2, VII-3, VII-4 or VII-5 of the disclosure, wherein x is preferably an integer of 1 to 6, and y is preferably an integer of 1 to 3.

Another aspect of the disclosure also provides a polyethylene glycol-linker conjugate derivative, which has a structure as follows:

PEG-X-L-P-Q  (VIII)

wherein, L is the above linker of the disclosure,

PEG is a polyethylene glycol residue,

X is a linking group of PEG and L, which is selected from one or a combination of several of —$(CH_2)_a$—, —$(CH_2)_a CO$—, —$(CH_2)_a OCO$—, —$(CH_2)_a NHCO$—, —$NH(CH_2)_a CO$—, —$(CH_2)_a SO_2$—, —$O(CH_2)_a$—, —$O(CH_2)_a CO$—, —$O(CH_2)_a OCO$—, —$O(CH_2)_a NHCO$— and —$O(CH_2)_a SO_2$—, and a is an integer of 0 to 10, P is a linking group of L and an end capping group Q, which is selected from one or a combination of several of —$(CH_2)_r$—,

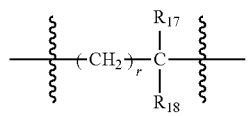

—$(CH_2)_r O$—, —$(CH_2)_r CO$—, —$(CH_2)_r NH$—, —$(CH_2)_r CONH$—, —$(CH_2)_r NHCO$—, —$(CH_2)_r SH$—,

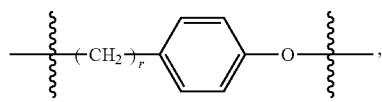

-continued

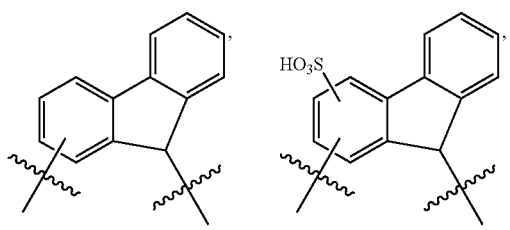

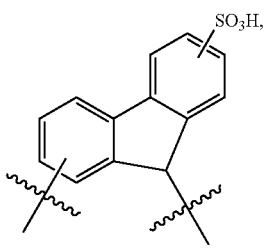

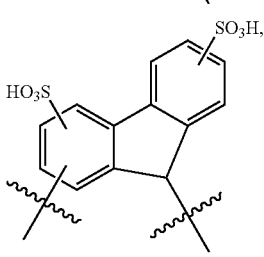

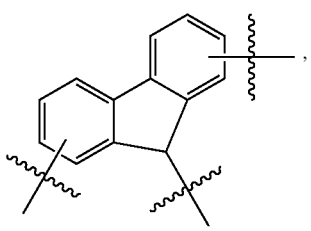

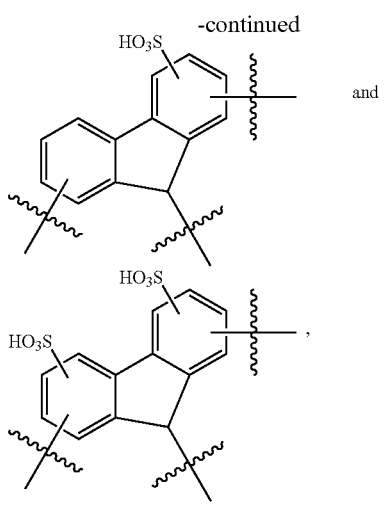

and r is an integer of 0 to 10,

Q is an end capping group selected from C1-C6 alkoxy, hydroxyl, amino, carboxyl, mercapto, ester group, ketone group, aldehyde group, o-dithiopyridyl, azido, hydrazide, alkynyl, silicyl, maleimide group and succinimido, and $R_{17}$ and $R_{18}$ are independently selected from —H, C1-6 alkyl, C1-6 alkoxy, C3-6 cycloalkyl and C4-10 alkylene cycloalkyl.

In one example of the disclosure, the derivative have structures as follows:

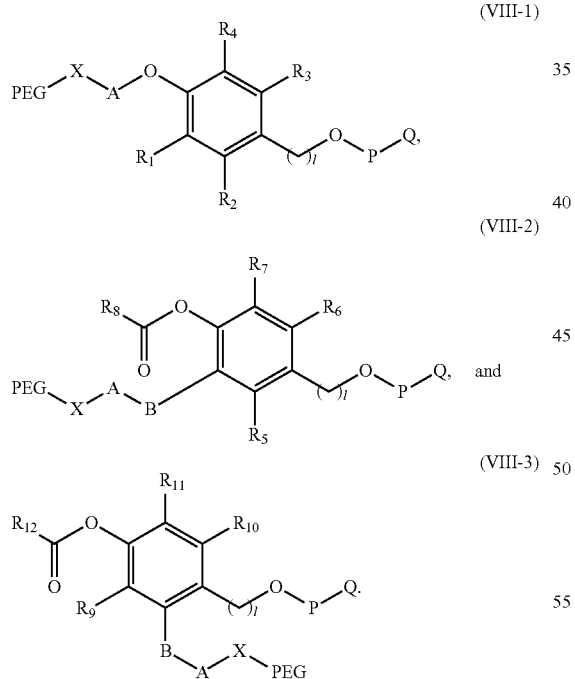

In the above formulae VIII-1 to VIII-3, $R_{1-12}$, l, A, B, X, PEG and the like have the above corresponding definitions of the disclosure.

In one example of the disclosure, X is a single bond, —CH$_2$—, —CH$_2$CH$_2$—, —CO—, —CH$_2$CO— or —NHCO—.

Preferably, $R_{17}$ and $R_{18}$ are independently selected from —H, —CH$_3$, —CH$_2$CH$_3$, —CH$_2$CH$_2$CH$_3$, —OCH$_3$, —OCH$_2$CH$_3$ and —OCH$_2$CH$_2$CH$_3$, and more preferably selected from —H, —CH$_3$, —OCH$_3$ and —OCH$_2$CH$_3$; in one example of the disclosure, $R_{17}$ is H, and $R_{18}$ is —CH$_3$, —OCH$_3$ or —OCH$_2$CH$_3$; in one preferred example of the disclosure, $R_{17}$ is H, and $R_{18}$ is —CH$_3$.

In one example of the disclosure, P is selected from one or a combination of several of —(CH$_2$)$_r$—, —(CH$_2$)$_r$CH(CH$_3$)—, —(CH$_2$)$_r$O—, —(CH$_2$)$_r$CO—, —(CH$_2$)$_r$NH—, —(CH$_2$)$_r$CONH—, —(CH$_2$)$_r$NHCO—, —(CH$_2$)$_r$SH—,

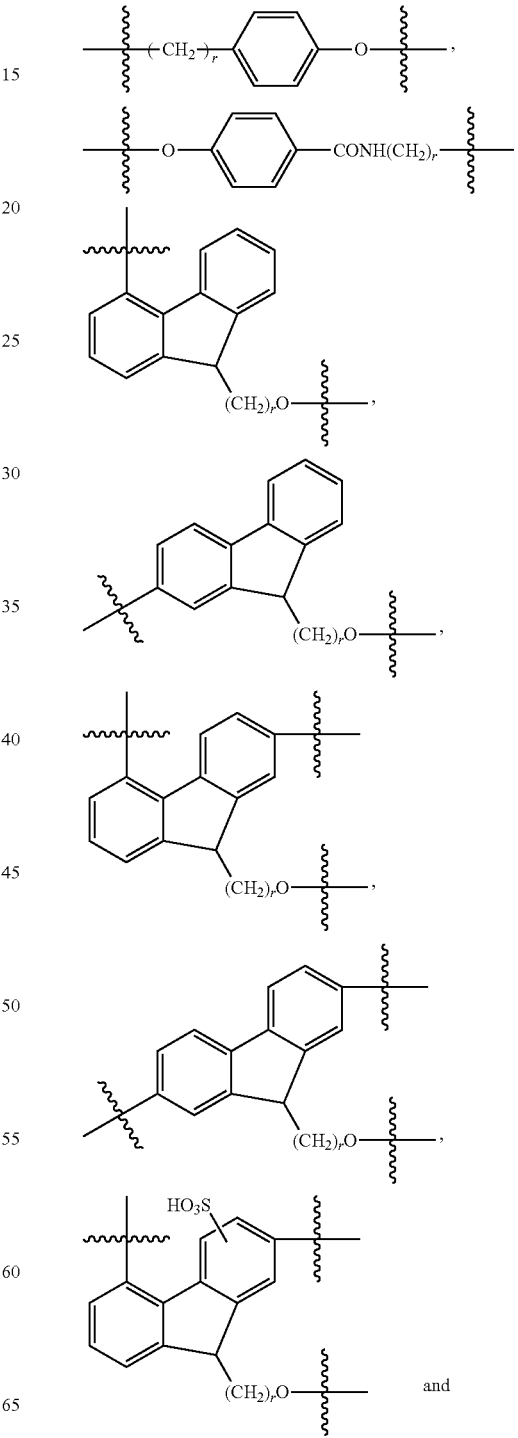

-continued

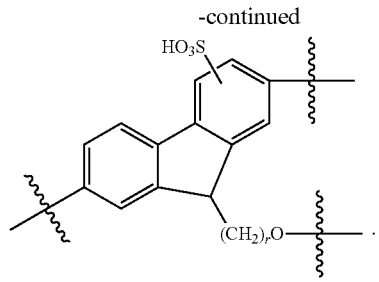

Preferably, r is an integer of 0 to 5, for example, 0, 1, 2, 3, 4 or 5.

In one specific example of the disclosure, the P is selected from one or a combination of several of a single bond, —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH(CH$_3$)—, —CH$_2$CH(CH$_3$)—, —CH$_2$CH$_2$CH(CH$_3$)—, —CH$_2$CH$_2$CH$_2$CH(CH$_3$)—, —CH$_2$CH$_2$CH$_2$CH$_2$CH(CH$_3$)—, —CH$_2$CH$_2$CH$_2$CH$_2$CH$_2$CH(CH$_3$)—, —(CH$_2$)$_r$O—, —(CH$_2$)$_r$CO—, —(CH$_2$)$_r$NH—, —(CH$_2$)$_r$CONH—, —(CH$_2$)$_r$NHCO—, —(CH$_2$)$_r$SH—,

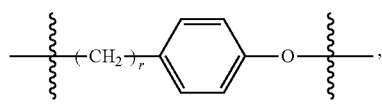

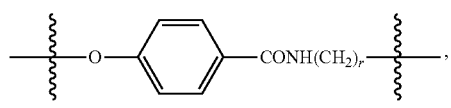

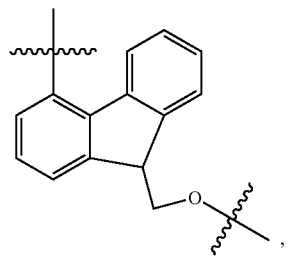

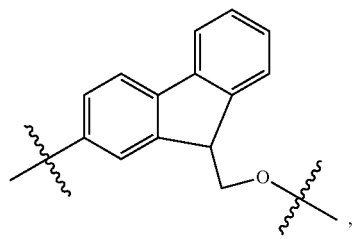

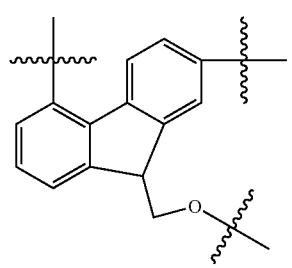

-continued

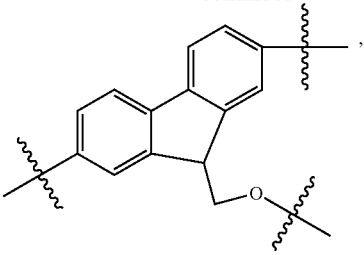

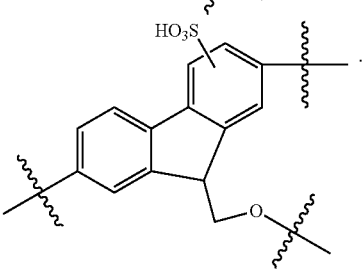

In the disclosure, when P has more than two linking sites, more than one PEG-X-L- and more than one Q can be linked; for example, when P is

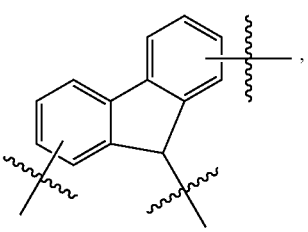

the above derivative may be

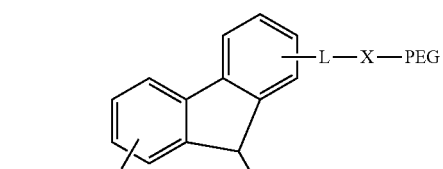

or

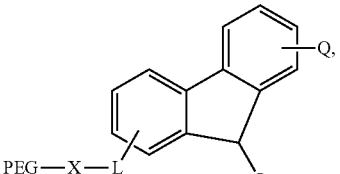

etc.

In one example of the disclosure, Q is an ester group or a ketone group.

In one specific example of the disclosure, in Q, the ester group is selected from

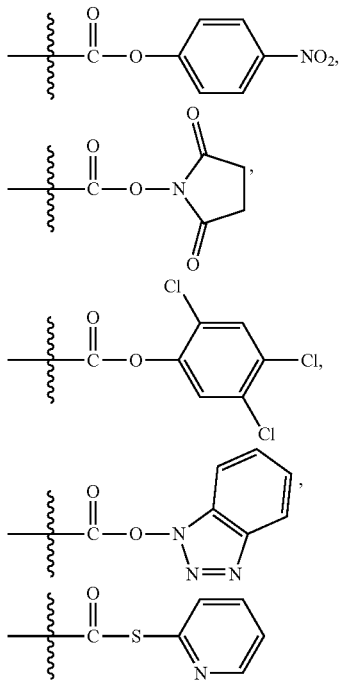

and —SO$_2$CH$_2$CF$_3$.

In another specific example of the disclosure, in Q, the ketone group is selected from

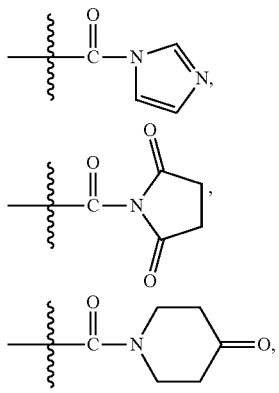

—COCH$_3$ and —COCH$_2$CH$_3$.

In a preferred example of the disclosure, the Q is

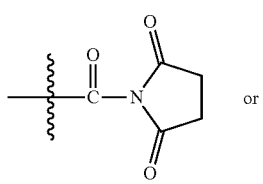 or

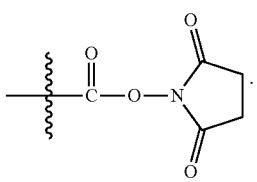

In one example of the disclosure, the derivative have structures as follows:

(VIII-1-1)

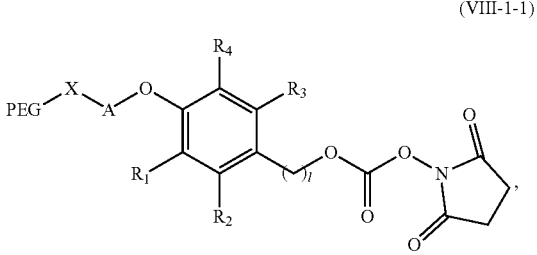

(VIII-2-1)

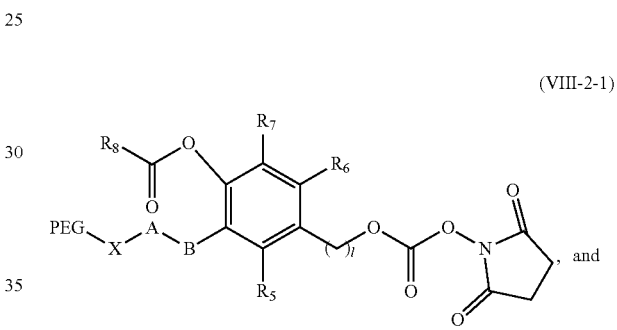

and (VIII-3-1)

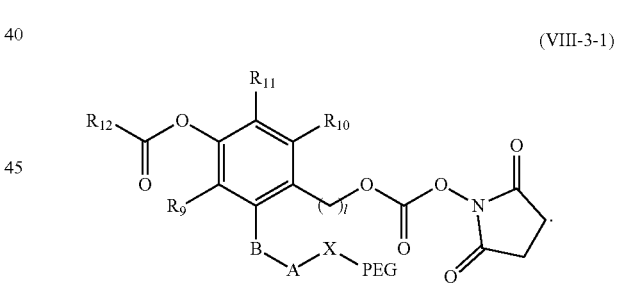

In the above formulae VIII-1 to VIII-3, R$_{1-12}$, l, A, B, X, PEG and the like have the above corresponding definitions of the disclosure.

In one example of the disclosure, the derivative is selected from a structure as follows:

(VIII-a)

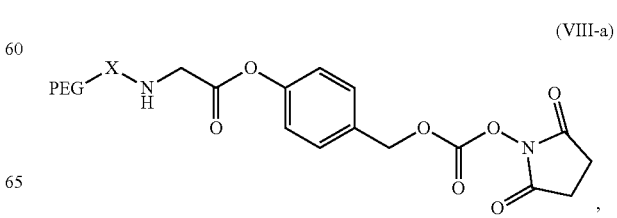

-continued (VIII-b)

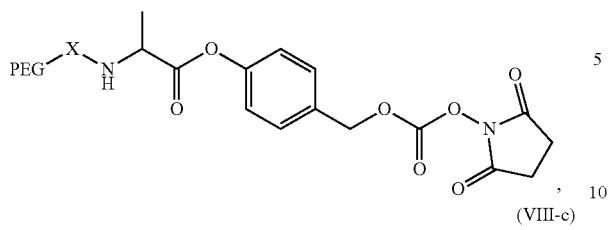

(VIII-c)

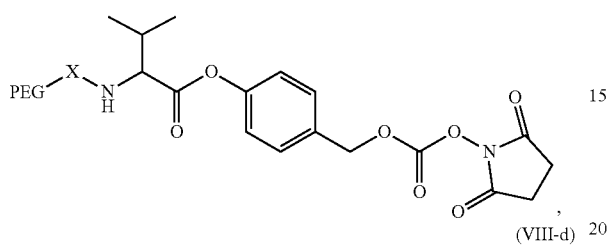

(VIII-d)

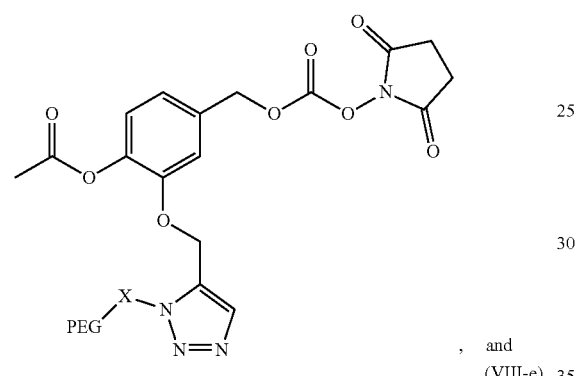

, and (VIII-e)

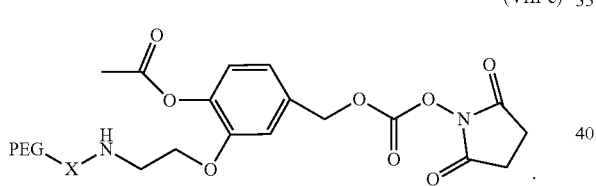

In the above formulae VIII-a to VIII-e, the PEG and X have the above definitions of the disclosure.

In one example of the disclosure, in the above formulae VIII-a to VIII-e, the PEG has a structure of the above general formula III, IV, V, VI, VII-2, VII-3, VII-4 or VII-5 of the disclosure.

In one example of the disclosure, in the above formulae VIII-a to VIII-e, a molecular weight of the PEG is 10 to 50 KDa (specifically 10, 15, 20, 25, 30, 35, 40, 45 or 50 KDa).

In one example of the disclosure, in the above formulae VIII-a to VIII-e, the X is —CH$_2$CO—, —CO—, —CH$_2$— or —CH$_2$CH$_2$—.

Preferably, in the above formulae VIII-a to VIII-e, the PEG has the structure of the above III, IV, V, VI, VII-2, VII-3, VII-4 or VII-5 of the disclosure, wherein x is an integer of 1 to 6, and y is an integer of 1 to 3.

Another aspect of the disclosure also provides a polyethylene glycol-linker-drug conjugate, which has a structure as follows:

(PEG-X-L-Y)$_n$-D     (IX)

wherein, PEG is a polyethylene glycol residue,

X is a linking group of PEG and L, which is selected from one or a combination of several of —(CH$_2$)$_a$—, —(CH$_2$)$_a$CO—, —(CH$_2$)$_a$OCO—, —(CH$_2$)$_a$NHCO—, —NH(CH$_2$)$_a$CO—, —(CH$_2$)$_a$SO$_2$—, —O(CH$_2$)$_a$—, —O(CH$_2$)$_a$CO—, —O(CH$_2$)$_a$OCO—, —O(CH$_2$)$_a$NHCO— and —O(CH$_2$)$_a$SO$_2$—, and a is an integer of 0 to 10, Y is a linking group of L and D, which is selected from one or a combination of several of —(CH$_2$)$_r$—,

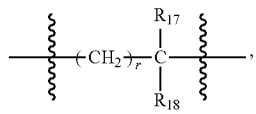

—(CH$_2$)$_r$O—, —(CH$_2$)$_r$CO—, —(CH$_2$)$_r$NH—, —(CH$_2$)$_r$CONH—, —(CH$_2$)$_r$NHCO—, —(CH$_2$)$_r$SH—,

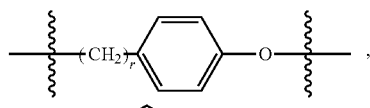

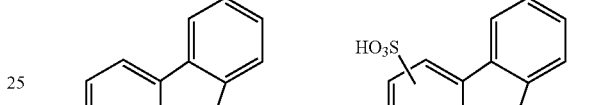

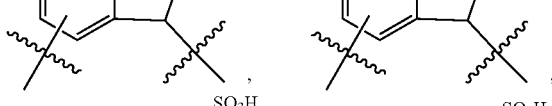

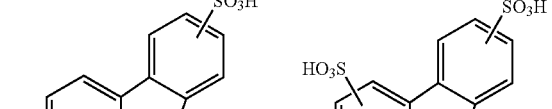

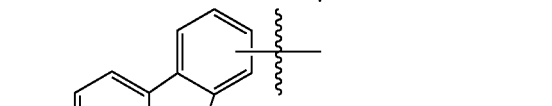

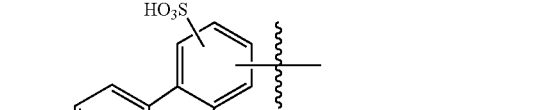

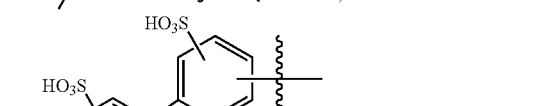

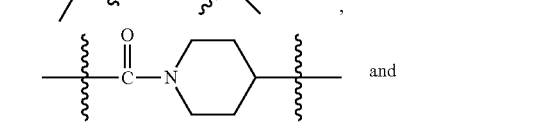

and and r is an integer of 0 to 10, $R_{17}$ and $R_{18}$ are independently selected from —H, C1-6 alkyl, C1-6 alkoxy, C3-6 cycloalkyl and C4-10 alkylene cycloalkyl, L is the above linker of the disclosure, D is a bioactive agent containing m amido groups, and m is an integer of 1 to 500, and n is an integer, and $1 \leq n \leq m$.

In one example of the disclosure, when n=1, the general formula IX at the moment is PEG-X-L-Y-D.

In one example of the disclosure, the D is a micromolecular biological active agent containing amido group and a pharmaceutically acceptable salt thereof, and preferably includes adriamycin, crizotinib, goserelin, cytarabine, procaine, benzocaine, chloroprocaine, dimethocaine, dopamine, norepinephrine, clenbuterol, phenformin, daraprim, prosultiamine, p-aminosalicylic acid, sulfadiazine, and derivatives thereof.

In one specific example of the disclosure, the D is adriamycin or a derivative thereof, which has a structure as follows:

(X)

wherein, $W_1$ is selected from —H, —OH, —OCH$_3$ and —OCH$_2$CH$_3$; preferably —H or —OCH$_3$, and more preferably —OCH$_3$;

$W_2$ is selected from —H, —OH, —OCO(CH$_2$)$_5$COOH and —OCO(CH$_2$)$_2$NH$_2$; preferably —H or —OH, and more preferably —OH; and $W_3$ is selected from —OH, —OCH$_3$ and and preferably —OH.

In one example of the disclosure, the D is adriamycin, which has a structure as follows:

(X-1)

In another example of the disclosure, D is a macromolecular biological active agent containing an amino group, such as polypeptide and protein drugs, for example, the polypeptide and protein drugs are cytokines (such as interleukin, colony stimulating factors, interferon, growth factors, tumor necrosis factors, transforming growth factor-beta family or chemokine family, etc.), human hemoglobin, coagulation factors, vascular endothelial growth factor antibody antagonists, protein hormones (such as insulin, glucagon, calcitonin, hypothalamic hormones, pituitary hormones or gastrointestinal hormones, etc.), antibodies (such as monoclonal antibodies, polyclonal antibodies, dimers, multimers, multispecific antibodies or antibody fragments), enzymes and coenzyme drugs (phenylalanine ammonia lyase, arginase, arginine deacylase, pancreatic ribonuclease, superoxide dismutase, asparaginase, glucocerebrosidase or hyaluronidase).

In the drug conjugate, drug molecules are linked with a polyethylene glycol-linker through an amine group, and the amine group may be an N-terminal amino group of a peptide chain and/or a side chain amino group of an amino acid residue (such as lysine and the like) in the peptide chain; more preferably, in the drug conjugate, the polyethylene glycol-linker is linked through formed by reaction of an active carbonate group with a primary amine group of the drug molecule.

In this application, the term "antibody" is used in a broadest meaning thereof and specifically covers the monoclonal antibody, the polyclonal antibody, the dimer, the multimer, the multispecific antibody (e.g., bispecific antibody) and the antibody fragments as long as desired bioactivity (Miller et al. (2003) Jour. of Immunology, 170: 4854-4861) is exhibited by the antibody. The antibody may be mouse, human, humanized, chimeric antibody or derived from other species. The antibody may have any type (e.g., IgG, IgE, IgM, IgD, and IgA) and category (e.g., IgG1, IgG2, IgG3, IgG4, IGG1, and IgA2), wherein IgM contains about 450 free amino groups.

In one example of the disclosure, the D is a cytokine; and in one example of the disclosure, D is an interleukin, preferably an interleukin 2(IL-2), and more preferably a recombinant human interleukin 2(rhIL-2).

In another example of the disclosure, the cytokine is a colony stimulating factor, preferably a granulocyte colony stimulating factor, more preferably a recombinant human granulocyte colony stimulating factor.

In another example of the disclosure, the D is an antibody.

In one example of the disclosure, the antibody is a monoclonal antibody, such as an anti-HER2 monoclonal antibody, and preferably a recombinant anti-HER2 humanized monoclonal antibody.

In another example of the disclosure, the D is a human hemoglobin.

In another example of the disclosure, the D is an enzyme and a coenzyme drug, preferably selected from pancreatic ribonuclease, superoxide dismutase and asparaginase.

In another example of the disclosure, the D is a protein hormone, and preferably insulin.

In the polyethylene glycol-linker-drug conjugate, n is an integer of 1 to 500 (for example, 1, 2, 3, 4, 5, 6, 7, 8, 9, 10, 11, 12, 13, 14, 15, 20, 30, 40, 50, 60, 70, 80, 90, 100, 150, 200, 250, 300, 350, 400, 450 or 500), and when the drug is interleukin 2, n may be 1, 2, 3, 4, 5, 6, 7, 8, 9, 10, 11 or 12; when the drug is a recombinant anti-HER2 humanized monoclonal antibody, n may be an integer of 1 to 90; and when the drug is IgM, n may be an integer of 1 to 450.

In one example of the disclosure, Y is selected from one or a combination of several of —$(CH_2)_r$—, —$(CH_2)_r CH(CH_3)$—, —$(CH_2)_r O$—, —$(CH_2)_r CO$—, —$(CH_2)_r NH$—, —$(CH_2)_r CONH$—, —$(CH_2)_r NHCO$—, —$(CH_2)_r SH$—,

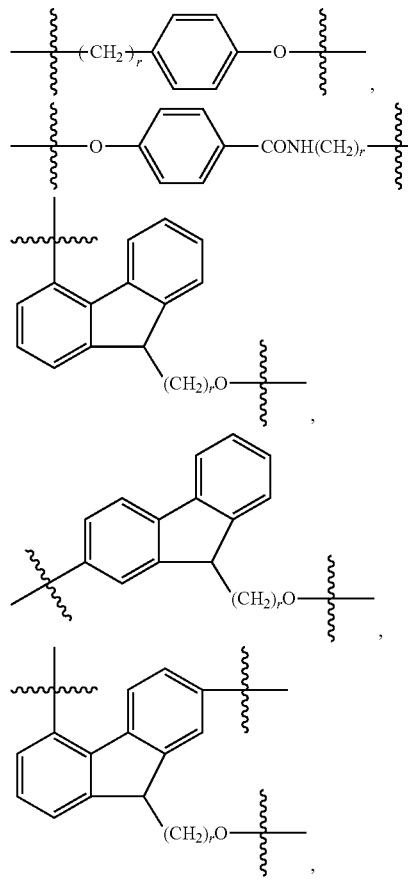

-continued

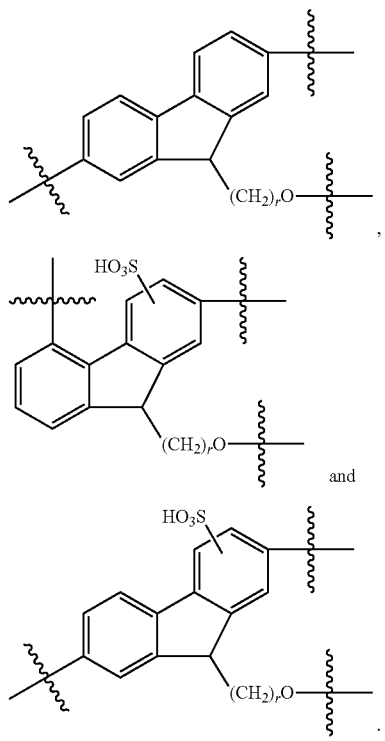

Preferably, r is an integer of 0 to 5, for example, 0, 1, 2, 3, 4 or 5.

In one specific example of the disclosure, the Y is selected from one or a combination of several of a single bond, —$CH_2$—, —$CH_2CH_2$—, —$CH_2CH_2CH_2$—, —$CH_2CH_2CH_2CH_2$—, —$CH_2CH_2CH_2CH_2CH_2$—, —$CH(CH_3)$—, —$CH_2CH(CH_3)$—, —$CH_2CH_2CH(CH_3)$—, —$CH_2CH_2CH_2CH(CH_3)$—, —$CH_2CH_2CH_2CH_2CH(CH_3)$—, —$CH_2CH_2CH_2CH_2CH_2CH(CH_3)$—, —$(CH_2)_r O$—, —$(CH_2)_r CO$—, —$(CH_2)_r CONH$—, —$(CH_2)_r NH$—, —$(CH_2)_r SH$—,

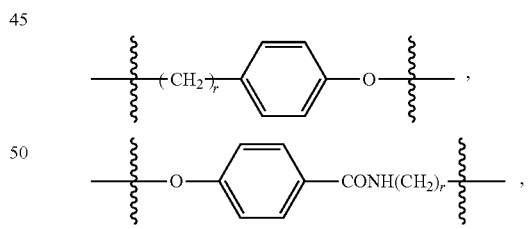

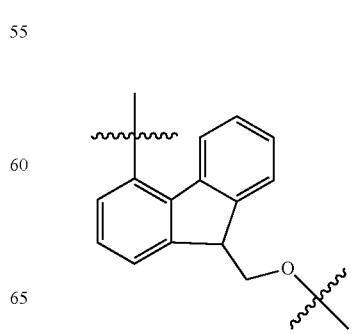

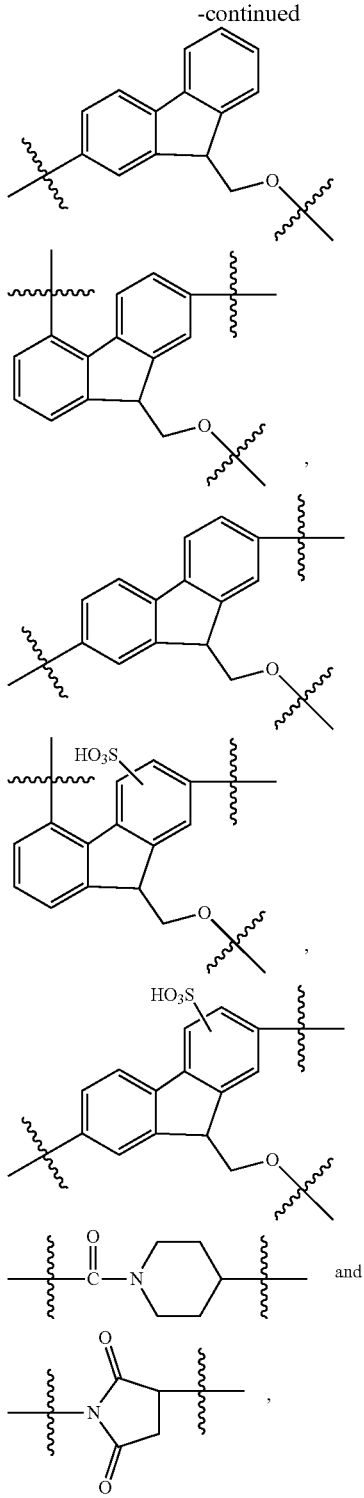

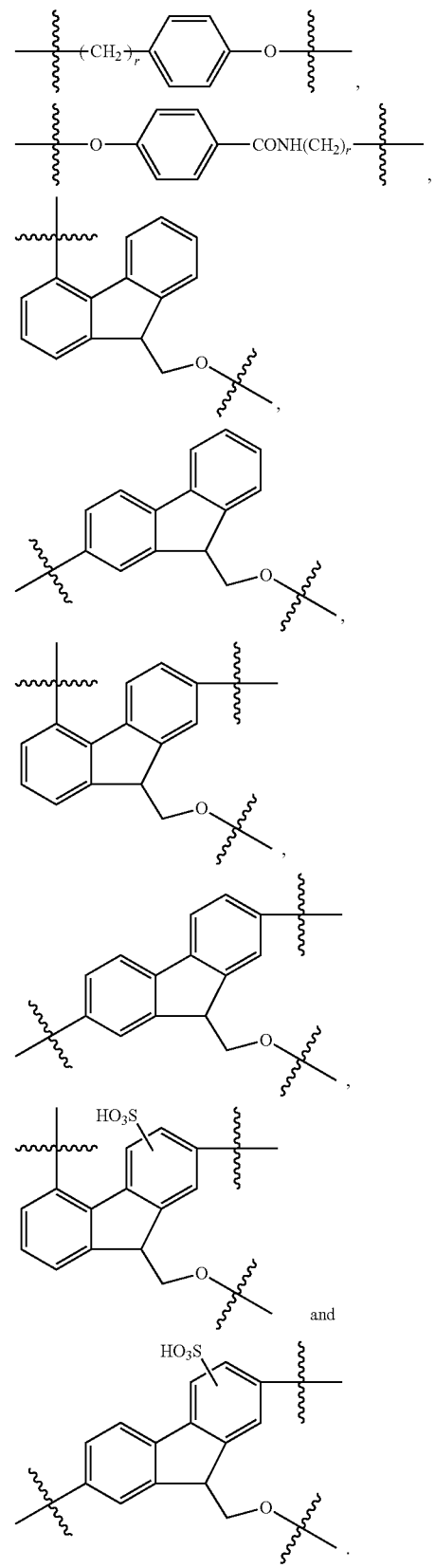

In another specific example of the disclosure, Y is a combination of —(CH$_2$)$_r$CO— and one or several of a single bond, —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH(CH$_3$)—, —CH$_2$CH(CH$_3$)—, —CH$_2$CH$_2$CH(CH$_3$)—, —CH$_2$CH$_2$CH$_2$CH(CH$_3$)—, —CH$_2$CH$_2$CH$_2$CH$_2$CH(CH$_3$)—, —CH$_2$CH$_2$CH$_2$CH$_2$CH$_2$CH(CH$_3$)—, —(CH$_2$)$_r$O—, —(CH$_2$)$_r$CONH—, —(CH$_2$)$_r$NHCO—, —(CH$_2$)$_r$NH—, —(CH$_2$)$_r$SH—, In one example of the disclosure, in the polyethylene glycol-linker-drug conjugate, Y is —(CH$_2$)$_r$CO—.

In another example of the disclosure, in the polyethylene glycol-linker-drug conjugate, Y is —CO—.

In the disclosure, when the Y has more than two linking sites, more than one PEG-X-L- and D can be linked; for example, when Y is

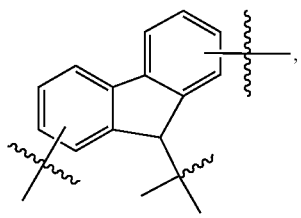

the polyethylene glycol-linker-drug conjugate may be

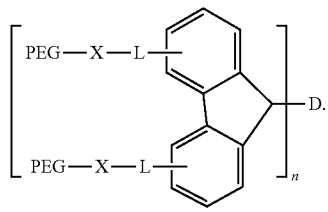

In one example of the disclosure, the polyethylene glycol-linker-drug conjugate have structures as follows:

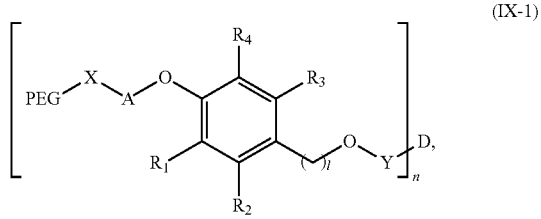

(IX-1)

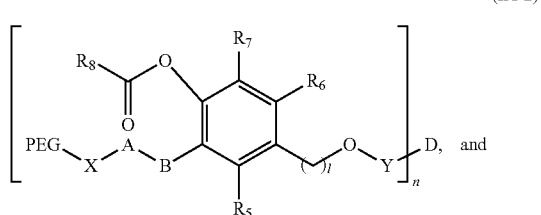

(IX-2)

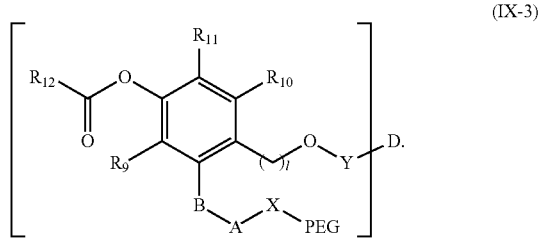

(IX-3)

In the above formulae IX-1 to IX-3, $R_{1-12}$, l, A, B, X, PEG, Y, D and the like have the above corresponding definitions of the disclosure.

In one example of the disclosure, in the above formula IX-1, $R_{1-4}$ are all —H.

In one example of the disclosure, in the above formula IX-2, $R_{5-7}$ are all —H.

In one example of the disclosure, in the above formula IX-3, $R_{9-11}$ are all —H.

In one example of the disclosure, in the above formulae IX-2 and IX-3, $R_8$ and/or $R_{12}$ is methyl.

In one example of the disclosure, in the above formulae IX-1 to IX-3, l is 1.

In one example of the disclosure, in the above formula IX-1, A is —COCH$_2$NH—, —COCH(CH$_3$)NH— or —COCH(CH(CH$_3$)$_2$)NH—.

In one example of the disclosure, in the above formulae IX-2 and IX-3, —B-A- is —OCH$_2$CH$_2$NH—.

In one example of the disclosure, in the above formulae IX-1 to IX-3, X is a single bond, —CH$_2$—, —CH$_2$CH$_2$—, —CO—, —CH$_2$CO— or —NHCO—.

In one example of the disclosure, in the above formulae IX-1 to IX-3, D is a polypeptide and protein drug, preferably a cytokine, and more preferably IL-2 (such as rhIL-2), and the PEG has the structure of the above III, V, VI, VII-3 or VII-5 of the disclosure; and preferably, x is an integer of 1 to 6, and y is an integer of 1 to 3.

In one example of the disclosure, in the above formulae IX-1 to IX-3, D is adriamycin or a derivative thereof, and has the structure shown in the above general formula X of the disclosure, and preferably adriamycin, which has the structure shown in the above general formula X-1 of the disclosure, and the PEG has the structure shown in the above III, IV, V, VI, VII-2 or VII-4 of the disclosure; and preferably, x is an integer of 1 to 6, and y is an integer of 1 to 3.

In one example of the disclosure, in the above formulae IX-1 to IX-3, a molecular weight of the PEG is 10 to 50 KDa (specifically 10, 15, 20, 25, 30, 35, 40, 45 or 50 KDa).

In one specific example of the disclosure, the polyethylene glycol-linker-drug conjugate have structures as follows:

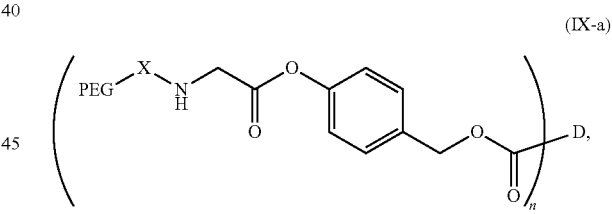

(IX-a)

(IX-b)

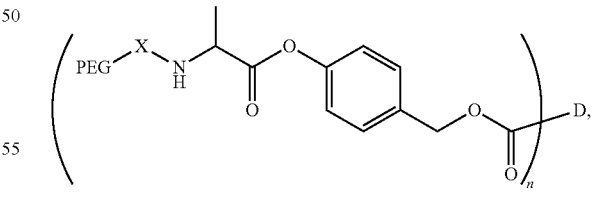

(IX-c)

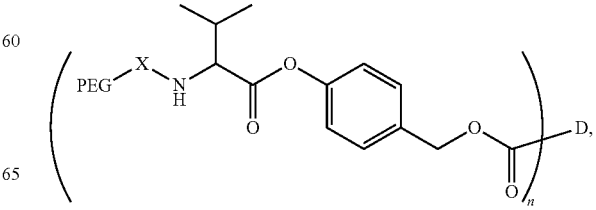

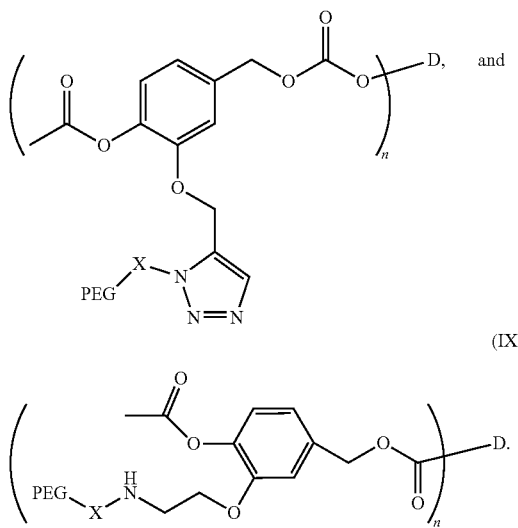

In the above formulae IX-a to IX-e, the PEG, X, n and D have the above definitions of the disclosure.

In one example of the disclosure, in the above formulae IX-a to IX-e, D is a polypeptide and protein drug, preferably a cytokine, and more preferably IL-2 (such rhIL-2), and the PEG has the structure of the above III, V, VI, VII-3 or VII-5 of the disclosure; and preferably, wherein x is an integer of 1 to 6, and y is an integer of 1 to 3. When the PEG has the structure of the general formula V, VI, VII-3 or VII-5, a steric hindrance effect can be increased, and a drug release rate can be regulated and controlled.

In one example of the disclosure, in the above formulae IX-a to IX-e, D is adriamycin or a derivative thereof, which has the structure of the above general formula X of the disclosure; preferably, D is adriamycin, which has the structure of the above general formula X-1 of the disclosure, and n is 1.

In one example of the disclosure, in the above formulae IX-a to IX-e, a molecular weight of the PEG is 10 to 50 KDa (specifically 10, 15, 20, 25, 30, 35, 40, 45 or 50 KDa).

In one example of the disclosure, in the above formulae IX-a to IX-e, X is —CH$_2$CO—, —CO—, —CH$_2$— or —CH$_2$CH$_2$—.

In one example of the disclosure, in the above formulae IX-a to IX-e, D is IL-2 and preferably rhIL-2, n is an integer of 1 to 12 and preferably an integer of 1 to 7, for example, 1, 2, 3, 4, 5, 6, or 7.

In one more specific example of the disclosure, the drug is a polypeptide and protein drug, preferably a cytokine, and more preferably IL-2 (such as rhIL-2), and the polyethylene glycol-linker-IL-2 conjugate have structures as follows:

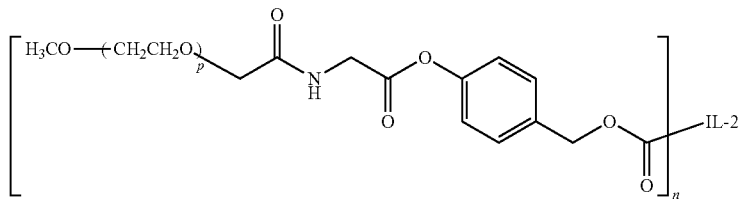

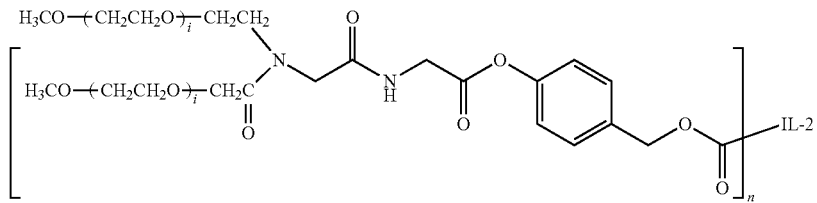

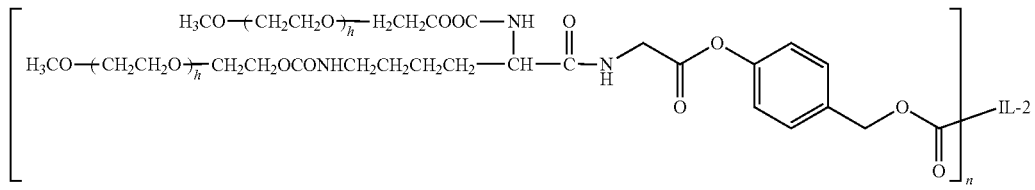

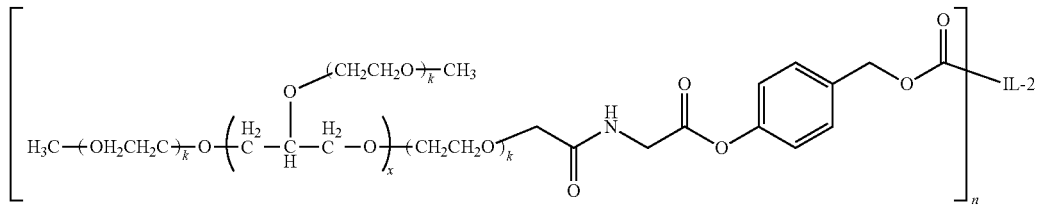

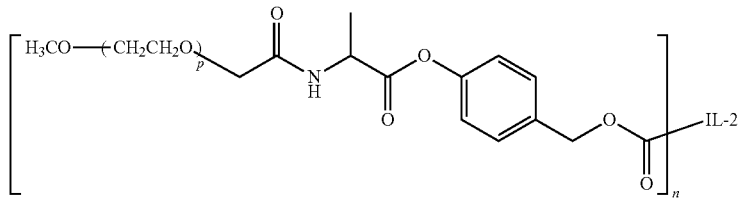
(IX-b-1)
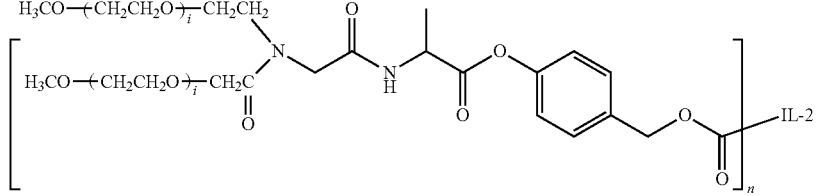
(IX-b-2)
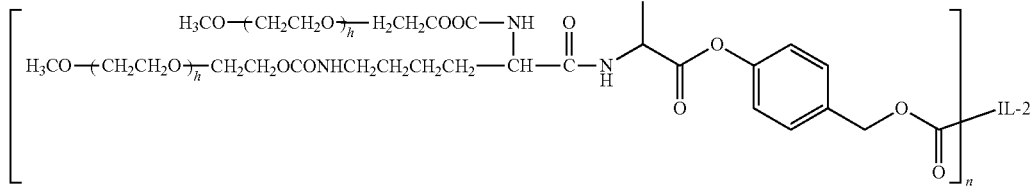
(IX-b-3)
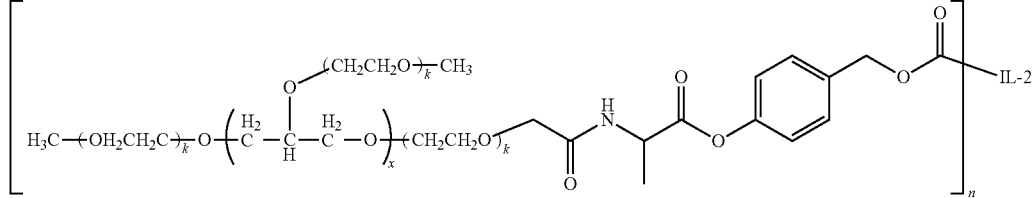
(IX-b-4)
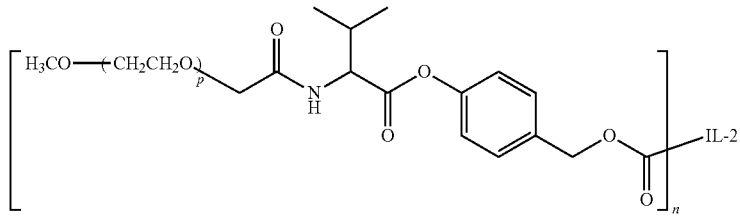
(IX-c-1)
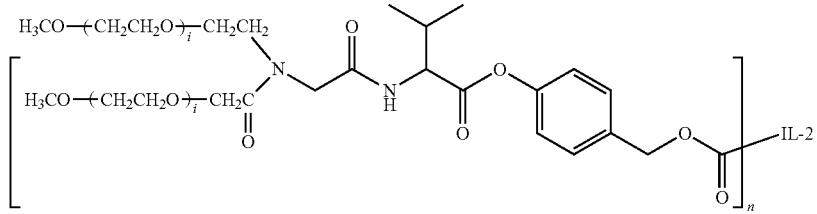
(IX-c-2)
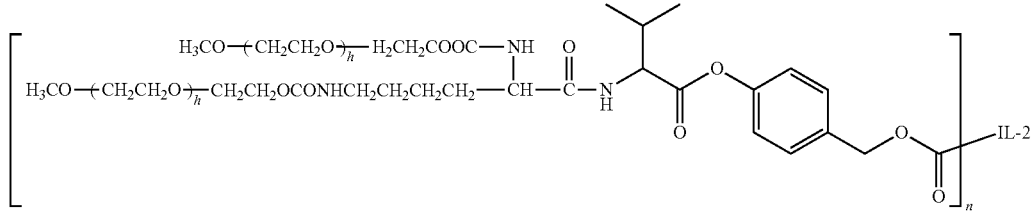
(IX-c-3)

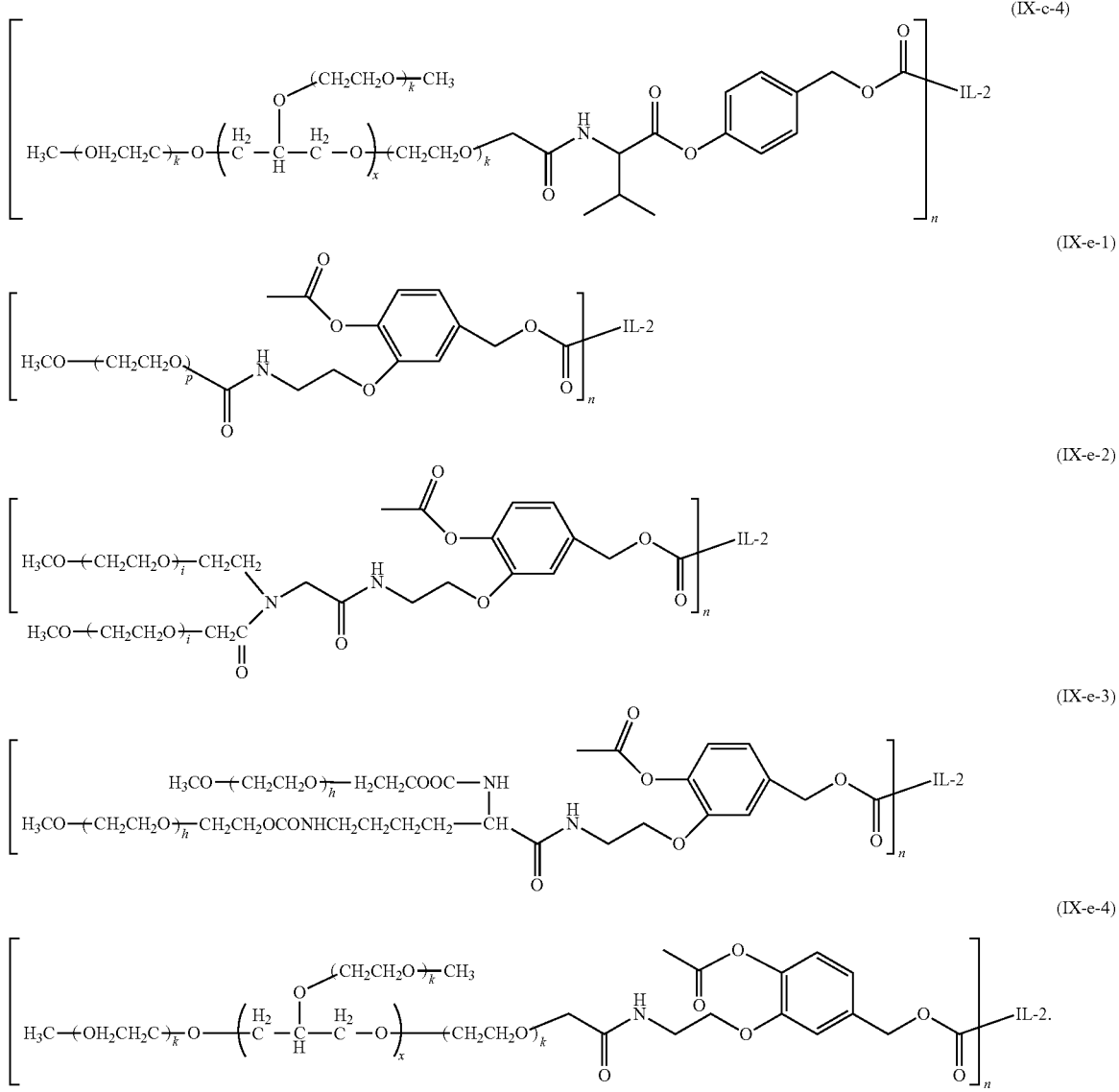

In the above formulae, p, q, i, h, k and x respectively have the definitions in the general formulae III, V, VI and VII-3 of the disclosure.

In one example of the disclosure, x is an integer of 1 to 6, and preferably, x is 6.

In one example of the disclosure, in the above formulae, n is an integer of 1 to 12 and preferably an integer of 1 to 7, for example, 1, 2, 3, 4, 5, 6, or 7.

In one example of the disclosure, in the above formulae, IL-2 is rhIL-2.

In one more specific example of the disclosure, the drug is adriamycin or a derivative thereof, which has the structure of the above general formula X of the disclosure; preferably, D is adriamycin, which has the structure of the above general formula X-1 of the disclosure, and the polyethylene glycol-linker-adriamycin conjugate have structures as follows:

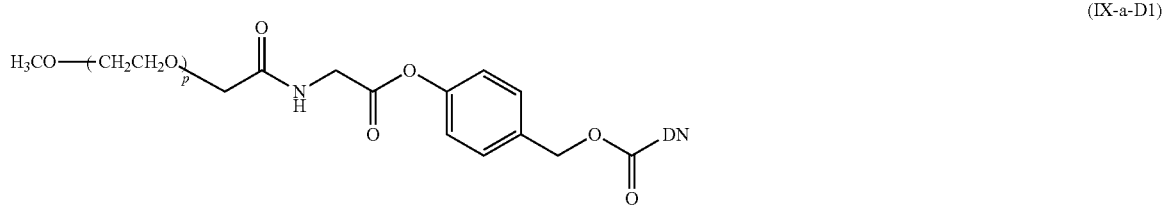

(IX-a-D2)
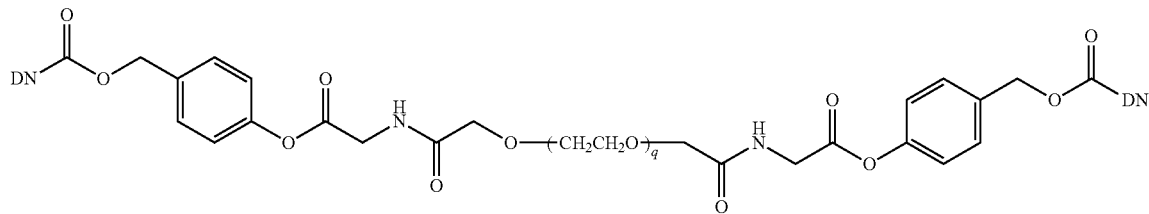
(IX-a-D3)
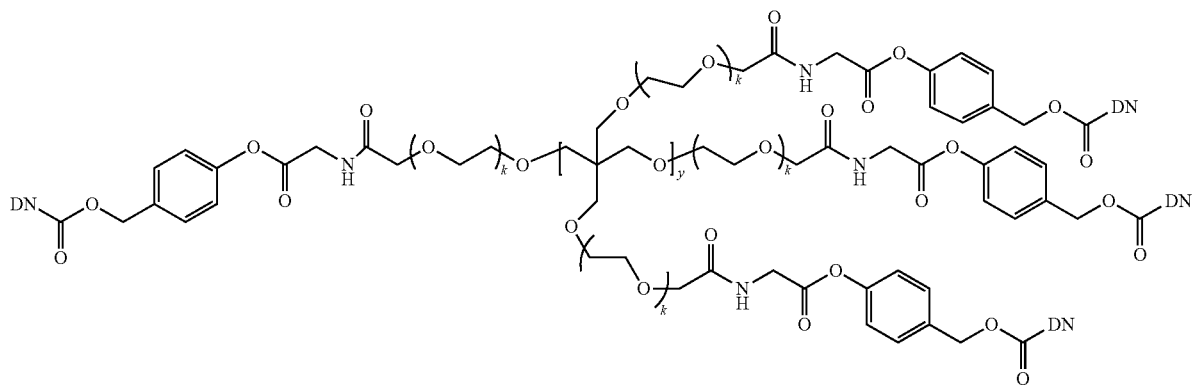
(IX-b-D1)
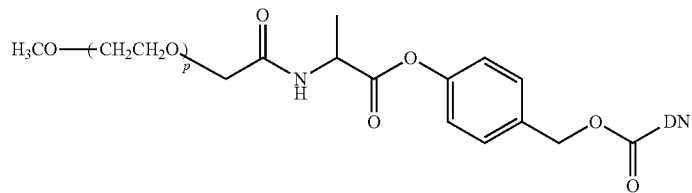
(IX-b-D2)
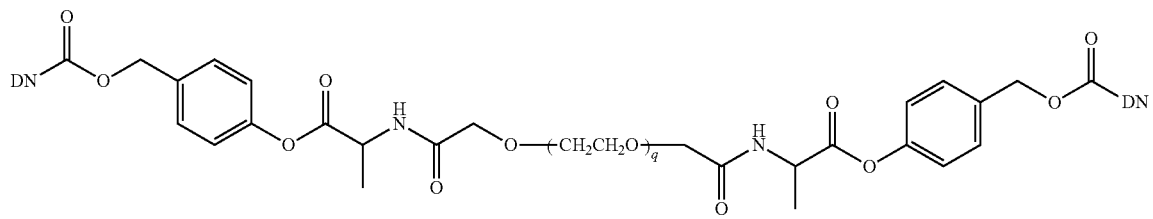
(IX-b-D3)
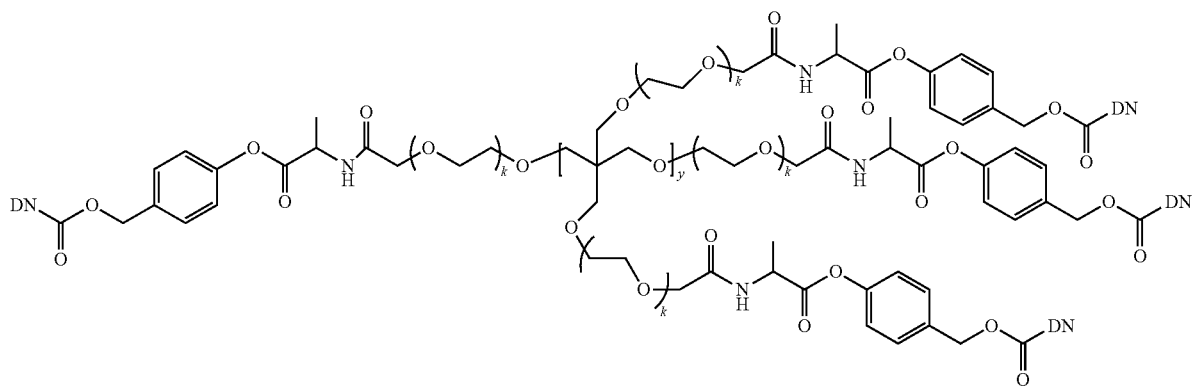

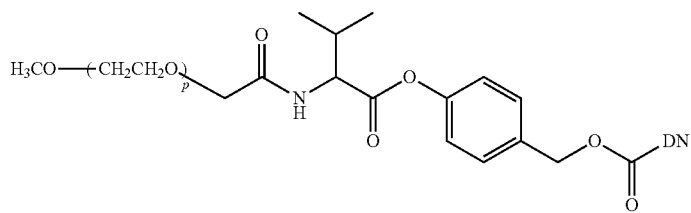
(IX-c-D1)
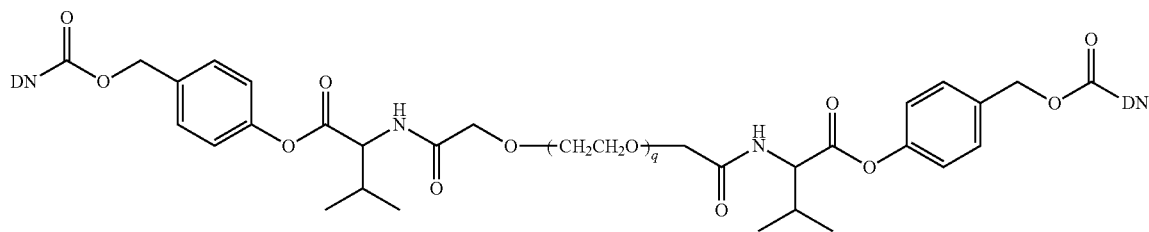
(IX-c-D2)
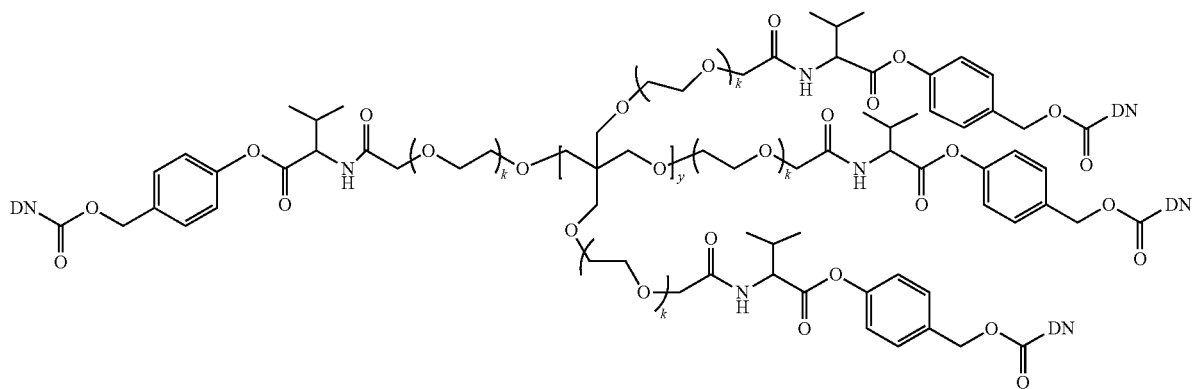
(IX-c-D3)
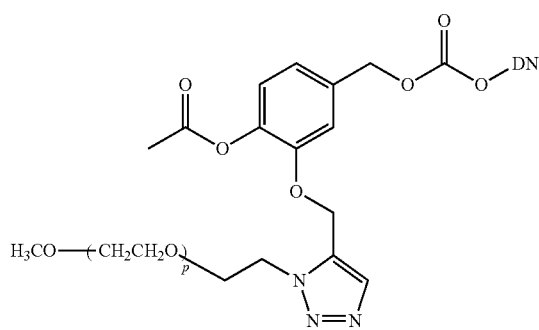
(IX-d-D1)

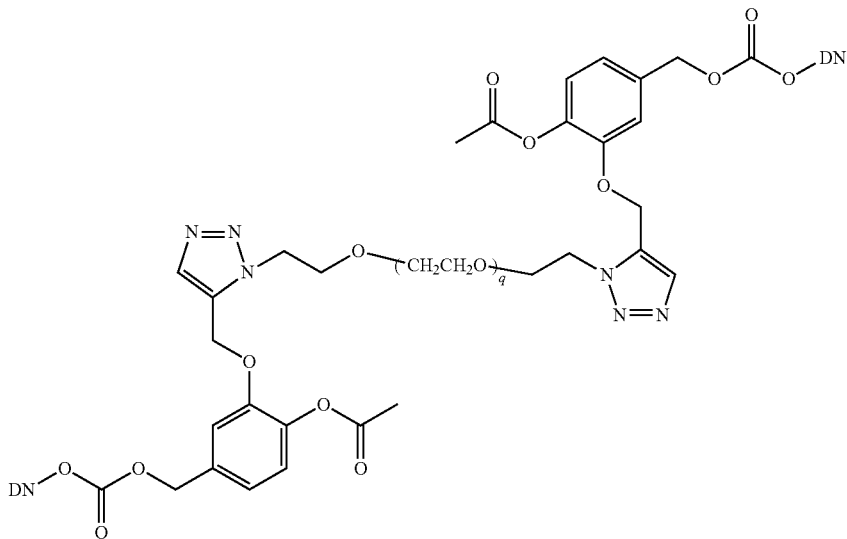
(IX-d-D2)
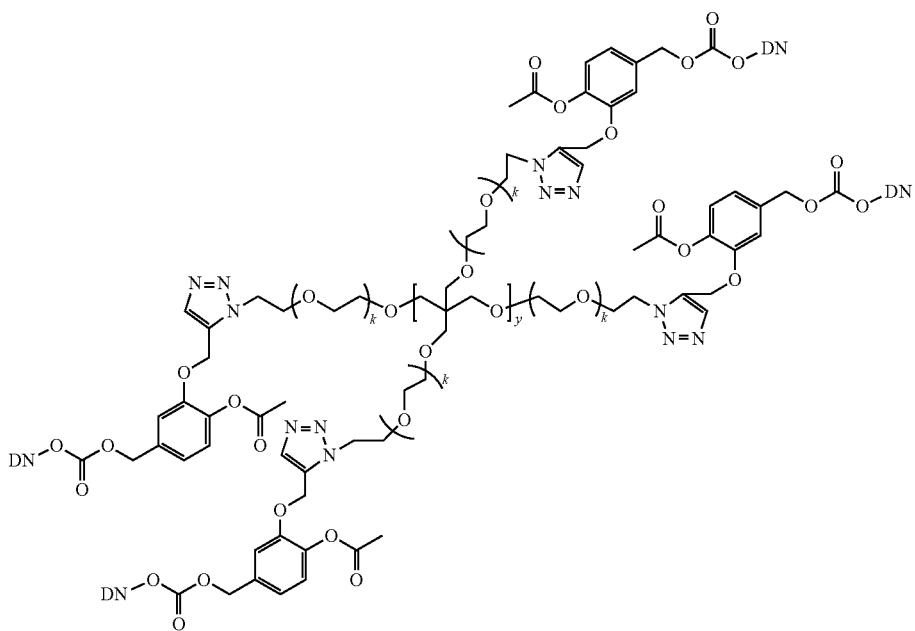
(IX-d-D3)
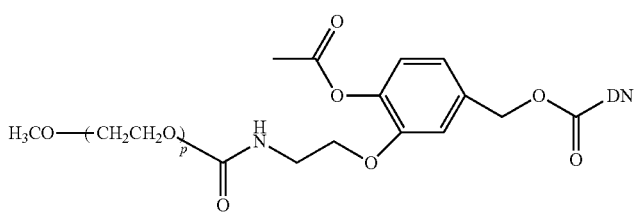
(IX-e-D1)
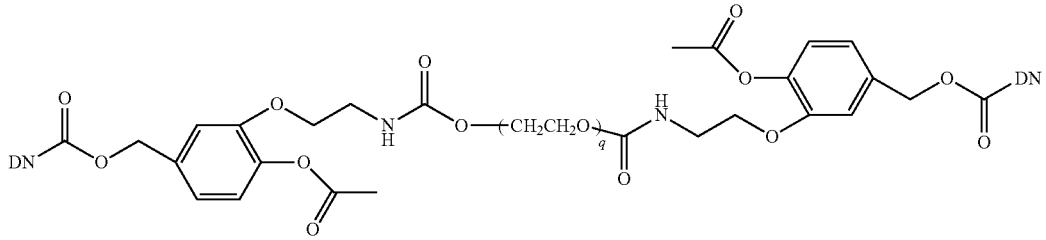
(IX-e-D2)

(IX-e-D3)

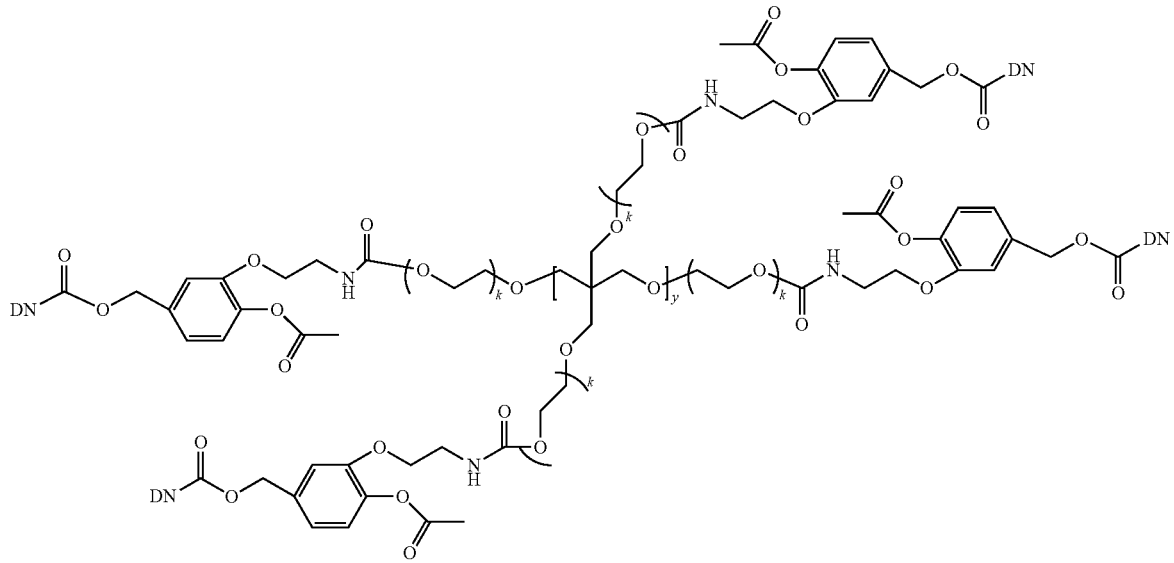

In the above formulae, DN is

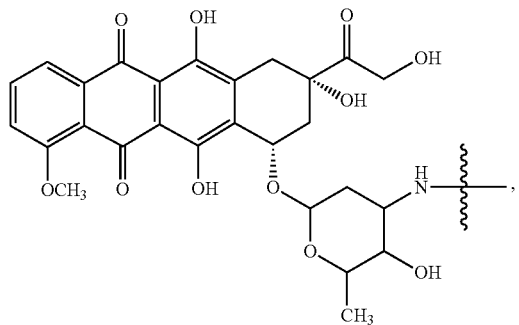 [SMILES: *NC1CC(O[C@H]2C[C@](O)(C(=O)CO)Cc3c(O)c4c(c(O)c32)C(=O)c2c(OC)cccc2C4=O)OC(C)C1O]

and p, q, k and y respectively have the definitions in the general formulae III, V, VI and VII-3 of the disclosure.

In one example of the disclosure, in the above formulae, y is an integer of 1 to 5, for example, 1, 2, 3, 4 or 5.

Another aspect of the disclosure also provides a method for preparing the above polyethylene glycol-linker-drug conjugate, including a step of reacting and linking the above polyethylene glycol-linker conjugate derivative of the disclosure with a drug.

Preferably, in the preparing method, the derivative is an active ester, and more preferably, a reactive group of the derivative is an active carbonate group.

In one example of the disclosure, the derivative have the structures of the above formulae VIII-a to VIII-e.

Preferably, in the preparing method, a reactive group of the drug is an amido group, and more preferably a primary amine group.

In one example of the disclosure, the drug is a polypeptide and protein drug, preferably IL-2, and more preferably rhIL-2.

In one example of the disclosure, the drug is adriamycin or a derivative thereof, which has the structure of the above general formula X of the disclosure, and preferably adriamycin, which has the structure of the above general formula X-1 of the disclosure.

In one preferred example of the disclosure, the polyethylene glycol-linker-drug conjugate is a polyethylene glycol-linker-IL-2 conjugate, and a preparing method thereof includes a step of reacting and linking the polyethylene glycol-linker conjugate derivative with IL-2.

Preferably, in the preparing method of the polyethylene glycol-linker-IL-2 conjugate, a molar ratio of the polyethylene glycol-linker conjugate derivative to IL-2 is 1 to 50:1 (for example, 1:1, 5:1, 10:1, 15:1, 20:1, 25:1, 30:1, 35:1, 40:1, 45:1 or 50:1), and more preferably 10 to 30:1.

Preferably, in the preparing method of the polyethylene glycol-linker-IL-2 conjugate, a reaction pH value is 6.0 to 10.0 (for example, 6.0, 6.5, 7.0, 7.5, 8.0, 8.5, 9.0, 9.5 or 10.0).

Preferably, in the preparing method of the polyethylene glycol-linker-IL-2 conjugate, a reaction temperature is 20 to 30° C., and more preferably a room temperature.

Preferably, in the preparing method of the polyethylene glycol-linker-IL-2 conjugate, the reaction is carried out in a buffer solution, and those skilled in the art can select an appropriate buffer solution type, such as a phosphate buffer solution, a borate buffer solution or a sodium bicarbonate buffer solution, according to an adopted reaction pH value, and the disclosure is not specifically limited to this.

Preferably, the preparing method of the polyethylene glycol-linker-IL-2 conjugate further includes a step of terminating the reaction, wherein the step of terminating the reaction includes adding a glycine solution, and a concentration of the glycine solution is 0.5 to 2 M (for example, 0.5, 1.0, 1.5 or 2.0 M).

Preferably, the preparing method of the polyethylene glycol-linker-IL-2 conjugate further includes a step of separating and purifying a reaction product. One or a combination of several of methods commonly used in the field, such as ion exchange column chromatography, reverse phase high performance liquid chromatography separation and gel permeation chromatography separation, may be adopted as the separating and purifying method, and the disclosure is not specifically limited to this.

Another aspect of the disclosure also provides a composition of the above polyethylene glycol-linker-drug conjugate, wherein the composition includes at least two of the polyethylene glycol-linker-drug conjugates of the disclosure with different n values.

In one example of the disclosure, the above composition includes at least three of the polyethylene glycol-linker-drug conjugates of the disclosure with different n values.

In one example of the disclosure, the drug in the above composition is a polypeptide and protein drug, preferably a cytokine, and more preferably IL-2 (such as rhIL-2).

Preferably, the polyethylene glycol-linker-drug conjugate is a polyethylene glycol-linker-IL-2 conjugate.

In one example of the disclosure, the composition includes a polyethylene glycol-linker-IL-2 conjugate with an n value of 1 to 7.

In one example of the disclosure, the composition includes a polyethylene glycol-linker-IL-2 conjugate with an n value of 1 to 3.

In one example of the disclosure, the composition includes a polyethylene glycol-linker-IL-2 conjugate with an n value of 3 to 5.

In one example of the disclosure, the composition includes a polyethylene glycol-linker-IL-2 conjugate with an n value of 4 to 7.

Another aspect of the disclosure also provides a pharmaceutically acceptable salt, an isomer, a prodrug or a solvate of the above polyethylene glycol-linker-drug conjugate.

Another aspect of the disclosure also provides a pharmaceutical composition including the above polyethylene glycol-linker-drug conjugate and the pharmaceutically acceptable salt, the isomer, the prodrug or the solvate thereof, and a pharmaceutically acceptable carrier or additive.

As used herein, the term "pharmaceutically acceptable" refers to having a physiological compatibility after administration to a human without causing gastrointestinal disorder, and an anaphylactic reaction or similar reaction like dizziness. The additive may be any one of an excipient, a disintegrant, a binder, a lubricant, a suspending agent, a stabilizer, etc. The excipient includes examples such as lactose, mannitol, isomalt, microcrystalline cellulose, silicified microcrystalline cellulose, powdered cellulose, etc. The disintegrant includes examples such as low-substituted hydroxypropyl cellulose, crospovidone, sodium starch glycolate, croscarmellose sodium, starch, etc. The binder includes examples such as hydroxypropyl cellulose, hydroxypropyl methyl cellulose, povidone, copovidone, pregelatinized starch, etc. The lubricant includes examples such as stearic acid, magnesium stearate, sodium stearyl fumarate, etc. A wetting agent includes examples such as polyoxyethylene sorbitan fatty acid ester, poloxamer, polyoxyethylene castor oil derivative, etc. The suspending agent includes examples such as hydroxypropyl methyl cellulose, hydroxypropyl cellulose, polyvidone, copovidone, sodium carboxymethylcellulose, methylated cellulose, etc. The stabilizer includes examples such as citric acid, fumaric acid, succinic acid, etc. In addition, the pharmaceutical composition of the disclosure may also include any one of an anticoagulant, a flavoring agent, an emulsifier, a preservative, etc.

The pharmaceutical composition of the disclosure may be a tablet (including a sugar-coated tablet, a film-coated tablet, a sublingual tablet, an orally disintegrating tablet, an oral tablet, etc.), a pill, a powdered drug, a granule, a capsule (including a soft capsule and a microcapsule), a lozenge, a syrup, a liquid, an emulsion, a suspension, a controlled-release preparation (such as an instantaneous-release preparation, a sustained-release preparation and a sustained-release microcapsule), an aerosol, a film agent (such as an oral disintegrating film agent, an oral mucosa-adhesive film agent), an injection (such as a subcutaneous injection, an intravenous injection, an intramuscular injection and an intraperitoneal injection), an intravenous dripping agent, a transdermal absorption preparation, an ointment, a lotion, an adhesive preparation, a suppository (such as a rectal suppository and a vaginal suppository), a pilule, a nasal preparation, a lung preparation (an inhalant), an eye drop and the like, an oral or parenteral preparation (such as administration to a vicinity of a tumor and direct administration to a lesion in an intravenous, intramuscular, subcutaneous, intra-organ, intranasal, intradermal, dripping, intracerebral or intrarectal manner). Preferably, the pharmaceutical composition is an injection.

The pharmaceutically acceptable excipient according to the disclosure is preferably a pharmaceutically acceptable injection excipient, such as an isotonic sterile saline solution (sodium dihydrogenphosphate, disodium hydrogen phosphate, sodium chloride, potassium chloride, calcium chloride, magnesium chloride, etc., or a mixture of the above salts), or the pharmaceutical composition is a dry composition, such as a lyophilized composition, which is appropriately added with sterile water or normal saline to form an injectable solute.

Another aspect of the disclosure also provides an application of the linker compound and the polyethylene glycol-linker conjugate above in preparing a polyethylene glycol-linker conjugate derivative.

Preferably, the derivative is active ester, and more preferably active carbonate.

Another aspect of the disclosure also provides an application of the linker compound, the polyethylene glycol-linker conjugate and the derivative thereof above in modifying a drug.

Preferably, the application is to prepare a polyethylene glycol-linker-drug conjugate; and the drug has the above definition of the disclosure.

Another aspect of the disclosure also provides an application of the linker compound, the polyethylene glycol-linker conjugate and the derivative thereof, the polyethylene glycol-linker-drug conjugate and the pharmaceutically acceptable salt thereof, the isomer, the prodrug or the solvate, and the pharmaceutical composition above in preparing a drug for preventing and/or treating a disease.

Preferably, the disease refers to a tumor, an autoimmune disease, a viral disease or a bacterial disease.

Preferably, the tumor disease includes renal cell carcinoma, melanoma, malignant hemangioendothelioma, cutaneous T-cell tumor, ovarian cancer, breast cancer, bladder cancer, lung cancer, neurospongioma, neuroblastoma, liver cancer, hairy cell leukemia, myeloid blastic leukemia, colon cancer, cancerous pleural effusion or non-Hodgkin lymphoma, etc.

Preferably, the autoimmune disease includes rheumatoid arthritis, systemic lupus erythematosus and sicca syndrome.

Preferably, the virus includes hepatitis virus, papillomavirus, HSV, HIV, EBv, coronavirus, influenza virus, etc., and more preferably includes hepatitis virus, such as HBV or HCV.

Preferably, the bacterial disease includes leprosy, pulmonary tuberculosis, etc.

Preferably, the application is the application of the polyethylene glycol-linker-IL-2 conjugate according to the disclosure in preparing a drug for enhancing an immune function of a tumor patient after surgery, radiotherapy or chemotherapy.

Another aspect of the disclosure also provides a method of applying the above pharmaceutical composition to an individual.

The linker compound as well as the conjugate thereof with the polyethylene glycol and the derivative thereof provided by the disclosure may be used for modifying a drug, and a modification reaction is simple and easy to carry out. Moreover, a reaction yield is high, and an application range of the modified drug is wide. The polypeptide and protein drug provided by the disclosure can be degraded and separated from the structure of the conjugate through a conjugate of a non-peptide linker and polyethylene glycol, especially an interleukin (such as interleukin 2) through the conjugate of the non-peptide linker and polyethylene glycol, thus realizing sustained release and controlled release, reducing an administration frequency, and greatly improving a bioavailability of the drug and a patient compliance. In particular, the inventor of the disclosure has conducted more in-depth research on a coupling degree of the conjugate to obtain the conjugate or a mixture thereof with a definite coupling degree, which is beneficial to subsequent optimization of efficacy and pharmacological research.

DETAILED DESCRIPTION OF EMBODIMENTS

Figure 1:
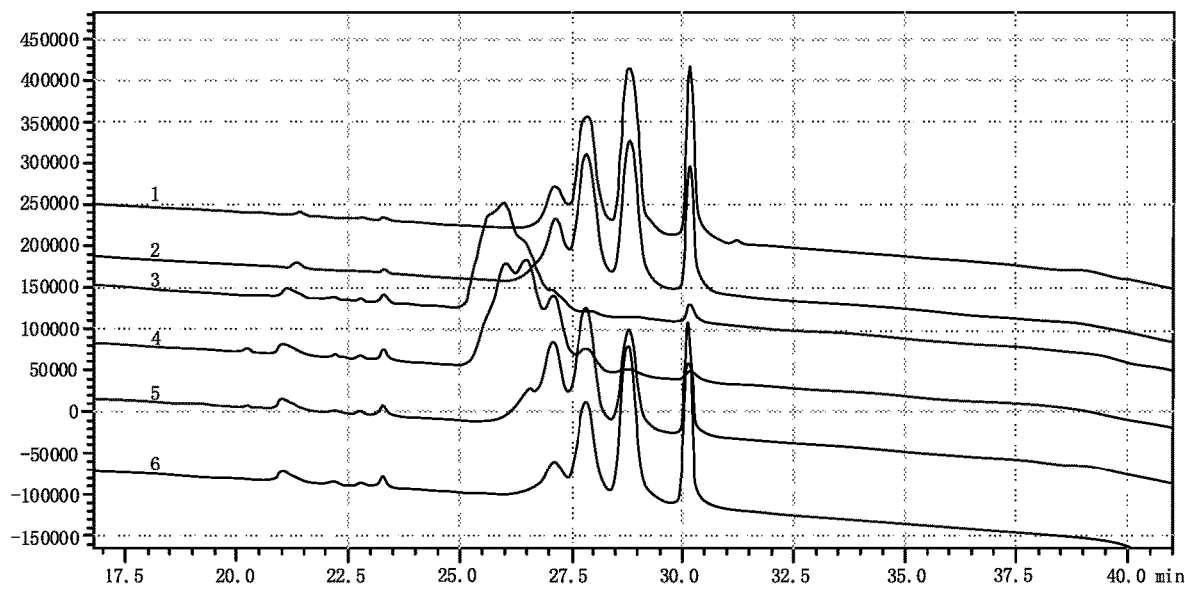
FIG. 1 illustrates an RP-HPLC chromatogram of mPEG-L5-rhIL-2 (20K) prepared by each reaction group in Example 8, with a detection wavelength of 214 nm. From top to bottom, 1 refers to reaction group 1, 2 refers to reaction group 2, 3 refers to reaction group 3, 4 refers to reaction group 4, 5 refers to reaction group 5, and 6 refers to reaction group 6.

Unless otherwise defined, all technical and scientific terms used in the disclosure have the same meaning as those commonly understood by those skilled in the art to which the disclosure relates. For example, "polypeptide and protein drugs" refer to polypeptide and protein substances used for prevention, treatment and diagnosis, wherein polypeptides may be compounds formed by linking α-amino acids together with peptide bonds, and may also be intermediate products of protein hydrolysis; and N polypeptide chains are wound and tangled according to a certain spatial structure to form proteins. The polypeptide and protein drugs may be classified into amino acid and derivatives drugs thereof, polypeptide and protein drugs, enzyme and coenzyme drugs, nucleic acid and degradation products and derivatives drugs thereof, carbohydrate drugs, lipid drugs, cell growth factors and other biological products drugs.

The IL-2 described in the disclosure may be natural, recombinant protein (such as recombinant human interleukin 2) or mutant with natural IL-2 function (such as "IL-2-C125A/L18M/L19S" described in doctoral dissertation of Liu Yan "Clone of Recombinant Human Interleukin-2 (IL-2) Mutant and Expression and Purification in Pasteur Pichia Pastoris System"), and also includes products obtained by tissue culture, protein synthesis and cell culture (natural, recombinant cells or mutants). Methods for extracting and separating the natural, recombination IL-2 or mutants are well known to those skilled in the art.

The English abbreviations and representative meanings thereof in the disclosure are as follows:

IL-2 is interleukin 2; rhIL-2 is recombinant human interleukin 2; HSV is herpes simplex virus; HIV is human immunodeficiency virus; HBV is hepatitis B virus; HCV is hepatitis C virus; and EBv is Epstein-barr virus.

The following clearly and completely describes the technical solutions of the disclosure with reference to the examples of the disclosure. Apparently, the described examples are merely some but not all of the examples of the disclosure. Based on the examples in the disclosure, all other examples obtained by those of ordinary skills in the art without going through any creative work shall fall within the scope of protection of the disclosure.

The compound raw materials used in the disclosure can be commercially available or prepared according to the disclosed preparing method, which does not limit the scope of the disclosure.

The polyethylene glycol and the derivative thereof used in the examples are provided by Beijing JENKEM Technology Co., Ltd. Unless otherwise specified, the molecular weights are all 20K. Other reagents are commercially available.

Example 1: Synthesis of Linking Chain (L)

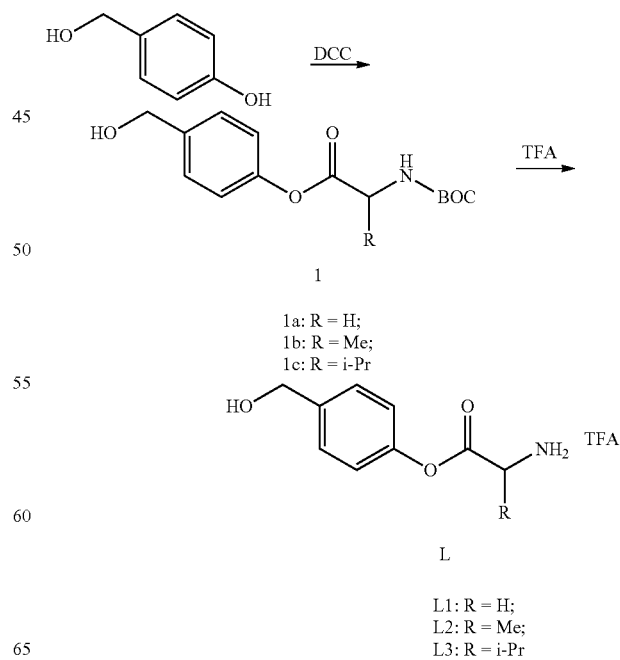

BOC-amino acid (92.2 mmol) and N,N-dicyclohexylcarbodiimide (DCC, 23.8 g, 115.3 mmol) were added to dichloromethane (500 mL), cooled in an ice-water bath, and then p-hydroxybenzylalcohol (11.4 g, 92.2 mmol) was added. After addition, the ice bath was removed, and the mixture was reacted overnight at room temperature. The mixture was filtered, and a filter cake was washed with ethyl acetate, a filtrate was evaporated to dryness to obtain a crude product, and the crude product is purified through column chromatography to obtain a product 1.

1a: 19.7 g, in 76.0% yield. $1^H$ NMR: (CDCl$_3$): 8.75 (s, 1H), 7.22 (d, 2H), 7.05 (d, 2H), 4.87 (s, 2H), 3.74 (s, 2H), 1.52 (s, 9H).

1b: 20.3 g, in 74.8% yield. $1^H$ NMR: (CDCl$_3$): 8.74 (s, 1H), 7.21 (d, 2H), 7.05 (d, 2H), 4.88 (s, 2H), 3.77 (m, 1H), 1.51 (s, 9H), 1.27 (d, 3H).

1c: 21.6 g, in 72.5% yield. $1^H$ NMR: (CDCl$_3$): 8.75 (s, 1H), 7.22 (d, 2H), 7.05 (d, 2H), 4.87 (s, 2H), 3.61 (d, 1H), 2.82 (m, 1H), 1.52 (s, 9H), 1.06 (d, 6H).

Compound 1 (39.1 mmol) was dissolved in dichloromethane (250 mL), added with trifluoroacetic acid (50 mL), and then the mixture was stirred overnight at room temperature after addition, and concentrated. Dichloromethane was added to the residues and then evaporated to dryness. This process was repeated three times, and ethyl ether was finally to precipitate and filter to obtain a product L.

L1: 11.1 g, in 96.7% yield.
L2: 11.6 g, in 97.1% yield.
L3: 12.7 g, in 96.3% yield.

Example 2: Synthesis of Conjugate (mPEG-L-40K) of Monomethoxy Polyethylene Glycol Acetic Acid and Linking Chain

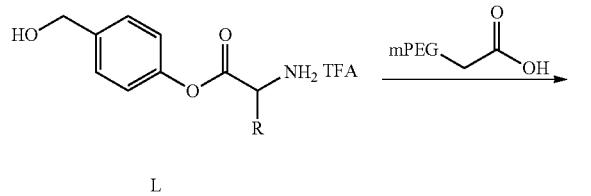

L

L1: R = H;
L2: R = Me;
L3: R = i-Pr

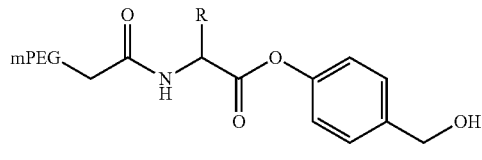

mPEG-L mPEG-L1: R = H;
mPEG-L2: R = Me;
mPEG-L3: R = i-Pr.

Monomethoxy polyethylene glycol-acetic acid (mPEG-CM, 40K, 5 g, 0.125 mmol), compound L (0.25 mmol, prepared in Example 1) and 1-hydroxybenzotriazole (HOBt, 16.9 mg, 0.125 mmol) were added to a reaction flask, dissolved with dichloromethane, and then diisopropylethylamine (45.2 mg, 0.35 mmol) was added. The mixture was stirred evenly, cooled in an ice-bath, and then EDCI (47.9 mg, 0.25 mmol) was added in batches. After the addition of EDCI, the reaction system was naturally warmed up to room temperature and reacted overnight. After the reaction solution was concentrated the next day, the residues were crystallized with isopropyl alcohol, subjected to suction filtration and dried to obtain a product mPEG-L.

mPEG-L1 (40K): 4.6 g, in 92.4% yield.
mPEG-L2 (40K): 4.5 g, in 90.8% yield.
mPEG-L3 (40K): 4.7 g, in 93.7% yield.

Example 3: Preparation of Linking Chain L5

A synthesis route of the linking chain L5 was as follows:

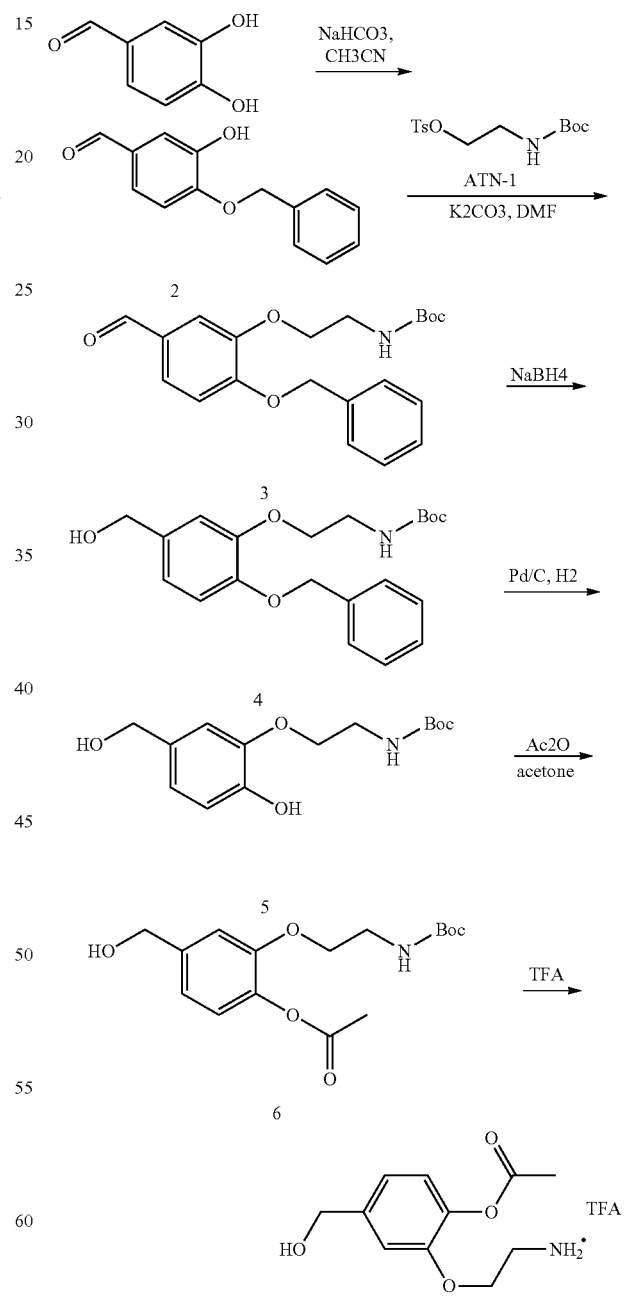

Synthesis of Compound (2):

3,4-dihydroxy benzaldehyde (10 g, 72.5 mmol) was dissolved in acetonitrile (150 mL), and added with sodium bicarbonate (8 g, 94.3 mmol), and then the mixture was warmed up to 60° C. Benzyl bromide (12.4 g, 72.5 mmol) was added in the mixture, and then the mixture was warmed up to 80° C. and stirred overnight. The acetonitrile was removed by concentration, and 10% aqueous hydrochloric acid solution (200 mL) was added into the residues, then the mixture was extracted with ethyl acetate (150 mL*3), combined and dried, filtered and concentrated, and the residues were purified through column chromatography to obtain 10 g of off-white solid (in 60% yield). $^1$H NMR: (CDCl$_3$): δ9.82 (s, 1H), 7.48-7.40 (m, 7H), 7.05 (m, 1H), 6.02 (s, 1H), 5.21 (s, 2H).

Synthesis of Compound (3):

Compound (2) (5 g, 21.9 mmol) was dissolved in DMF (80 mL), and added with potassium carbonate (7.6 g, 54.75 mmol) and potassium iodide (0.73 g 4.38 mmol), and then the mixture was stirred for 10 minutes. ATN-1 (9 g, 28.47 mmol) was added in the mixture and then the mixture was warmed up to 70° C. and stirred overnight. Post-treatment was carried out to add saturated solution of ammonium chloride (400 mL) into the reaction solution, then the mixture was extracted with ethyl acetate (150 mL*3), combined and dried, filtered and concentrated, and the residues were purified through column chromatography to obtain 5 g of white solid (in 61% yield). $^1$H NMR: (CDCl$_3$): δ9.85 (s, 1H), 7.47-7.36 (m, 7H), 7.03 (m, 1H), 5.24 (s, 2H), 5.07 (s, 1H), 4.17 (m, 2H), 3.59 (m, 2H), 1.46 (s, 9H).

Synthesis of Compound (4):

Compound (3) (5 g, 13.5 mmol) was dissolved in tetrahydrofuran (100 mL), and added with sodium borohydride (0.77 g, 20.25 mmol) at room temperature, then the mixture was stirred for 2 hours at room temperature and then cooled to 0° C. Acetic acid (2 mL) was added to quench the reaction, a solvent was removed by concentration under reduced pressure, and the residues were purified through column chromatography to obtain 4 g of colorless oily matter (in 80% yield). $^1$H NMR: (DMSO-d6): δ7.38-7.05 (m, 8H), 6.80 (m, 1H), 5.09 (s, 2H), 5.06 (m, 1H), 4.40 (m, 2H), 3.98 (m, 2H), 3.31 (m, 2H), 1.38 (s, 9H).

Synthesis of Compound (5):

Compound (4) (1 g, 2.7 mmol) was dissolved in methanol (8 mL), and added with Pd/C (10%, 0.3 g), then hydrogen was introduced to react overnight. The mixture was filtered, a filtrate was concentrated, and the residues were purified through column chromatography to obtain 0.6 g of product (in 78% yield). $^1$H NMR: (DMSO-d6): δ8.37 (s, 1H), 7.09 (s, 1H), 6.71 (s, 1H), 6.65 (d, 1H), 6.56 (d, 1H), 4.45 (s, 2H), 3.89 (m, 2H), 3.31 (m, 2H), 1.38 (s, 9H).

Synthesis of Compound (6):

Compound (5) (0.6 g, 2.1 mmol) was dissolved in acetone (7 mL), and added with potassium carbonate (0.58 g, 4.2 mmol), then the system was cooled to 0° C., acetyl oxide (235 mg, 2.3 mmol) was added, and the mixture was slowly warmed up to room temperature and reacted for 3 hours. Post-treatment was carried out to add an aqueous solution of ammonium chloride (30 mL), then the mixture was extracted with ethyl acetate, combined and concentrated, and purified through column chromatography to obtain 0.5 g of product (in 73% yield). $^1$H NMR: (DMSO-d6): δ7.12 (s, 1H), 6.89 (s, 1H), 6.65 (d, 1H), 6.56 (d, 1H), 4.45 (s, 2H), 3.89 (m, 2H), 3.31 (m, 2H), 2.14 (s, 3H), 1.38 (s, 9H).

Synthesis of Compound (L5):

Compound (6) (0.5 g, 1.5 mmol) was dissolved in dichloromethane (7 mL), and added with trifluoroacetic acid (4 mL) to stir for 1 hour at room temperature. A solvent was removed by concentration, and ethyl ether was added into the residues to dissolve out solids, then the solids were filtered and dried to obtain 0.3 g of solid product in 86% yield. $^1$H NMR: (DMSO-d6): δ8.30 (s, 1H), 6.89 (s, 1H), 6.65 (d, 1H), 6.56 (d, 1H), 4.45 (s, 2H), 3.85 (m, 2H), 3.29 (m, 2H), 2.12 (s, 3H).

Example 4: Synthesis of Conjugate (mPEG-L5-NHS-20K) of Monomethoxy Polyethylene Glycol Acetic Acid and Linking Chain

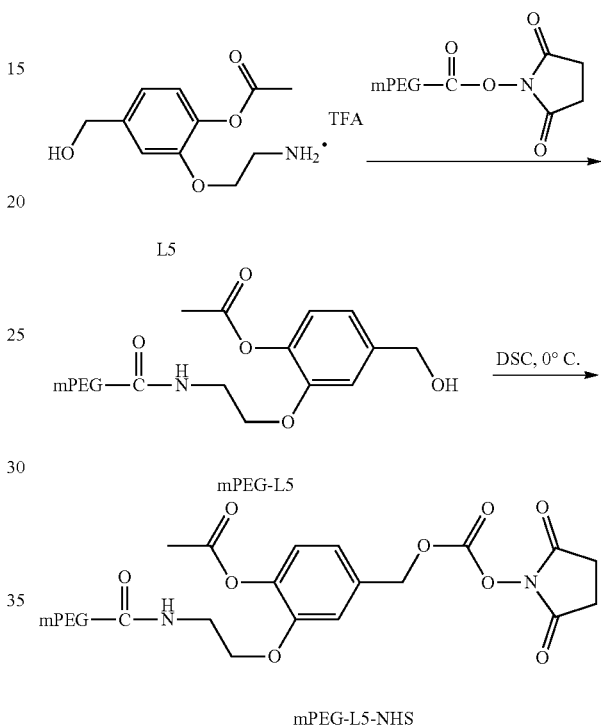

Synthesis of mPEG-L5:

mPEG (20K)-CM-NHS (2 g, 0.1 mmol) was dissolved in anhydrous methylene chloride, and subcooled to 0° C. DIPEA (78 mg, 0.6 mmol) was added, and then compound L5 was added. The mixture was slowly warmed up to room temperature and stirred overnight. After the reaction solution was concentrated, the residues were crystallized with isopropyl alcohol, subjected to suction filtration and then dried to obtain a product mPEG-L5 (1.8 g, 90%). $^1$H NMR: (DMSO-d6): δ8.10 (s, 1H), 6.85 (s, 1H), 6.72 (d, 1H), 6.65 (d, 1H), 5.34 (s, 2H), 4.20 (m, 2H), 3.65 (m, 1800H), 3.51 (m, 2H), 3.24 (s, 3H), 2.78 (m, 4H), 2.12 (s, 3H).

Synthesis of mPEG-L5-NHS:

Compound mPEG-L5 (1 g, 0.05 mmol) was added into a reaction flask, dissolved with dichloromethane (6 mL), and cooled under the protection of N$_2$, then succinimide carbonate (19.0 mg, 0.075 mmol) was added, and the mixture was stirred and dissolved. After that, DIPEA (12.9 mg, 0.1 mmol) was added, and a cold bath was removed after the addition of DIPEA, and the mixture was reacted overnight at room temperature. The reaction solution was concentrated, and the residues were crystallized with isopropyl alcohol to obtain a product mPEG-L5-NHS. 1H NMR: (DMSO-d6): δ8.10 (s, 1H), 6.85 (s, 1H), 6.72 (d, 1H), 6.65 (d, 1H), 4.65 (s, 2H), 4.15 (m, 2H), 3.65 (m, 1800H), 3.29 (m, 2H), 3.24 (s, 3H), 2.12 (s, 3H).

Example 5: Synthesis of Y-PEG-L5-NHS-20K

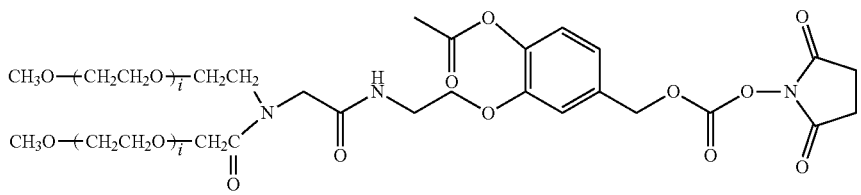

Refer to Example 4 for a preparing method of U-PEG-L5-NHS-20K.

Example 6: Synthesis of U-PEG-L5-NHS-20K

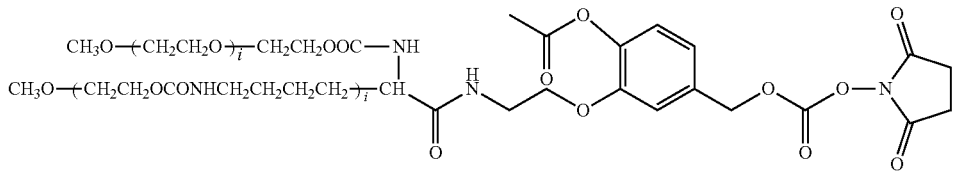

Refer to Example 4 for a preparing method of U-PEG-L5-NHS-20K.

Example 7: Synthesis of 8Arm-PEG-L5-NHS-20K

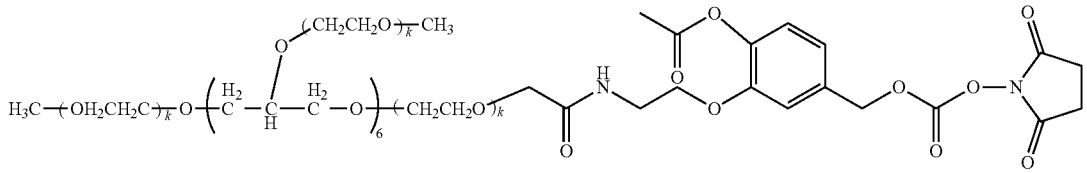

Refer to Example 4 for a preparing method of 8arm-PEG-L5-NHS-20K.

Example 8: Synthesis of mPEG-L5-rhIL-2 (20K)

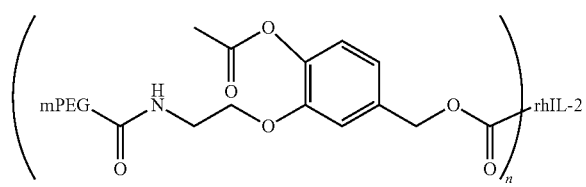

Under the purging of nitrogen, mPEG-L5-NHS (20K, prepared in Example 4) stored at −20° C. was warmed up to room temperature. An mPEG-L5-NHS (20K) stock solution (200 mg/mL) was prepared in DMSO and added into a rhIL-2 solution (reaction grouping, reaction conditions such as a molar ratio of reactant mPEG-L5-NHS to rhil-2 (hereinafter referred to as a molar ratio of PEG to rhIL-2 molar ratio) and a specific reaction pH were shown in Table 1). A final concentration of rhIL-2 in the mixture was 0.5 mg/mL. Sodium bicarbonate buffer solution (1 M, pH 9.0) was added to the mixture respectively to reach a final concentration of 20 mM, and then the mixture was reacted at room temperature for 2 hours to provide conjugates. After 2 hours, 1 M of glycine (pH 6.0) was added respectively to a final concentration of 100 mM to terminate the reaction.

Figure 2:
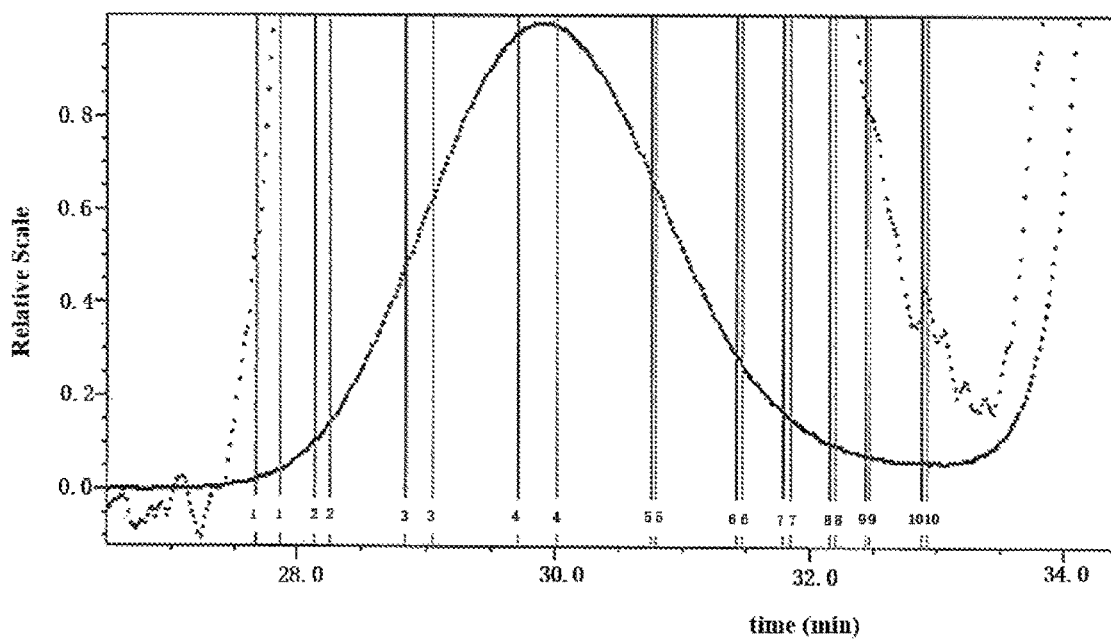
FIG. 2 illustrates an SEC-MALS spectrogram of the mPEG-L5-rhIL-2 (20K) prepared by the reaction group 3 in Example 8.

Coupling conditions of different reaction groups were determined by RP-HPLC for the terminated reaction system, and a coupling efficiency and a coupling degree were analyzed and evaluated according to migration conditions of the conjugates (left shift represented a high coupling degree), an RP-HPLC spectrogram was shown in FIG. 1, and it could be seen from FIG. 1 that both the coupling degrees and the coupling efficiencies of the reaction group 3 were greater than that of a reaction group 4/greater than that of a reaction group 5/greater than that of a reaction group 2/greater than that of a reaction group 6/greater than that of a reaction group 1. SEC+MALS analysis reactions were further carried out in the reaction group 3 to evaluate the coupling degree, and the results were shown in FIG. 2.

Coupling degree results of the conjugate mPEG-L5-rhIL-2 (20K) prepared in this example were shown in Table 1.

TABLE 1

SEC-MALS Coupling Degree Result Table of The Conjugate Prepared in Example 8

| | Reaction group 1 | Reaction group 2 | Reaction group 3 | Reaction group 4 | Reaction group 5 | Reaction group 6 |
|---|---|---|---|---|---|---|
| Molar ratio of fed materials | 10:1 | 20:1 | 30:1 | 30:1 | 30:1 | 30:1 |
| Reaction pH | 9.8 | 9.8 | 9.8 | 8.0 | 7.2 | 6.0 |
| Coupling degree | 1, 2, 3 | 1, 2, 3 | 4 to 7 | 3 to | 1, 2, 3 | 1, 2, 3 |
| Ratio | Greater than 90% | Greater than 90% | Greater than 90% | Greater than 90% | Greater than 70% | Greater than 80% |

The products obtained in the above table may be divided into three categories: mPEG-L5-rhL-2 with a coupling degree of 4 to 7, mPEG-L5-rhIL-2 with a coupling degree of 3 to 5, and mPEG-L5-rhL-2 with a coupling degree of 1 to 3. The optimal content may be controlled to be greater than 90%.

Figure 3:
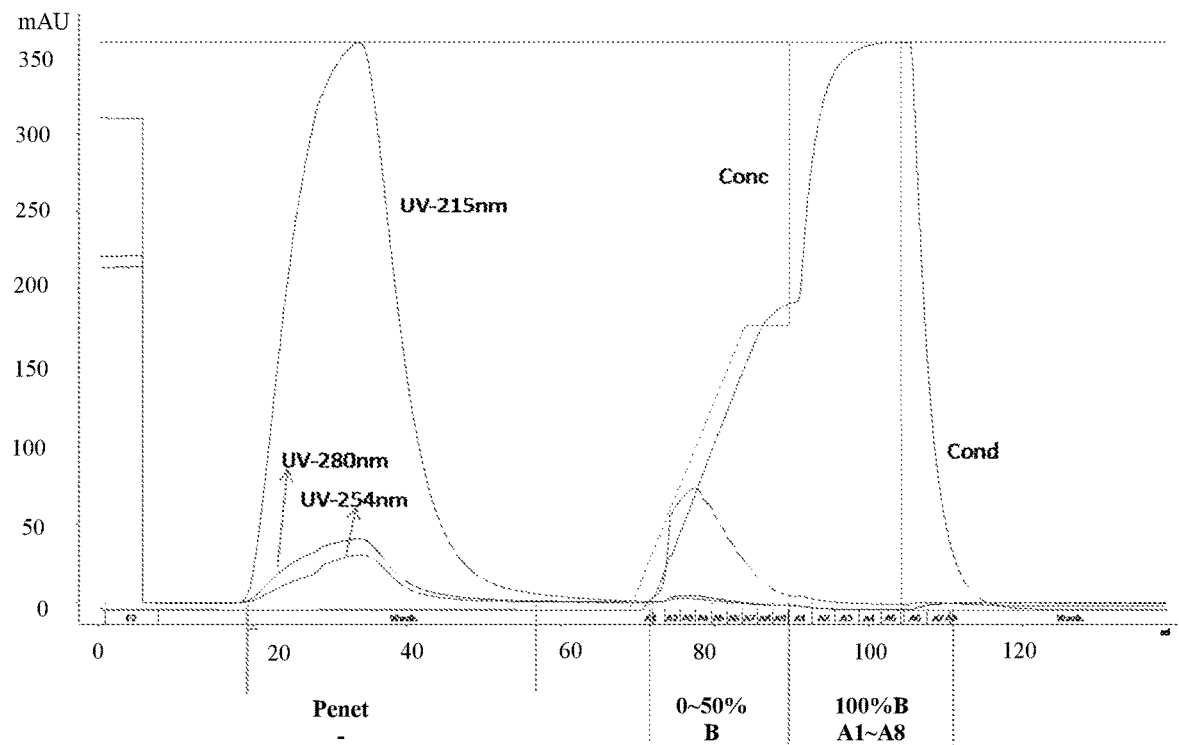
FIG. 3 illustrates a chromatogram of the mPEG-L5-rhIL-2 (20K) prepared in the reaction group 3 in Example 8 after cation exchange chromatography.
Figure 4:
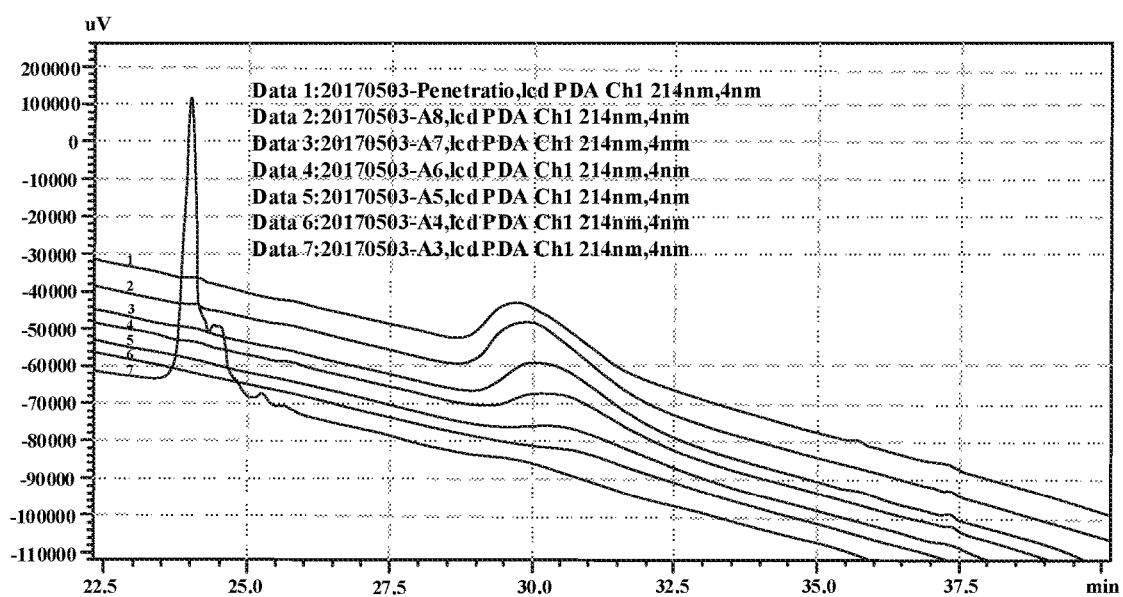
FIG. 4 illustrates an RP-HPLC chromatogram of penetration peaks and sectionally collected conjugates of the mPEG-L5-rhIL-2 (20K) prepared by the reaction group 3 in Example 8 after purification. From top to bottom, 1 refers to penetration, 2 refers to A8, 3 refers to A7, 4 refers to A6, 5 refers to A5, 6 refers to A4 and 7 refers to A3 respectively.

Then the reaction-terminated mixtures were diluted with purified water respectively to provide an electroconductibility smaller than 0.5 ms/cm (25° C.). A pH value was adjusted to 4.0 with glacial acetic acid, and then the mixture was purified through column chromatography, as shown in FIG. 3. Analysis was carried out with reference to RP-HPLC (FIG. 4), wherein PEG was enriched in a penetration peak, mPEG-L5-rhIL-2 was eluted in 0 to 50% B (0 to 0.5 M NaCl gradient), elution peaks (A3 to A8) were collected sectionally, and it was observed that the coupling degree was distributed from high to low.

Example 9: Synthesis of mPEG-L5-rhIL-2 (40K)

Refer to Example 8 for a preparing method of mPEG-L5-rhIL-2 (40K).

Example 10: Synthesis of Y-PEG-L5-rhIL-2 (20K)

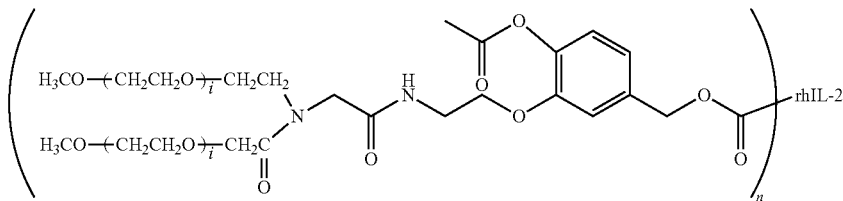

Refer to Example 8 for a preparing method of Y-PEG-L5-rhIL-2 (20K).

Example 11: Synthesis of U-PEG-L5-rhIL-2 (20K)

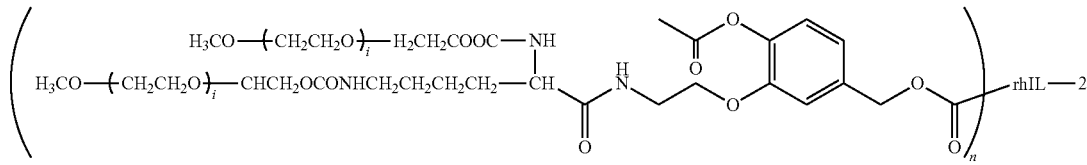

Refer to Example 8 for a preparing method of U-PEG-L5-rhIL-2 (20K).

Example 12: Synthesis of 8Arm-PEG-L5-rhIL-2 (20K)

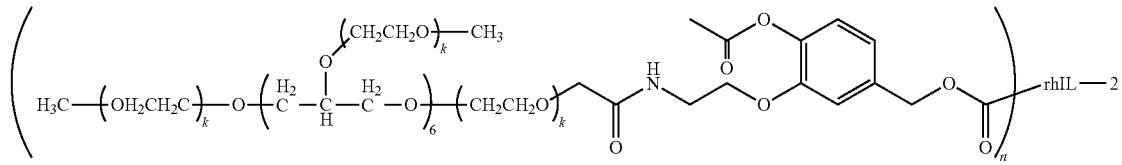

Refer to Example 8 for a preparing method of 8arm-PEG-L5-rhIL-2 (20K).

Example 13: Synthesis of mPEG-L1-rhIL-2 (20K)

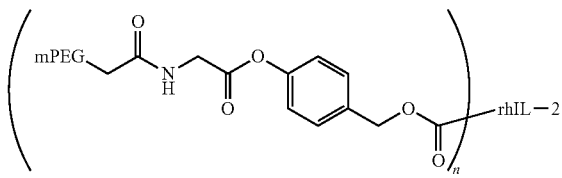

Under the purging of nitrogen, mPEG-L1-NHS (20K, refer to Example 2 for a preparing method of mPEG-L1-NHS (20K) stored at −20° C. was warmed up to room temperature. An mPEG-L1-NHS (20K) stock solution (200 mg/mL) was prepared in DMSO and added into a rhIL-2 solution (a molar ratio of PEG to rIL-2 was respectively 1:1, 3:1, 10:1, and 30:1). A final concentration of rhIL-2 in the mixture was 0.5 mg/mL. Sodium bicarbonate buffer solution (1 M, pH 9.0) was added to the mixture respectively to reach a final concentration of 20 mM, and then the mixture was reacted at room temperature for 2 hours to provide conjugates. After 2 hours, 1 M of glycine (pH 6.0) was added respectively to a final concentration of 100 mM to terminate the reaction. Then the reaction-terminated mixtures were diluted with purified water respectively to provide an electroconductibility smaller than 0.5 ms/cm (25° C.). A pH value was adjusted to 4.0 with glacial acetic acid, and then the mixture was purified through column chromatography.

Example 14: Pharmacodynamics Research of IL-2 Modified by the Disclosure

Figure 5:
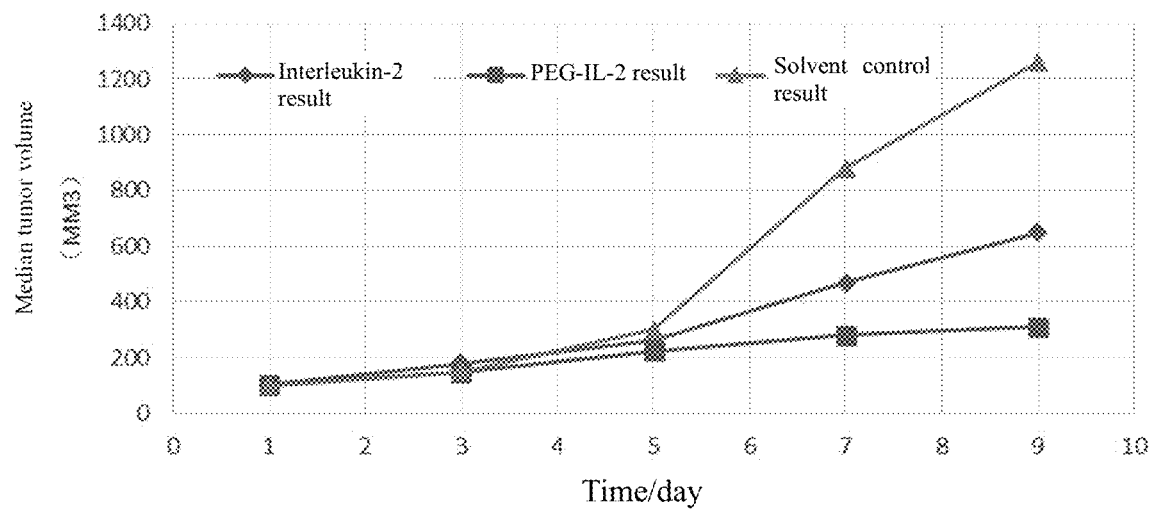
FIG. 5 illustrates an efficacy research experimental result obtained in Example 14.

PEG and rIL-2 were coupled under the reaction conditions of the reaction group 3 in Example 8. The coupled mixtures were purified by ion exchange chromatography, and a PEG-rIL-2 conjugate was separated for a pharmacodynamic experiment. A subcutaneous melanoma B16 model of a C57BL/6 mouse was used to evaluate a tumor inhibitory effect of an mPEG-L5-rhIL-2 conjugate (hereinafter referred to as PEG-rhIL-2). An experimental process is as follows: $10^6$ B16 cells were implanted in a middle of a back of each C57BL/6 mouse of 5 to 6 weeks old. After the tumor grows to a measurable size, the experimental mice were randomly grouped with each group including 6 mice, and test compounds rhIL-2, PEG-rhIL-2 and solvent control were applied to the mice in different dose concentrations and dose schemes. Body weight and tumor volume were measured every other day. The grouping of the efficacy experiments was shown in Table 2, and the experimental results were shown in Table 3 and FIG. 5.

TABLE 2

Grouping of Efficacy Experiments

| Grouping | Dose concentration | Administration route | Frequency |
|---|---|---|---|
| Solvent control group | N/A | IV | Injected once |
| rhIL-2 group | 1 mg/Kg | IV | Once a day, and injected for 5 days |
| PEG-rhIL-2 group | 1 mg/Kg | IV | Injected once |

TABLE 3

Efficacy Experimental Results

Tumor volume/mm3

| Time/day | Solvent control group | rhIL-2 group | PEG-rhIL-2 group |
|---|---|---|---|
| 1 | 100 | 102 | 104 |
| 3 | 150 | 180 | 147 |
| 5 | 300 | 260 | 225 |
| 7 | 880 | 470 | 280 |
| 9 | 1260 | 650 | 310 |

According to the data, on the $9^t$ day of administration, compared with the tumor volume (1260 mm$^3$) of the solvent control group, the tumor volume (310 mm$^3$) of the rhIL-2 group modified by the disclosure was greatly reduced, and compared with the tumor volume (650 mm$^3$) of the unmodified rhIL-2 group, the anti-tumor effect of the mPEG-L5-rhL-2 group modified by the disclosure was increased by 27%, and the administration frequency of the mPEG-L5-rhL-2 group was greatly reduced. As an anti-tumor drug, the drug modified by the disclosure has the advantages of reducing an administration frequency, and greatly improving a bioavailability of the drug and a patient compliance.

Example 15: Preparation of Monomethoxy Polyethylene Glycol-Adriamycin Conjugate (mPEG-L-Dox (40K))

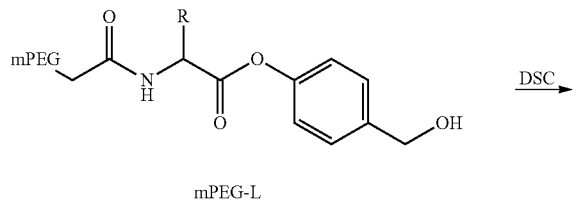

mPEG-L mPEG-L1: R = H;
mPEG-L2: R = Me;
mPEG-L3: R = i-Pr.

-continued

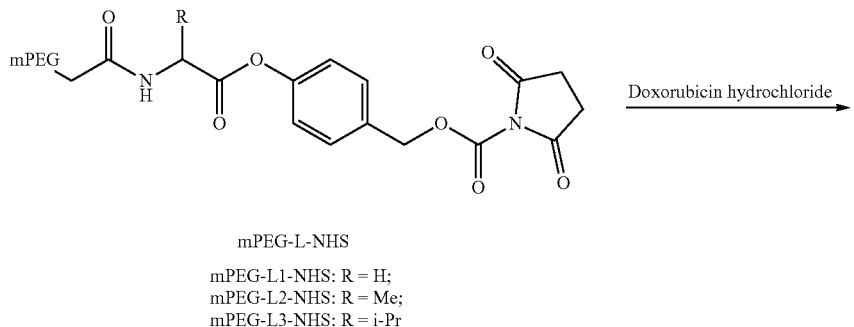

mPEG-L-NHS mPEG-L1-NHS: R = H;
mPEG-L2-NHS: R = Me;
mPEG-L3-NHS: R = i-Pr

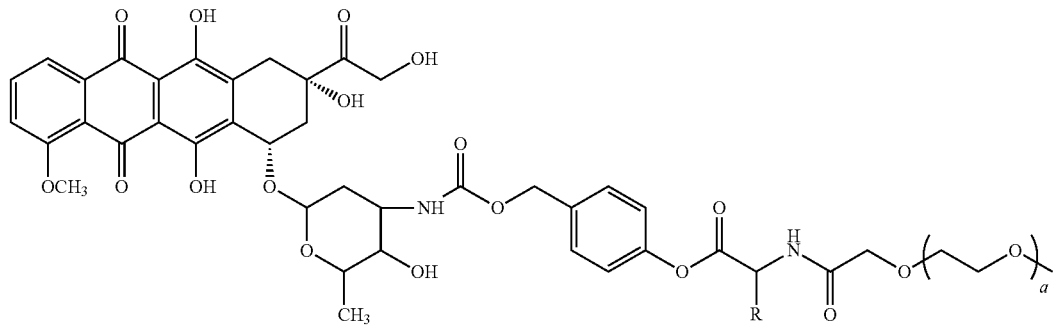

mPEG-L-Dox mPEG-L1-Dox: R = H;
mPEG-L2-Dox: R = Me;
mPEG-L3-Dox: R = i-Pr

Compound mPEG-L (0.075 mmol, prepared in Example 2) was added into a reaction flask, dissolved with dichloromethane (30 mL), and cooled under the protection of $N_2$, then succinimide carbonate (23.0 mg, 0.09 mmol) was added, and the mixture was stirred and dissolved. After that, triethylamine (10.1 mg, 0.1 mmol) was added, and a cold bath was removed after the addition of triethylamine, and the mixture was reacted overnight at room temperature. The reaction solution was concentrated, and the residues were crystallized with isopropyl alcohol to obtain a product mPEG-L-NHS.

mPEG-L1-NHS (40K): 2.6 g, in 88.5% yield.
mPEG-L2-NHS (40K): 2.7 g, in 89.2% yield.
mPEG-L3-NHS (40K): 2.6 g, in 87.9% yield.

Compound mPEG-L-NHS (0.06 mmol, prepared in last step) was dissolved in dichloromethane (25 mL), and cooled under the protection of $N_2$, then diisopropylethylamine (12.9 mg, 0.1 mmol) was added, and the mixture was stirred and dissolved. After that, doxorubicin hydrochloride (52.2 mg, 0.09 mmol) was added, and after the addition of hydrochloricacid adriamycin, the mixture was reacted at room temperature for 5 hours. After the reaction solution was concentrated, the residues were crystallized with isopropyl alcohol, subjected to suction filtration and then dried to obtain a red solid product.

mPEG-L1-Dox (40K): 2.0 g, in 84.9% yield. $^1$H NMR: (DMSO-d6): δ8.84 (s, 1H), 8.68 (s, 1H), 7.62 (m, 1H), 7.53 (d, 1H), 7.33 (d, 2H), 7.16 (d, 3H), 5.52 (s, 2H), 5.12 (t, 1H), 4.83 (s, 2H), 4.61 (s, 2H), 4.47 (s 2H), 4.32 (t, 1H), 4.06 (m, 1H), 3.96 (m, 1H), 3.89 (m, 1H), 3.65 (m, 3600H), 3.41 (m, 5H), 3.27 (m, 1H), 2.28 (d, 2H), 2.05 (d, 2H).

mPEG-L2-Dox (40K): 2.1 g, in 85.7% yield. $^1$H NMR: (DMSO-d6): δ8.82 (s, 1H), 8.67 (s, 1H), 7.62 (m, 1H), 7.53 (d, 1H), 7.33 (d, 2H), 7.16 (d, 3H), 5.52 (s, 2H), 5.12 (t, 1H), 4.83 (s, 2H), 4.59 (d, 1H), 4.47 (s 2H), 4.32 (t, 1H), 4.06 (m, 1H), 3.96 (m, 1H), 3.89 (m, 1H), 3.65 (m, 3600H), 3.41 (m, 5H), 3.27 (m, 1H), 2.28 (d, 2H), 2.05 (d, 2H), 1.58 (d, 3H).

mPEG-L3-Dox (40K): 2.1 g, in 84.6% yield. $^1$H NMR: (DMSO-d6): δ8.83 (s, 1H), 8.65 (s, 1H), 7.62 (m, 1H), 7.53 (d, 1H), 7.33 (d, 2H), 7.16 (d, 3H), 5.52 (s, 2H), 5.12 (t, 1H), 4.83 (s, 2H), 4.54 (d, 1H), 4.47 (s 2H), 4.32 (t, 1H), 4.06 (m, 1H), 3.96 (m, 1H), 3.89 (m, 1H), 3.65 (m, 3600H), 3.41 (m, 5H), 3.27 (m, 1H), 2.28 (d, 2H), 2.05 (d, 2H), 1.34 (d, 3H), 1.16 (d, 6H).

Example 16: Preparation of Conjugate (PEG-L3 (20K)) of Polyethylene Glycol Acetic Acid and Linking Chain L3

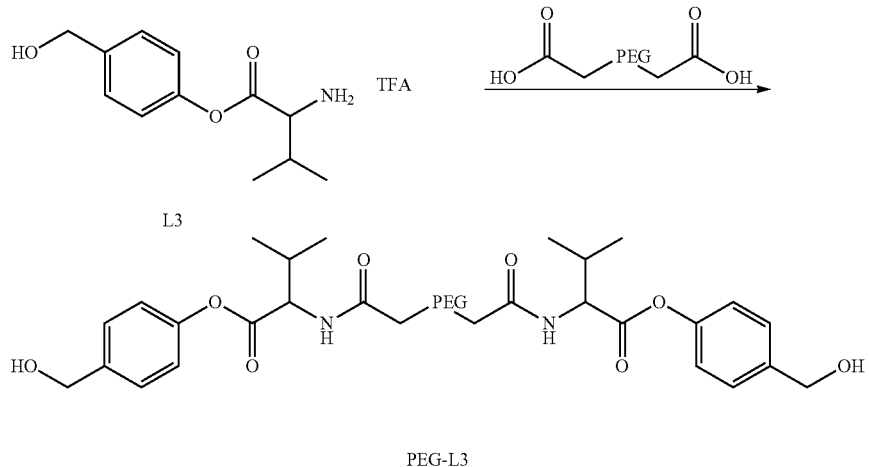

Polyethylene glycol-acetic acid (PEG-CM, 20K, 5 g, 0.25 mmol), compound L3 (168.5 mg, 0.5 mmol, prepared in Example 1) and 1-hydroxybenzotriazole (HOBt, 67.6 mg, 0.5 mmol) were added to a reaction flask, dissolved with dichloromethane, and then diisopropylethylamine (193.6 mg, 1.5 mmol) was added. The mixture was stirred evenly, cooled in an ice-bath, and then EDCI (191.7 mg, 1 mmol) was added in batches. After the addition of EDCI, the reaction system was naturally warmed up to room temperature and reacted overnight. After the reaction solution was concentrated the next day, the residues were crystallized with isopropyl alcohol, subjected to suction filtration and then dried to obtain 4.8 g of product PEG-L3 (20K) in 96% yield.

Example 17: Preparation of Conjugate (PEG-L3-Dox (20K)) of Polyethylene Glycol Acetic Acid and Linking Chain L3

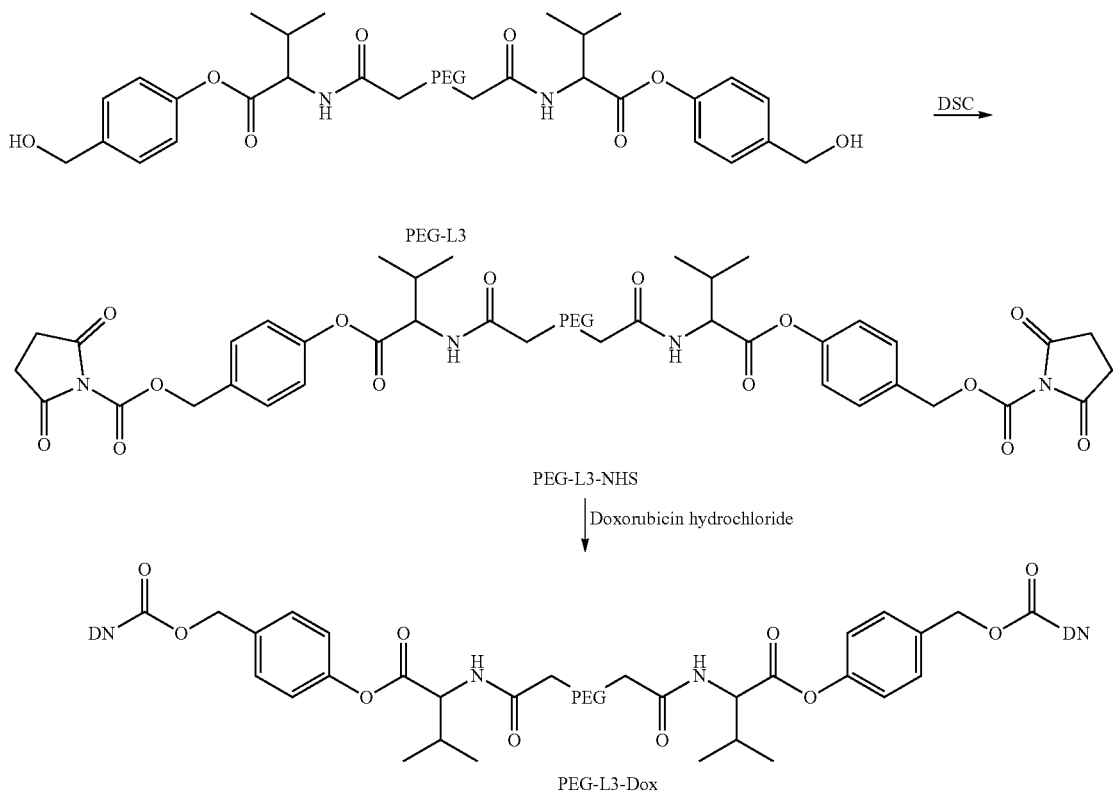

Compound PEG-L3 (2 g, 0.1 mmol, prepared in Example 16) was added into a reaction flask, dissolved with dichloromethane (40 mL), and cooled under the protection of N₂, then succinimide carbonate (51.2 mg, 0.2 mmol) was added, and the mixture was stirred and dissolved. After that, triethylamine (30.3 mg, 0.3 mmol) was added, and a cold bath was removed after the addition of triethylamine, and the mixture was reacted overnight at room temperature. After the reaction solution was concentrated, the residues were crystallized with isopropyl alcohol, subjected to suction filtration and then dried to obtain 1.8 g of product PEG-L3-NHS (20K) in 88.5% yield.

Compound PEG-L3-NHS (1.6 g, 0.08 mmol, prepared in last step) was dissolved in dichloromethane (30 mL), and cooled under the protection of N₂, then diisopropylethylamine (19.4 mg, 0.15 mmol) was added, and the mixture was stirred evenly. After that, hydrochloricacid adriamycin (69.6 mg, 0.12 mmol) was added, and after the addition of hydrochloricacid adriamycin, the mixture was reacted at room temperature for 5 hours. After the reaction solution was concentrated, the residues were crystallized with isopropyl alcohol, subjected to suction filtration and then dried to obtain 1.3 g of red solid product PEG-L3-Dox (20K) in 81.2% yield. $^1$H NMR: (DMSO-d6): δ8.81 (s, 2H), 8.68 (s, 2H), 7.62 (m, 2H), 7.53 (d, 2H), 7.33 (d, 8H), 7.16 (d, 4H), 5.52 (s, 4H), 5.12 (t, 2H), 4.83 (s, 4H), 4.54 (d, 2H), 4.32 (t, 2H), 4.06 (m, 2H), 3.96 (s, 6H), 3.71 (m, 2H), 3.67 (m, 1800H), 3.41 (s, 4H), 3.27 (m, 2H), 2.97 (m, 2H), 2.39 (s, 4H), 2.28 (d, 4H), 2.05 (d, 4H), 1.34 (d, 6H), 1.16 (d, 12H).

Example 18: Preparation of 4Arm-PEG-L3 (20K)

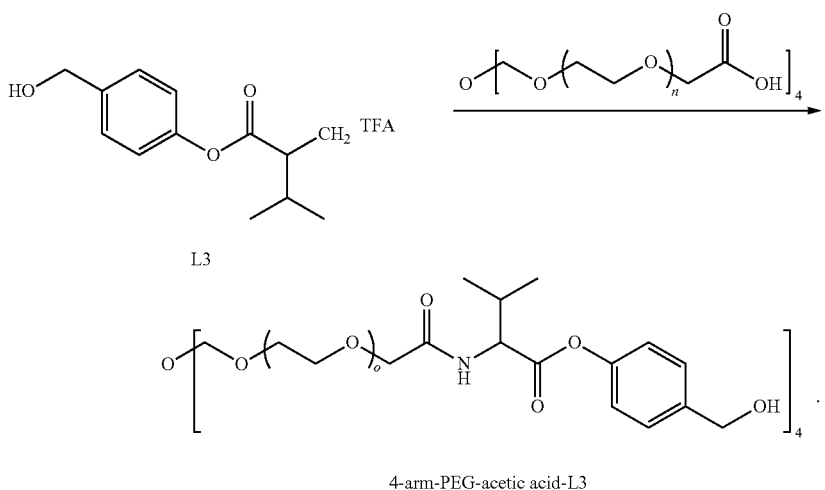

4-arm-PEG-acetic acid-L3

4arm-PEG-acetic acid (20K, 5 g, 0.025 mmol), compound L3 (674 mg, 2.0 mmol, prepared in Example 1) and 1-hydroxybenzotriazole (HOBt, 135.1 mg, 1 mmol) were added to a reaction flask, dissolved with dichloromethane, and then diisopropylethylamine (129.1 mg, 1.0 mmol) was added. The mixture was stirred evenly, cooled in an ice-bath, and then EDCI (191.7 mg, 1 mmol) was added in batches. After the addition of EDCI, the reaction system was naturally warmed up to room temperature and reacted overnight. After the reaction solution was concentrated the next day, the residues were crystallized with isopropyl alcohol, subjected to suction filtration and dried to obtain 4.7 g of product 4arm-PEG-L3 (20K) in 94.0% yield.

Example 19: Preparation of 4Arm-PEG-L3-Dox (20K)

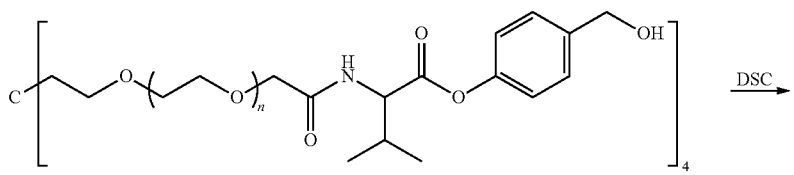

4arm-PEG-acetic acid-L3-

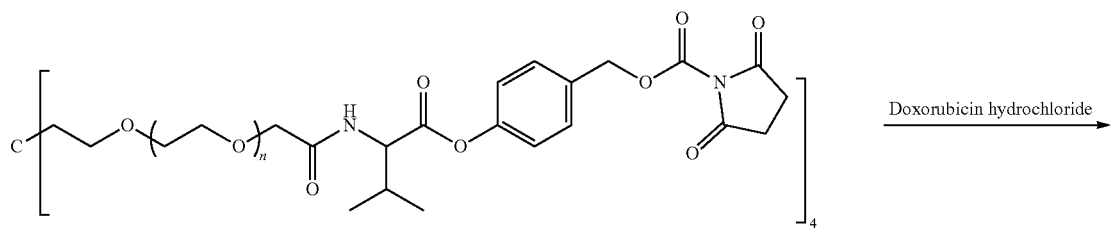

4arm-PEG-acetic acid-NHS-

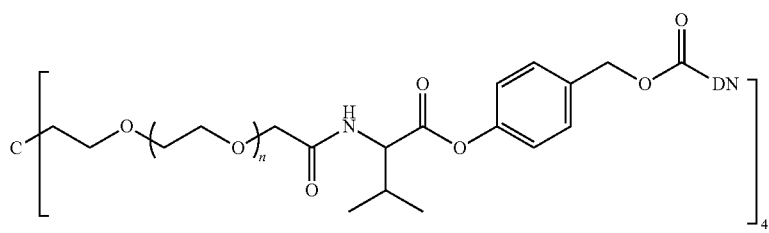

4arm-PEG-acetic acid-Dos-

Compound 4arm-PEG-L3 (2 g, 0.1 mmol, prepared in Example 18) was added into a reaction flask, dissolved with dichloromethane (40 mL), and cooled under the protection of $N_2$, then succinimide carbonate (1.02 g, 0.4 mmol) was added, and the mixture was stirred and dissolved. After that, triethylamine (60.6 mg, 0.6 mmol) was added, and a cold bath was removed after the addition of triethylamine, and the mixture was reacted overnight at room temperature. After the reaction solution was concentrated, the residues were crystallized with isopropyl alcohol to obtain 1.8 g of product 4arm-PEG-L3-NHS (20K) in 90.0% yield.

Compound 4arm-PEG-L3-NHS (1.5 g, 0.075 mmol, prepared in last step) was dissolved in dichloromethane (30 mL), and cooled under the protection of $N_2$, then diisopropylethylamine (77.5 mg, 0.6 mmol) was added, and the mixture was stirred evenly. After that, hydrochloricacid adriamycin (261 mg, 0.45 mmol) was added, and after the addition of hydrochloricacid adriamycin, the mixture was reacted at room temperature for 5 hours. After the reaction solution was concentrated, the residues were crystallized with isopropyl alcohol, subjected to suction filtration and then dried to obtain 1.3 g of red solid product 4arm-PEG-L3-Dox (20K) in 86.7% yield. $^1$H NMR: (DMSO-d6): δ8.82 (s, 4H), 8.67 (s, 4H), 7.62 (m, 4H), 7.53 (d, 4H), 7.33 (d, 8H), 7.16 (d, 12H), 5.51 (s, 8H), 5.12 (t, 4H), 4.83 (s, 8H), 4.55 (t, 4H), 4.33 (m, 12H), 4.06 (m, 4H), 3.95 (s, 12H), 3.67 (m, 1800H), 3.55 (t, 8H), 3.47 (s, 4H), 3.28 (m, 4H), 3.08 (m, 4H), 2.27 (d, 8H), 2.04 (m, 8H), 1.68 (t, 8H), 1.42 (d, 12H), 1.16 (d, 24H).

Example 20: Preparation of 8Arm-PEG-L4-NHS (20K)

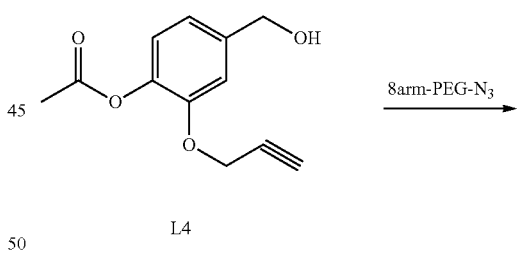

L4

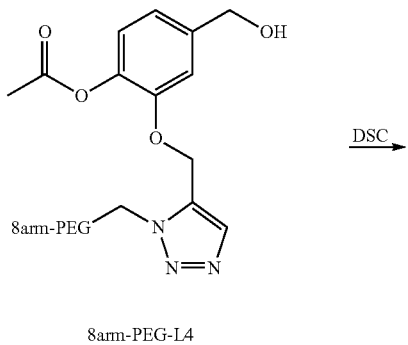

8arm-PEG-L4

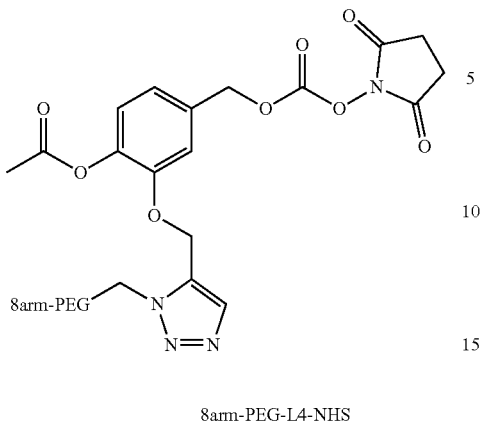

8arm-PEG-L4-NHS 8-arm-PEG-N₃ (20K, 2 g, 0.1 mmol), compound L4 (prepared using the method in Chinese patent application CN201510354709.6, 220 mg, 1 mmol), vitamin C (440 mg, 2.5 mmol) were added into N,N-dimethylformamide (20 mL), quickly stirred to dissolve the mixture, then an aqueous solution (4.4 mL 2.2 mL/g PEG) of copper sulfate pentahydrate (250 mg, 1 mmol) was added to react overnight at room temperature, and the mixture was deposited with isopropyl alcohol to obtain 1.8 g of product.

Compound 8arm-PEG-L4 (2 g, 0.1 mmol, prepared in last step) was added into a reaction flask, dissolved with dichloromethane (40 mL), and cooled under the protection of N₂, then succinimide carbonate (1.02 g, 0.4 mmol) was added, and the mixture was stirred and dissolved. After that, triethylamine (60.6 mg, 0.6 mmol) was added, and a cold bath was removed after the addition of triethylamine, and the mixture was reacted overnight at room temperature. After the reaction solution was concentrated, the residues were crystallized with isopropyl alcohol to obtain 1.7 g of product 8arm-PEG-L4-NHS (20K) in 85% yield.

Example 21: Preparation of 8Arm-PEG-L4-Dox (20K)

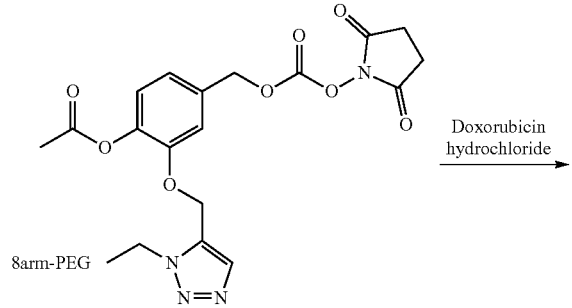

8arm-PEG-L4-NHS

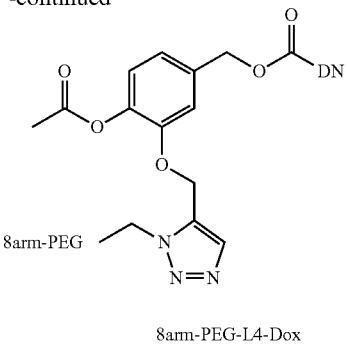

8arm-PEG-L4-Dox

Compound 8arm-PEG-L4-NHS (20K, 1.5 g, 0.075 mmol, prepared in Example 20) was dissolved in dichloromethane (30 mL), and cooled under the protection of N₂, then diisopropylethylamine (77.5 mg, 0.6 mmol) was added, and the mixture was stirred evenly. After that, hydrochloricacid adriamycin (261 mg, 0.45 mmol) was added, and after the addition of hydrochloricacid adriamycin, the mixture was reacted at room temperature for 5 hours. After the reaction solution was concentrated, the residues were crystallized with isopropyl alcohol, subjected to suction filtration and then dried to obtain 1.4 g of red solid product 8arm-PEG-L4-Dox (20K) in 93.3% yield.

Example 22: Preparation of 4Arm PEG-L5-Dox (20K)

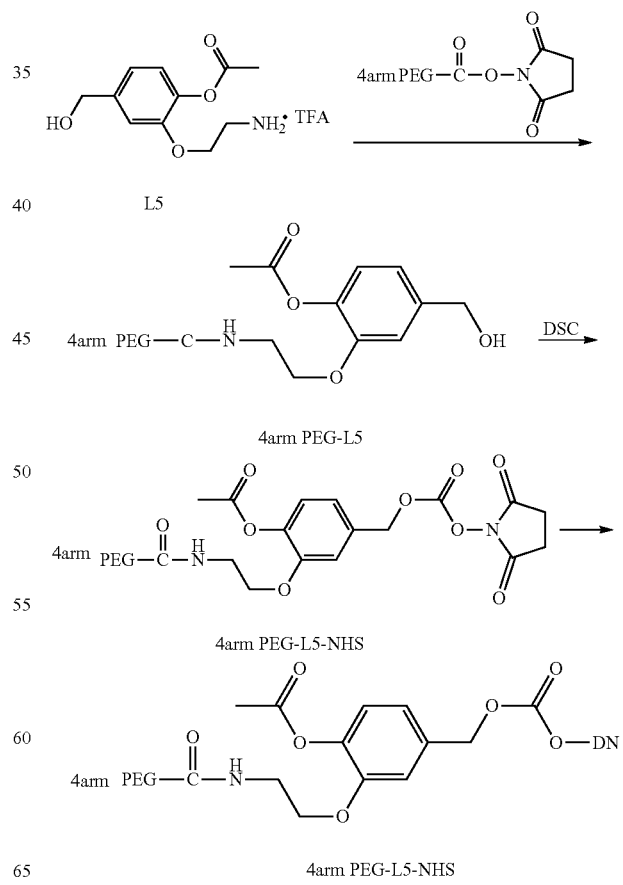

Synthesis of 4Arm PEG-L5

4arm PEG (20K)-CM-NHS (2 g, 0.1 mmol) was dissolved in anhydrous methylene chloride, and subcooled to 0° C. DIPEA (78 mg, 0.6 mmol) was added, and then compound L5 (prepared in Example 3) was added. The mixture was slowly warmed up to room temperature and stirred overnight. After the reaction solution was concentrated, the residues were crystallized with isopropyl alcohol, subjected to suction filtration and then dried to obtain a product 4arm PEG-L5 (1.8 g, 90%). $^1$H NMR: (DMSO-d6): δ8.11 (s, 4H), 6.86 (s, 4H), 6.74 (d, 4H), 6.65 (d, 4H), 5.35 (s, 8H), 4.20 (m, 8H), 3.66 (m, 1800H), 3.52 (m, 4H), 3.24 (s, 6H), 2.78 (m, 8H), 2.13 (s, 6H).

Synthesis of 4Arm PEG-L5-NHS

Compound 4arm PEG-L5 (1.5 g, 0.075 mmol, prepared in last step) was added into a reaction flask, dissolved with dichloromethane (30 mL), and cooled under the protection of $N_2$, then succinimide carbonate (68.0 mg, 0.03 mmol) was added, and the mixture was stirred and dissolved. After that, DIPEA (51.6 mg, 0.4 mmol) was added, and a cold bath was removed after the addition of DIPEA, and the mixture was reacted overnight at room temperature. After the reaction solution was concentrated, the residues were crystallized with isopropyl alcohol to obtain a product 4armPEG-L5-NHS (1.4 g, 93%). 1H NMR: (DMSO-d6): δ8.12 (s, 4H), 6.85 (s, 4H), 6.72 (d, 4H), 6.65 (d, 4H), 4.65 (s, 8H), 4.15 (m, 8H), 3.65 (m, 1800H), 3.29 (m, 8H), 3.24 (s, 12H), 2.12 (s, 9H).

Synthesis of 4Arm PEG-L5-Dox

Compound 4arm PEG-NHS (1 g, 0.05 mmol, prepared in last step) was added in a reaction flask, dissolved with dichloromethane (20 mL), and cooled under the protection of $N_2$, then diisopropylethylamine was added, and the mixture was stirred evenly. After that, hydrochloricacid adriamycin (348.8 mg, 0.3 mmol) was added, and after the addition of hydrochloricacid adriamycin, the mixture was reacted overnight at room temperature. After the reaction solution was concentrated, the residues were crystallized with isopropyl alcohol, subjected to suction filtration and then dried to obtain a brownish red solid product 4arm PEG-L5-Dox (0.84 g, 84%). 1H NMR: (DMSO-d6): δ8.81 (s, 4H), 8.67 (s, 4H), 7.63 (m, 4H), 7.53 (d, 4H), 7.34 (d, 8H), 7.17 (d, 12H), 5.52 (s, 8H), 5.12 (t, 4H), 4.83 (s, 8H), 4.55 (t, 4H), 4.33 (m, 12H), 4.06 (m, 4H), 3.95 (s, 12H), 3.67 (m, 1800H), 3.55 (t, 8H), 3.47 (s, 4H), 3.28 (m, 4H), 3.09 (m, 4H), 2.26 (d, 8H), 2.05 (m, 8H), 1.66 (t, 8H), 1.43 (d, 12H), 1.17 (d, 24H).

Example 23: Research on Tumor Growth Inhibition in HCT116 Tumor Heterotopic Transplantation Mouse Model Experimental Purpose:

The experiment was carried out to detect a tumor growth inhibition effect of a drug on the HCT116 tumor heterotopic transplantation mouse model.

Drug Grouping:
G1: solvent;
G2: positive drug adriamycin (commercially available); and
G3: 4arm PEG-L5-Dox (prepared in Example 22).

Experimental Method:

Cell Culture:

An original culture solution was removed by suction after HCT116 cells (commercially available) were received, and 10 mL of fresh culture solution was added. The cells were collected and passaged when 90% of the cells were converged. After the culture solution was removed, 10 ml of EDTA/PBS solution was added and placed at room temperature for 5 minutes, and then the EDTA/PBS solution was removed by suction. 3 ml of 0.25% pancreatin (37° C.) was evenly mixed and spread on cell surfaces, and then immediately removed by suction. The culture flask with no medium was put into an incubator until the cells were separated from a wall of the culture flask (5 minutes). 20 mL of DMEM containing 10% FBS was added, and gently blown and beaten to blend the cells. The cells was counted with a counting plate and diluted with DMEM containing 10% FBS. 40 mL of cell suspension was transferred to a 150 mm cell culture dish and then put into an incubator. The cell suspension was changed every other day, and when 80% of the cells were converged, the cells were passaged using the same method above.

Preparation of Cell Suspension for Inoculation:

The cell suspension was changed in advance when it was detected that 80% of the cells were converged on the inoculation day of the cells. After 3 hours, the culture solution was removed by a pipette, 20 ml of EDTA/PBS solution was added in each dish and placed at room temperature for 5 minutes, and then the EDTA/PBS solution was removed by suction. 3 ml of 0.25% pancreatin (37° C.) was evenly mixed and spread on cell surfaces, and then immediately removed by suction. The culture flask with no medium was put into an incubator until the cells were separated from a wall of the culture flask (5 minutes). 20 mL of DMEM containing 10% FBS was added, and gently blown and beaten to blend the cells. The supernatant was removed after the cell suspension was transferred to a centrifuge tube and centrifuged at a room temperature for 5 minutes, and then serum-free DMEM was added, and gently blended. The mixture was centrifuged again, the supernatant was removed, and a small amount of ice-cold PBS was added, and gently blended. The cells were counted with a counting plate and diluted with PBS to a concentration of $2*10^7$ cells/mL, and then the cells were placed on ice until inoculation.

Tumor Inoculation:

HCT116 cells were subcutaneously inoculated in a right front axilla of a mouse. Each mouse was inoculated with 200 μL of PBS cell suspension, and a total of 30 mice were inoculated. Tumor volumes were measured twice a week after inoculation, and when an average tumor volume reached 100 to 200 mm$^3$, 18 mice with similar tumor sizes were selected and randomly divided into 3 groups with 6 mice in each group. The mice were administrated within 24 hours after grouping, and the mice were weighted before each administration to adjust a dosage. The mice were continuously observed and measured after last administration, the body weights and the tumor volumes were measured twice a week, and the tumor volume (mm$^3$) was calculated according to a formula that $V=0.5(a*b^2)$, wherein a represented a length diameter and b represented a width diameter. When the average tumor volume of the mice in a certain group was greater than 2000 mm$^3$, the mice in the group were sacrificed. Differences of the tumor volumes among the groups were compared by a t test, and $P<0.05$ was regarded as a statistically significant difference.

Figure 6:
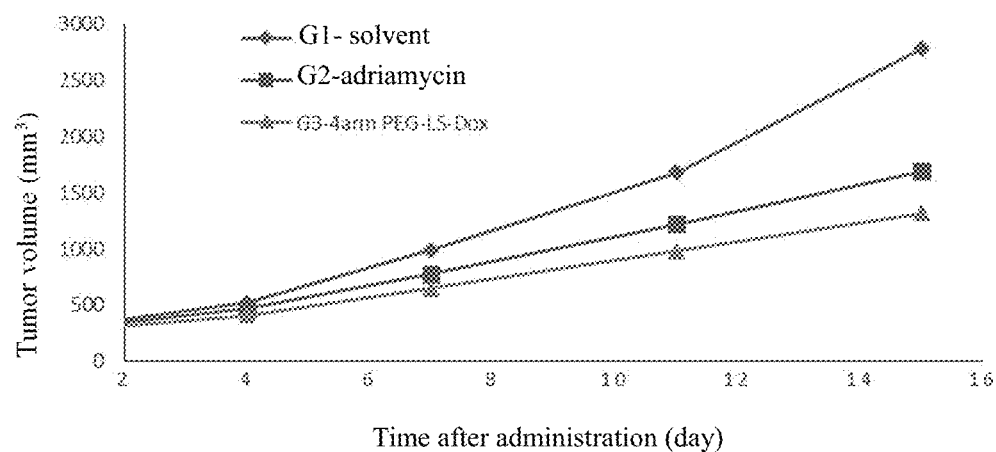
FIG. 6 illustrates an efficacy research experimental result obtained in Example 23.

Experimental Results:

The experimental results are shown in FIG. 6, both the positive drug adriamycin and the compound 4armPEG-L5-Dox have obvious anti-tumor effects, and the compound 4arm PEG-L5-Dox has a better effect than that of the adriamycin, and the effect gap is gradually increased with the prolonging of an administration time, which is probably related to a fact that the adriamycin in the compound 4arm PEG-L5-Dox uses polyethylene glycol as a carrier, so that the drug can stay at a tumor site for a longer time and can achieve the effects of sustained-release and controlled-release. Weight losses of the mice during the administration are acceptable, and it is valuable to further research the compound.

The "coupling degree" in the example of the disclosure refers to a number of PEG molecules coupled to each IL-2 molecule (i.e., the n value in the general formula IX of the disclosure), for example, mPEG-L5-rhIL-2 with a coupling degree of 4 refers to coupling 4 mPEG-L5 chain segments to each rhIL-2 molecule; mPEG-L5-rhIL-2 with a coupling degree of 4 to 7 refers to a mixture containing mPEG-L5-rhIL-2 with a coupling degree of 4, mPEG-L5-rhIL-2 with a coupling degree of 5, mPEG-L5-rhIL-2 with a coupling degree of 6, and mPEG-L5-rhIL-2 with a coupling degree of 7.

The DN structure in the reaction formulae of Examples 17, 19, 21 and 22 of the disclosure is

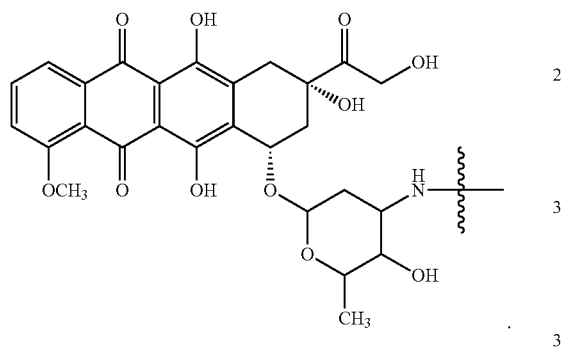

Those described above are merely preferred examples of the disclosure, but are not intended to limit the disclosure. Any modifications and equivalent substitutions made without departing from the principle of the disclosure shall all fall within the scope of protection of the disclosure.

What is claimed is:
1. A polyethylene glycol-linker-drug conjugate, having a structure as follows:

$(PEG-X-L-Y)_n-D$      (IX)

wherein, PEG is a polyethylene glycol residue,

X is a linking group of PEG and L, which is selected from one or a combination of several of —$(CH_2)_a$—, —$(CH_2)_aCO$—, —$(CH_2)_aOCO$—, —$(CH_2)_aNHCO$—, —$NH(CH_2)_aCO$—, —$(CH_2)_aSO_2$—, —$O(CH_2)_a$—, —$O(CH_2)_aCO$—, —$O(CH_2)_aOCO$—, —$O(CH_2)_aNHCO$— and —$O(CH_2)_aSO_2$—, and a is an integer of 0 to 10, Y is a linking group of L and D, which is selected from one or a combination of several of —$(CH_2)_r$—,

—$(CH_2)_rO$—,    —$(CH_2)_rCO$—,    —$(CH_2)_rNH$—, —$(CH_2)_rCONH$—, —$(CH_2)_rNHCO$—, —$(CH_2)_rSH$—,

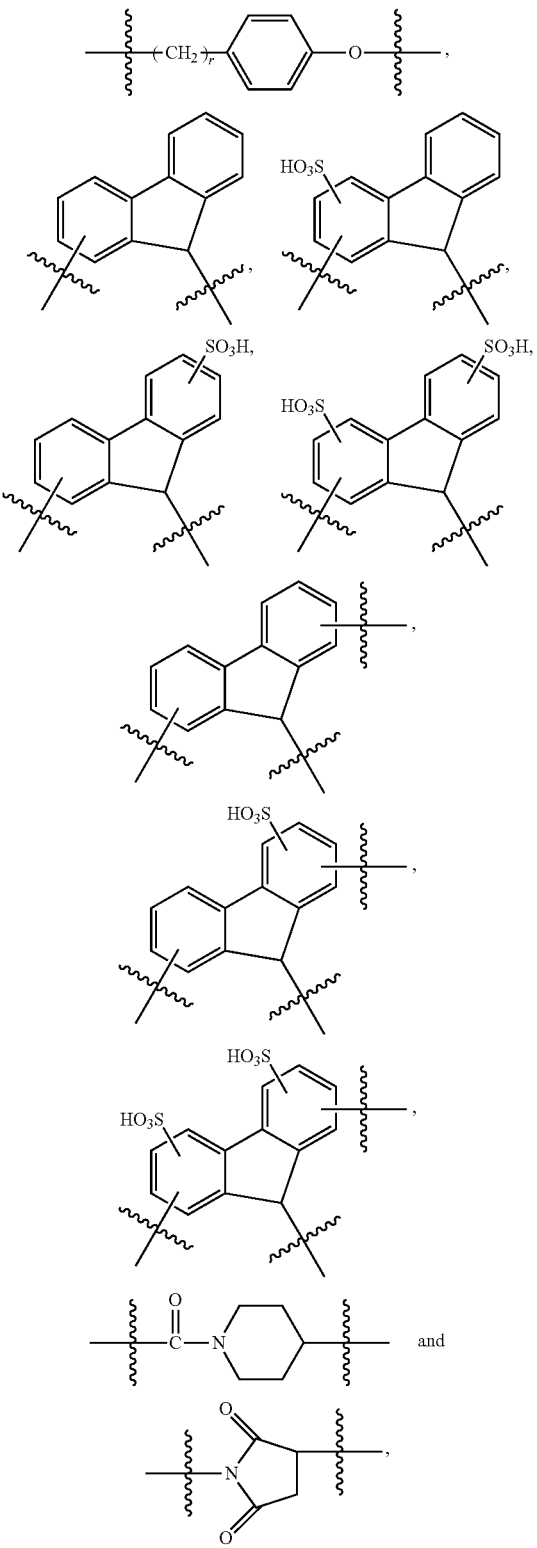

and r is an integer of 0 to 10, $R_{17}$ and $R_{18}$ are independently selected from —H, C1-6 alkyl, C1-6 alkoxy, C3-6 cycloalkyl and C4-10 alkylene cycloalkyl, D is a bioactive agent containing m amido groups, and m is an integer of 1 to 500, n is an integer, and 1≤n≤m, L is a linker, having a structure as follows:

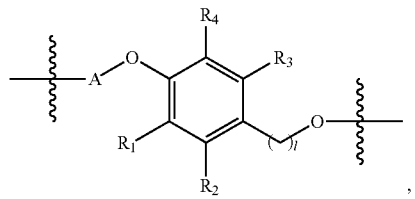
(L-a)

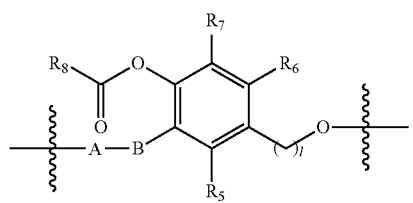
(L-b), or

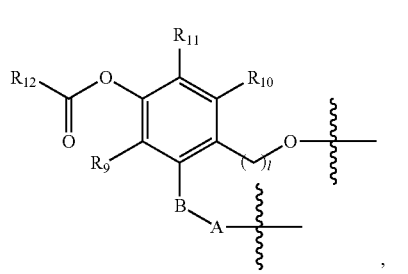
(L-c)

wherein, 1 is an integer of 1 to 5, in the linker L-a, A is —COCH$_2$NH—, —COCH(CH$_3$)NH— or —COCH(CH(CH$_3$)$_2$)NH—;

in the linker L-b and L-c, A is one or a combination selected from amino acid residues, polypeptide residues,

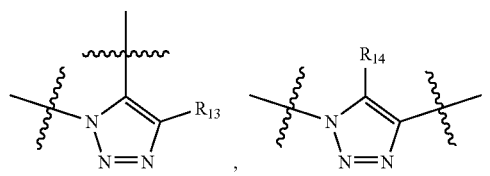

—NHCO(CH$_2$)$_i$—, —CONH(CH$_2$)$_i$—, —(CH$_2$)$_i$NH— and —CO(CR$_{15}$R$_{16}$)$_i$NH—, and i is an integer of 0 to 6, R$_{1-7}$ and R$_{9-11}$ are independently selected from —H, —F, —Cl, —Br, —I, C1-6 alkyl, C1-6 alkoxy, C3-6 cycloalkyl, C1-6 alkenyl, C6-12 aryl, C6-12 aralkyl, C3-12 aromatic or non-aromatic heterocyclyl, C3-12 heterocyclic alkyl and —(CH$_2$)$_j$—O—Z, wherein Z is selected from —H, —CH$_3$, —C(CH$_3$)$_3$, —CH$_2$OCH$_3$, —COCH$_3$, —COC(CH$_3$)$_3$, —CH$_2$CH=CH$_2$, —Si(CH$_3$)$_3$,

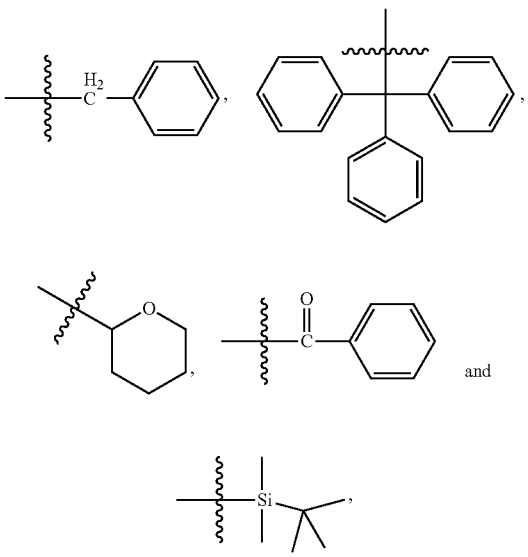

R$_8$ and R$_{12}$ are independently selected from C1-6 alkyl,

R$_{13-16}$ are independently selected from —H, and C1-6 alkyl, and

B is a linking group —B$_1$—B$_2$—, wherein, B$_1$ is selected from —(CH$_2$)$_j$—, —NHCO(CH$_2$)$_j$— and —CONH(CH$_2$)$_j$—, and j is an integer of 0 to 6, and B$_2$ is selected from —C=O, —C=S, —O—, —S—, —C(O)O—, —C(O)S—, —C(S)O— and —S—S—.

2. The conjugate of claim 1, wherein D is selected from a polypeptide drug and a protein drug.

3. The conjugate of claim 1, wherein D is a IL-2.

4. The conjugate of claim 1, wherein D comprises adriamycin and derivative thereof, crizotinib, goserelin, cytarabine, procaine, benzocaine, chloroprocaine, dimethocaine, dopamine, norepinephrine, clenbuterol, phenformin, daraprim, prosultiamine, p-aminosalicylic acid and sulfadiazine.

5. The conjugate of claim 1, wherein D is adriamycin, which has a following structure:

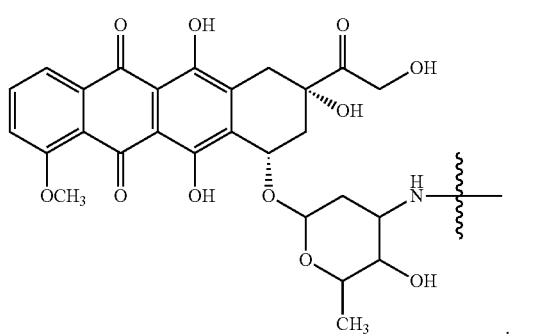
(X)

wherein, W$_1$ is selected from —H, —OH, —OCH$_3$ and —OCH$_2$CH$_3$;

W₂ is selected from —H, —OH, —OCO(CH₂)₅COOH and —OCO(CH₂)₂NH₂;

W₃ is selected from —OH, —OCH₃ and

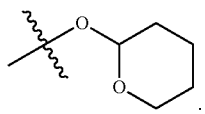

6. The conjugate of claim 5, wherein W₁ is —OCH₃, W₂ is —OH; W₃ is —OH.

7. The conjugate of claim 2, wherein n is an integer of 1 to 12.

8. The conjugate of claim 1, wherein in the linker, R₅₋₇ are all —H;

R₉₋₁₁ are all —H;

R₈ and/or R₁₂ is methyl;

l is 1;

and in the linker L-b or L-c, —B-A- is —OCH₂CH₂NH—.

9. The conjugate of claim 1, wherein X is selected from one or a combination of several of —(CH₂)ₐ—, —(CH₂)ₐCO—, —(CH₂)ₐNHCO—, —NH(CH₂)ₐCO—, —O(CH₂)ₐ—, —O(CH₂)ₐCO—, and —O(CH₂)ₐNHCO—; and/or, Y is a combination of —(CH₂)ᵣCO— and one or several of single bond, —CH₂—, —CH₂CH₂—, —CH₂CH₂CH₂—, —CH₂CH₂CH₂CH₂—, —CH₂CH₂CH₂CH₂CH₂—, —CH(CH₃)—, —CH₂CH(CH₃)—, —CH₂CH₂CH(CH₃)—, —CH₂CH₂CH₂CH(CH₃)—, —CH₂CH₂CH₂CH₂CH(CH₃)—, —CH₂CH₂CH₂CH₂CH₂CH(CH₃)—, —(CH₂)ᵣCONH—, —(CH₂)ᵣNHCO—, —(CH₂)ᵣNH—, —(CH₂)ᵣSH—,

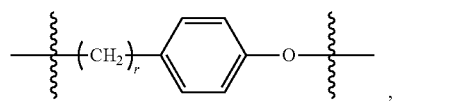

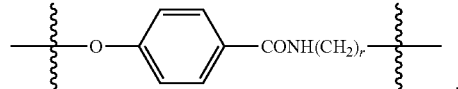

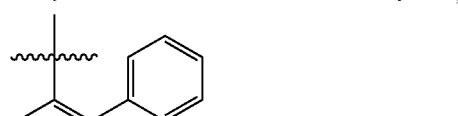

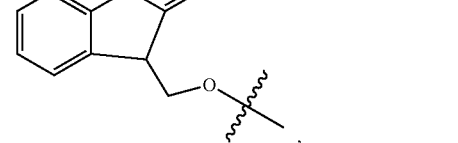

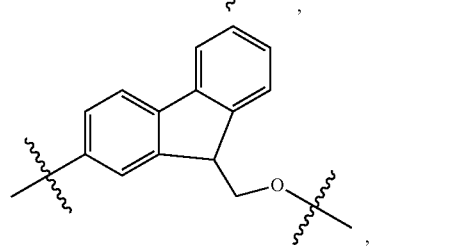

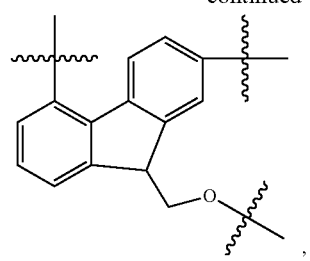

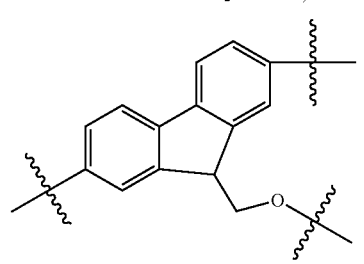

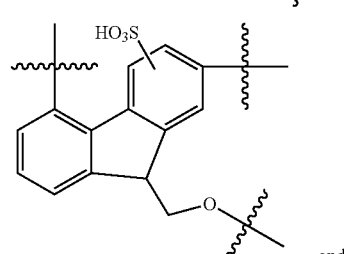

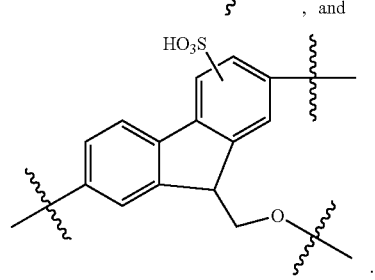

10. The conjugate of claim 1, wherein X is a single bond, —CH₂—, —CH₂CH₂—, —CO—, —CH₂CO— or —NHCO—; and/or, Y is —CO—.

11. The conjugate of 1, wherein the conjugate has a structure as follows:

(IX-a)

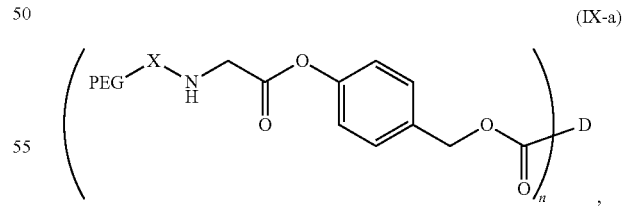

(IX-b)

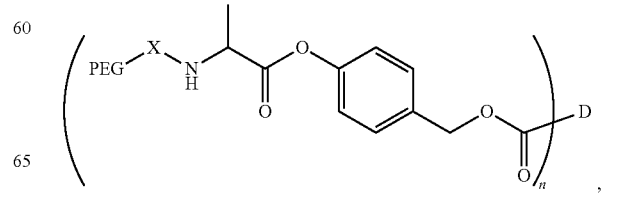

-continued (IX-c)

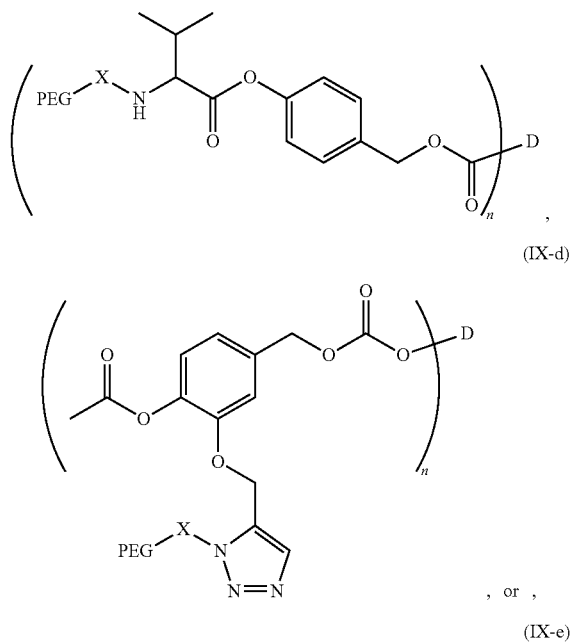

(IX-d)

, or , (IX-e)

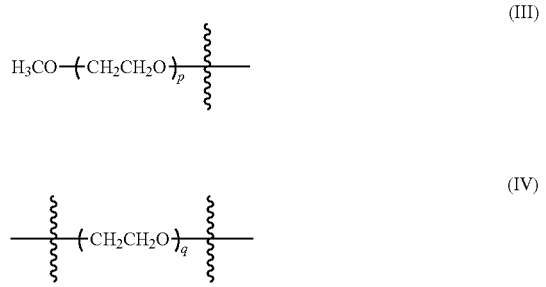

12. The conjugate of claim 11, wherein PEG is a linear-chain polyethylene glycol residue which has a structure of a general formula III:

(III)

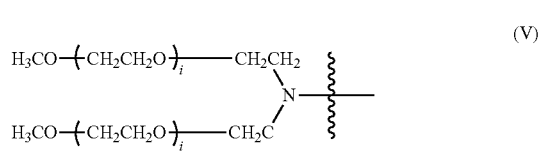

(IV)

wherein, p is selected from an integer of 1 to 960;
or,
the PEG is a Y-type polyethylene glycol residue having a structure of general formula V or VI:

(V)

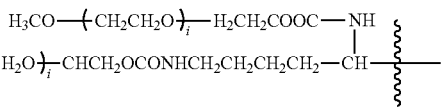

(VI)

wherein, i and h are independently selected from an integer of 1 to 480;
or,
the PEG is a multi-branched polyethylene glycol residue having a structure of general formula VII;

(VII)

wherein, k is an integer of 1 to 320,
j is an integer of 3 to 8, and
R is a core molecule of multi-branched polyethylene glycol, and R is selected from residues of pentaerythritol, oligomerized pentaerythritol, methyl glucoside, sucrose, diglycol, propylene glycol, glycerol and polyglycerol.

13. The conjugate of claim 12, wherein the multi-branched polyethylene glycol residue has a structure as follows:

(VII-1)

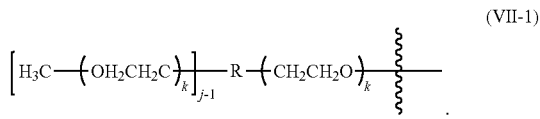

14. The conjugate of claim 13, wherein the multi-branched polyethylene glycol residue has a structure as follows:

(VII-2)

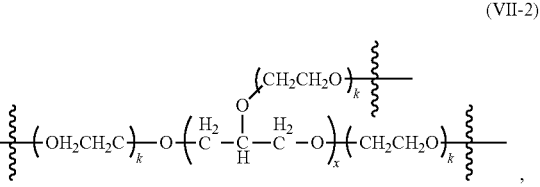

(VII-3)

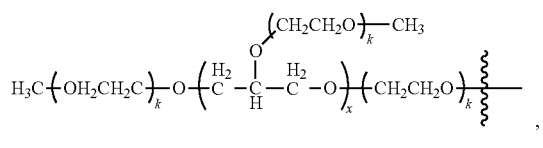

(VII-4)

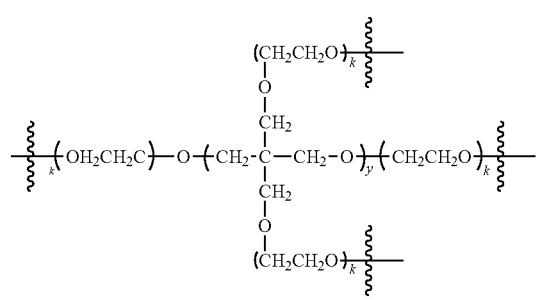

(VII-5)

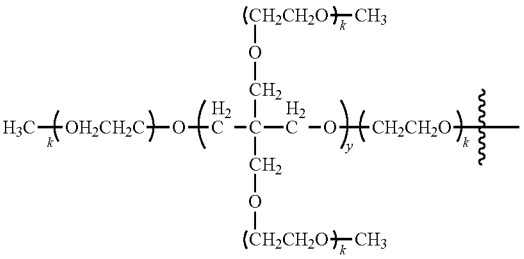

wherein, x and y are independently selected from an integer of 1 to 10.

15. The conjugate of claim 1, wherein the molecular weight of the PEG is 1 to 100 KDa.

16. The conjugate of claim 1, wherein a molecular weight of the PEG is 10 to 50 KDa.

17. A pharmaceutical composition comprising the polyethylene glycol-linker-drug conjugate according to claim 1.

18. A method for manufacturing a drug for preventing and/or treating a disease, comprising providing the polyethylene glycol-linker-drug conjugate of claim 1.

19. The method of claim 18, wherein the disease refers to a tumor, an autoimmune disease, a viral disease or a bacterial disease.

* * * * *